US009550029B2

(12) United States Patent
Boyden et al.

(10) Patent No.: US 9,550,029 B2
(45) Date of Patent: Jan. 24, 2017

(54) SYSTEMS AND METHODS FOR GUIDING INJECTIONS

(71) Applicant: Elwha LLC, Bellevue, WA (US)

(72) Inventors: Edward S. Boyden, Chestnut Hill, MA (US); Hon Wah Chin, Palo Alto, CA (US); Gregory J. Della Rocca, Columbia, MO (US); Daniel Hawkins, Bellevue, WA (US); Roderick A. Hyde, Redmond, WA (US); Robert Langer, Newton, MA (US); Eric C. Leuthardt, St. Louis, MO (US); Terence Myckatyn, St. Louis, MO (US); Parag Jitendra Parikh, St. Louis, MO (US); Dennis J. Rivet, Chesapeake, VA (US); Joshua S. Shimony, St. Louis, MO (US); Michael A. Smith, Phoenix, AZ (US); Elizabeth A. Sweeney, Seattle, WA (US); Clarence T. Tegreene, Mercer Island, WA (US)

(73) Assignee: Elwha LLC, Bellevue, WA (US)

( * ) Notice: Subject to any disclaimer, the term of this patent is extended or adjusted under 35 U.S.C. 154(b) by 1093 days.

(21) Appl. No.: 13/664,138

(22) Filed: Oct. 30, 2012

(65) Prior Publication Data

US 2014/0121636 A1   May 1, 2014

(51) Int. Cl.
*A61M 31/00* (2006.01)
*A61M 5/42* (2006.01)
*A61F 7/00* (2006.01)

(52) U.S. Cl.
CPC ............... *A61M 5/427* (2013.01); *A61B 90/11* (2016.02); *A61B 90/13* (2016.02); *A61B 2090/364* (2016.02); *A61F 7/00* (2013.01)

(58) Field of Classification Search
CPC ............ A61B 17/3403; A61B 2034/2055; A61B 2090/366; A61B 5/0037; A61B 5/0621; A61B 5/4887
(Continued)

(56) References Cited

U.S. PATENT DOCUMENTS 4,362,157 A    12/1982  Keeth
4,384,288 A     5/1983  Walton
(Continued)

FOREIGN PATENT DOCUMENTS

GB      2 431 110 A      4/2007
WO     WO 80/00060       1/1980
WO   WO 2004/035110 A2   4/2004

OTHER PUBLICATIONS

"CFR Code of Federal Regulations Title 21" U.S. Food & Drug Administration, Sep. 26, 2012, pp. 1-18. http://www.accessdata.fda.gov/scripts/cdrh/cfdocs/cfCFR/CFRSearch.cfm?FR=1040.10.
(Continued)

*Primary Examiner* — Phillip Gray

(57) ABSTRACT

Systems and methods are described herein for guided injection, which include: one or more controllable light-emitting elements configured to emit non-destructive light and a computing device operably connected to the one or more controllable light-emitting elements configured to emit non-destructive light, the computing device including a processor operable to receive at least one digital representation of a body region of an individual, the body region of the individual including one or more physical registration landmarks, the at least one digital representation including one or more digitally registered injection sites and one or more digital registration landmarks corresponding to the one or more physical registration landmarks on the body region; and control the one or more controllable light-emitting elements to illuminate a location of a surface of the body
(Continued)

region of the individual corresponding in location to at least one of the one or more digitally registered injection sites.

23 Claims, 39 Drawing Sheets

(58) Field of Classification Search
USPC .................................................. 604/500–506
See application file for complete search history.

(56) References Cited

U.S. PATENT DOCUMENTS

| | | | |
|---|---|---|---|
| 4,614,189 A | 9/1986 | MacKenzie | |
| 4,679,553 A | 7/1987 | Proulx et al. | |
| 5,356,396 A | 10/1994 | Wyatt et al. | |
| 5,466,233 A | 11/1995 | Weiner et al. | |
| 5,752,962 A | 5/1998 | D'Urso | |
| 5,782,842 A | 7/1998 | Kloess et al. | |
| 5,860,957 A | 1/1999 | Jacobsen et al. | |
| 5,971,763 A | 10/1999 | Yau | |
| 6,036,632 A | 3/2000 | Whitmore, III et al. | |
| 6,041,249 A * | 3/2000 | Regn | A61B 6/08 378/20 |
| 6,196,223 B1 | 3/2001 | Belfer et al. | |
| 6,200,255 B1 | 3/2001 | Yu | |
| 6,216,029 B1 | 4/2001 | Paltieli | |
| 6,311,084 B1 | 10/2001 | Cormack et al. | |
| 6,350,276 B1 | 2/2002 | Knowlton | |
| 6,522,911 B1 | 2/2003 | Toida et al. | |
| 6,551,613 B1 | 4/2003 | Dong et al. | |
| 6,689,142 B1 | 2/2004 | Tremaglio, Jr. et al. | |
| 7,215,976 B2 | 5/2007 | Brideglall | |
| 7,713,239 B2 | 5/2010 | Uber, III et al. | |
| 7,825,776 B2 | 11/2010 | Smith et al. | |
| 7,846,465 B1 | 12/2010 | Keller et al. | |
| 7,891,570 B2 | 2/2011 | Difazio et al. | |
| 8,133,201 B1 | 3/2012 | Hurtado | |
| 8,260,010 B2 | 9/2012 | Chhibber et al. | |
| 8,944,058 B2 | 2/2015 | Ging et al. | |
| 2002/0103457 A1 | 8/2002 | Fontayne et al. | |
| 2003/0060763 A1 | 3/2003 | Penfold et al. | |
| 2003/0065578 A1 | 4/2003 | Peyrelevade et al. | |
| 2003/0216675 A1 | 11/2003 | Rooney | |
| 2004/0068037 A1 | 4/2004 | Mitadera et al. | |
| 2004/0078000 A1 | 4/2004 | Borchard et al. | |
| 2004/0153031 A1 | 8/2004 | Van Kaauwen | |
| 2004/0161435 A1 | 8/2004 | Gupta | |
| 2004/0242976 A1 | 12/2004 | Abreu | |
| 2005/0137584 A1 | 6/2005 | Lemchen | |
| 2005/0148935 A1 | 7/2005 | Dimitrova et al. | |
| 2005/0159759 A1 | 7/2005 | Harbaugh et al. | |
| 2005/0240133 A1 | 10/2005 | Rooney | |
| 2006/0271025 A1 | 11/2006 | Jones et al. | |
| 2007/0243225 A1 | 10/2007 | McKay | |
| 2007/0260182 A1 | 11/2007 | Munday | |
| 2008/0044797 A1 | 2/2008 | Bardach et al. | |
| 2008/0167674 A1 | 7/2008 | Bodduluri et al. | |
| 2008/0171930 A1 | 7/2008 | Abolfathi et al. | |
| 2008/0237366 A1 | 10/2008 | Ehlert et al. | |
| 2008/0237367 A1 | 10/2008 | McNichols et al. | |
| 2008/0262424 A1 | 10/2008 | van't Hooft | |
| 2008/0306392 A1 | 12/2008 | Satoguchi et al. | |
| 2009/0030338 A1 | 1/2009 | Crocker et al. | |
| 2009/0092948 A1 | 4/2009 | Gantes | |
| 2009/0234370 A1 * | 9/2009 | Haras | A61B 17/3403 606/130 |
| 2009/0243813 A1 | 10/2009 | Smith et al. | |
| 2010/0015590 A1 | 1/2010 | Kiss | |
| 2010/0179473 A1 | 7/2010 | Genosar | |
| 2010/0204695 A1 | 8/2010 | Metha et al. | |
| 2010/0312100 A1 | 12/2010 | Zarkh et al. | |
| 2011/0060309 A1 | 3/2011 | Lee et al. | |
| 2011/0112508 A1 | 5/2011 | Panzirer | |
| 2011/0118560 A1 | 5/2011 | Eckhoff et al. | |
| 2011/0178518 A1 | 7/2011 | Sohn | |
| 2011/0202032 A1 | 8/2011 | Shih et al. | |
| 2011/0228907 A1 | 9/2011 | Gagnon et al. | |
| 2011/0238038 A1 | 9/2011 | Sefi et al. | |
| 2011/0245951 A1 | 10/2011 | Gantes | |
| 2011/0295230 A1 | 12/2011 | O'Dea et al. | |
| 2012/0046668 A1 | 2/2012 | Gantes | |
| 2012/0100500 A1 | 4/2012 | Gao | |
| 2012/0192330 A1 | 8/2012 | McMullen | |
| 2012/0247474 A1 | 10/2012 | Torbenson | |
| 2012/0265187 A1 | 10/2012 | Palmer, III et al. | |
| 2012/0310155 A1 | 12/2012 | Heiser et al. | |
| 2013/0150714 A1 | 6/2013 | Howlett et al. | |
| 2013/0267850 A1 | 10/2013 | Berman | |
| 2013/0274778 A1 | 10/2013 | Mercier et al. | |
| 2013/0341849 A1 | 12/2013 | Shimazaki et al. | |
| 2013/0345671 A1 | 12/2013 | Ryu et al. | |
| 2013/0345855 A1 | 12/2013 | Tsai et al. | |
| 2014/0005606 A1 | 1/2014 | Chen et al. | |
| 2014/0120505 A1 | 5/2014 | Rios et al. | |
| 2014/0121636 A1 | 5/2014 | Boyden et al. | |
| 2014/0121637 A1 | 5/2014 | Boyden et al. | |
| 2014/0212864 A1 | 7/2014 | Rios et al. | |
| 2014/0261430 A1 | 9/2014 | Davis | |
| 2015/0027447 A1 | 1/2015 | Leevan et al. | |
| 2015/0055140 A1 | 2/2015 | Deguilio | |
| 2015/0157797 A1 | 6/2015 | Eggert et al. | |

OTHER PUBLICATIONS

Allemann, Inja Bogdan et al., "Hyaluronic acid gel (Juvéderm™) preparations in the treatment of facial wrinkles and folds", Clinical Interventions in Aging, 2008, pp. 629-634, vol. 4, Dove Medical Press Limited.

Bain, Michael et al., "A Triangular Pattern for Botox Forehead Rejuvenation", Aesthetic Surgery Journal, Sep./Oct. 2006, pp. 617-619, vol. 26, No. 5, The American Society for Aesthetic Plastic Surgery, Inc.

Bernardini, Fausto et al., "The 3D Model Acquisition Pipeline", Computer Graphics Forum, 2002, pp. 149-172, vol. 21 No. 2, The Eurographics Association and Blackwell Publishers Ltd.

Bevilacqua, Alessandro et al., "Measuring Skin Topographic Structures through Capacitance Image Analysis", Proceedings of the IEEE International Conference on Video and Signal Based Surveillance, 2006, pp. 1-5, IEEE.

Brandt, Fredric S. et al., "Hyaluronic acid gel fillers in the management of facial aging", Clinical Interventions in Aging, 2008, pp. 153-159, vol. 3, No. 1, Dove Medical Press Limited.

Buckley, Peter F. et al., "A Three-Dimensional Morphometric Study of Craniofacial Shape in Schizophrenia", Am J Psychiatry, Mar. 2005, pp. 606-608, vol. 162, No. 3.

Carruthers, Jean D. A. et al., "Advances in Facial Rejuvenation: Botulinum Toxin Type A, Hyaluronic Acid Dermal Fillers, and Combination Therapies—Consensus Recommendations", PRSJournal.com, 2008, pp. 5S-30S, The American Society of Plastic Surgeons.

Chawla, Vipul et al., "An Overview of Passive RFID" IEEE Applications & Practice, Sep. 2007, pp. 11-17, IEEE.

Feng, Zhihong et al., "Computer-assisted technique for the design and manufacture of realistic facial prostheses", British Journal of Oral and Maxillofacial Surgery, 2010, pp. 105-109, vol. 48, Elsevier Ltd.

Finkenzeller, Klaus, "RFID Handbook: Fundamentals and Applications in Contactless Smart Cards and Identification", 2003, pp. 29-59, John Wiley & Sons.

Hanke, William C. et al., "Facial Soft-Tissue Fillers conference: Assessing the State of the Science", Proceedings report. J Am Acad Dermatol, 2011, pp. S66-S85.e135, American Academy of Dermatology, Inc and American Society of Plastic Surgeons.

Hopenfeld, Bruce et al., "Geodesic Based Registration of Sensor Data and Anatomical Surface Image Data", NIH Public Access Author Manuscript, Oct. 2007, pp. 1-20, vol. 35, No. 10.

Jagadeesh, Gopalan et al., "Needleless Vaccine Delivery Using Micro-Shock Waves", Clinical and Vaccine Immunology, Apr. 2011, pp. 539-545, vol. 18, No. 4, American Society for Microbiology.

(56) References Cited

OTHER PUBLICATIONS

Kolb, Andreas et al., "Time-of-Flight Sensors in Computer Graphics" Computer Graphics Forum, Jun. 2009, pp. 1-16, No. Z.

Kundu, Suriti et al., "Principles of Office Anesthesia: Part II. Topical Anesthesia", American Family Physician, Jul. 1, 2002, pp. 99-102, vol. 66, No. 1.

Lapatki, Bernd G. et al., "Topographical Characteristics of Motor Units of the Lower Facial Musculature Revealed by Means of High-Density Surface EMG", J Neurophysiol, 2006, pp. 342-354, vol. 95, American Physiological Society.

Levenberg, Alex, "Clinical experience with a TriPollar™ radiofrequency system for facial and body aesthetic treatments", Eur J Dermatol, 2010, pp. 615-619, vol. 20, No. 5.

Majid, Z. et al., "Integration of Stereophotogrammetry and triangulation-based laser scanning system for precise mapping of craniofacial morphology", The International Archives of the Photogrammetry, Remote Sensing and Spatial Information Sciences, 2008, pp. 805-812, vol. 37, Part B5, Beijing.

Markiewicz, Michael R. et al., "The Use of 3D Imaging Tools in Facial Plastic Surgery", Facial Plast Surg Clin N Am, 2011, pp. 655-682, vol. 19, Elsevier Inc.

McCleane, Gary, "Topical application of analgesics: a clinical option in day case anaesthesia?", Curr Opin Anesthesiol, 2010, pp. 704-707, vol. 23, Wolters Kluwer Health and Lippincott Williams & Wilkins.

Meier, Jason D. et al., "Autologous Fat Grafting Long-term Evidence of Its Efficacy in Midfacial Rejuvenation", Arch Facial Plast Surg, Jan./Feb. 2009, pp. 24-28, vol. 11, No. 1, American Medical Association.

Park, Juwan et al., "Profile of Xeomin® (incobotulinumtoxinA) for the treatment of blepharospasm", Clinical Ophthalmology, 2011, pp. 725-732, vol. 5, Dove Medical Press Ltd.

Prager, Welf et al., "A prospective, rater-blind, randomized comparison of the effectiveness tolerability of Belotero® Basic versus Restylane® for correction of nasolabial folds", Eur J Dermatol, 2010, pp. 748-752, vol. 20, No. 6.

Sherman, Richard N., "Avoiding dermal filler complications", Clinics in Dermatology, 2009, pp. S23-S32, vol. 27, Elsevier Inc.

Sun, Chengzhi et al., "An Enhanced Active Shape Model for Facial Features Extraction", 11$^{th}$ IEEE International Conference on Communication Technology Proceedings, 2008, pp. 661-664, IEEE.

Szeliski, Richard, "Image Alignment and Stitching: A Tutorial", Foundations and Trends® in Computer Graphics and Vision, 2006, pp. 1-104, vol. 2, No. 1, R. Szeliski.

Van Heerbeek, Niels et al., "Three dimensional measurement of rhinoplasty results", Rhinology, 2009, pp. 121-125, vol. 47.

Wieringa, F. P. et al., "Remote Non-invasive Stereoscopic Imaging of Blood Vessels: First In-vivo Results of a New Multispectral Contrast Enhancement Technology", Annals of Biomedical Engineering, Dec. 2006, pp. 1870-1878, vol. 34, No. 12, Biomedical Engineering Society.

Wolff, Erin et al., "Skin wrinkles and rigidity in early postmenopausal women vary by race/ethnicity: baseline characteristics of the skin ancillary study of the keeps trial", Fertil Steril, Feb. 2011, pp. 1-12, vol. 95 No. 2.

Zheng, Zhong-Long et al., "Enhanced active shape model for facial feature localization", Proceedings of the Seventh International Conference on Machine Learning and Cybernetics, Jul. 12-15, 2008, pp. 2841-2845, IEEE.

Zitová, Barbara et al., "Image registration methods: a survey", Image and Vision Computing, 2003, pp. 977-1000, vol. 21, Elsevier B.V.

PCT International Search Report; International App. No. PCT/US2013/053604; Feb. 21, 2014; pp. 1-4.

PCT International Search Report; International App. No. PCT/US2013/067029; Mar. 18, 2014; pp. 1-2.

European Patent Office, extended European Search Report, Pursuant to Rule 62 EPC; App. No. EP 13828529.1; May 2, 2016; pp. 1-6.

* cited by examiner

FIG. 11A
FIG. 11B
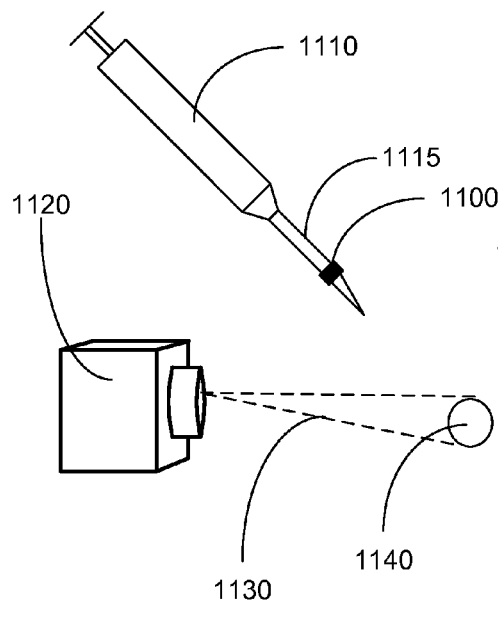
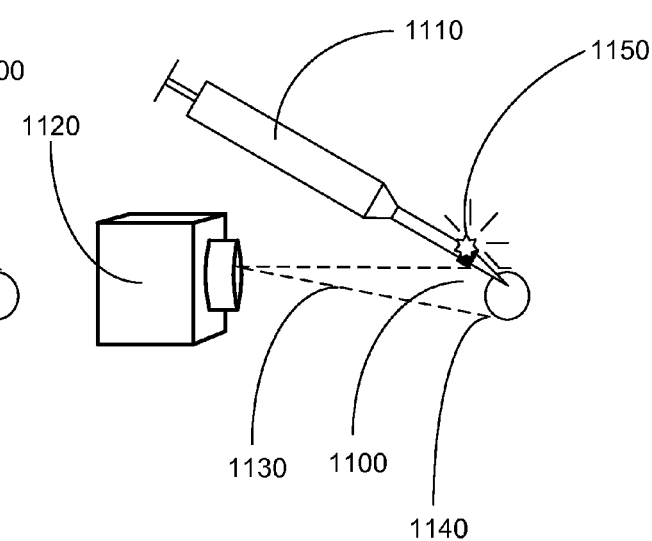

FIG. 13

1200
Illuminating one or more injection sites in an injection-treatment pattern on a surface of a body region of the individual in accordance with an injection-treatment plan > 1300
> Illuminating the one or more injection sites on the surface of a face, torso, abdomen, head, neck, upper extremity, lower extremity, or buttocks region of the individual > 1310
> Illuminating the one or more injection sites on the surface of the body region of the individual with one or more controllable light emitting elements configured to emit non-destructive light
>
>> 1320
>> Wherein the one or more controllable light emitting elements configured to emit non-destructive light comprise one or more of a controllable light emitting diode, laser, laser diode, collimated light source, projector, or focused light source configured to emit non-destructive light > 1330
> Illuminating the one or more injection sites on the surface of the body region of the individual with one or more controllable light emitting elements mounted on a head region of a user, the one or more controllable light emitting elements configured to emit non-destructive light > 1340
> Autonomously illuminating the one or more injection sites in the injection-treatment pattern using a computing device operably connected to one or more controllable light emitting elements, the computing device accessing a stored injection-treatment plan and controlling illumination from the one or more controllable light emitting elements to illuminate the one or more injection sites on the surface of the body region of the individual in accordance with the stored injection-treatment plan

1210
Injecting at least one injectable agent into an underlying tissue of the body region at or near at least one of the one or more illuminated injection sites

FIG. 14

1200
Illuminating one or more injection sites in an injection-treatment pattern on a surface of a body region of the individual in accordance with an injection-treatment plan > 1400
> Illuminating the one or more injection sites on the surface of the body region of the individual with one or more of a color or a pattern of light
>
>> 1410
>> Illuminating the one or more injection sites on the surface of the body region of the individual with one or more of a crosshair, circle, or concentric circles
>
>> 1420
>> Illuminating the one or more injection sites on the surface of the body region of the individual with one or more of a letter, number, shape, or symbol
>
>> 1430
>> Wherein the one or more of the color or pattern of light is representative of at least one injection-treatment parameter
>>
>>> 1440
>>> Wherein the at least one injection-treatment parameter comprises at least one of an injection site, a type of injectable agent, a type of injector, a dosage of an injectable agent, a sequence of dosing an injectable agent, a timing of dosing an injectable agent, an injection depth, or an injection angle

1210
Injecting at least one injectable agent into an underlying tissue of the body region at or near at least one of the one or more illuminated injection sites

FIG. 18

1200
Illuminating one or more injection sites in an injection-treatment pattern on a surface of a body region of the individual in accordance with an injection-treatment plan

1210
Injecting at least one injectable agent into an underlying tissue of the body region at or near at least one of the one or more illuminated injection sites

1800
Wherein injecting at least one injectable agent into the underlying tissue of the body region at or near at least one of the one or more illuminated injection sites comprises injecting at least one neurotoxin

1810
Wherein injecting at least one injectable agent into the underlying tissue of the body region at or near at least one of the one or more illuminated injection sites comprises injecting at least one of a subcutaneous volume enhancer or a dermal filler

1820
Injecting at least one of a collagen filler

1830
Injecting at least one of a hyaluronic acid filler

1840
Injecting at least one of adipose, fibroblasts, calcium microspheres, or poly L lactic acid

1850
Wherein injecting at least one injectable agent into the underlying tissue of the body region at or near at least one of the one or more illuminated injection sites comprises injecting at least one of insulin, antibiotic, hormone, chemotherapeutic, cells, anti-inflammatory agent, or biological agent

FIG. 21

2100
Receiving one or more digital images of a body region of an individual, the body region including one or more physical registration landmarks

2110
Generating at least one digital representation of the body region using the one or more digital images, the at least one digital representation including one or more digital registration landmarks corresponding to the one or more physical registration landmarks on the body region

2120
Adding one or more digitally registered injection sites to the at least one digital representation of the body region in an injection-treatment pattern, the one or more digitally registered injection sites registered relative to the one or more digital registration landmarks

2130
Generating one or more output signals having information for controlling one or more controllable light-emitting elements to illuminate a location on a surface of the body region of the individual corresponding in location to at least one of the one or more digitally registered injection sites

FIG. 22

2100
Receiving one or more digital images of a body region of an individual, the body region including one or more physical registration landmarks > 2200
> Receiving the one or more digital images of the body region from a data storage device > 2210
> Receiving the one or more digital images of the body region from one or more of a camera, active scanner, or passive scanner > 2220
> Receiving the one or more digital images of the body region from one or more of an ultrasound device, a photoacoustic device, a thermal imaging device, a non-contact scanning device, a contact scanning device, a magnetic resonance imaging device, a computed tomography device, a capacitance measuring device, or other biomedical imaging device > 2230
> Receiving the one or more digital images of the body region through one or more wireless transmissions

2110
Generating at least one digital representation of the body region using the one or more digital images, the at least one digital representation including one or more digital registration landmarks corresponding to the one or more physical registration landmarks on the body region

2120
Adding one or more digitally registered injection sites to the at least one digital representation of the body region in an injection-treatment pattern, the one or more digitally registered injection sites registered relative to the one or more digital registration landmarks

2130
Generating one or more output signals having information for controlling one or more controllable light-emitting elements to illuminate a location on a surface of the body region of the individual corresponding in location to at least one of the one or more digitally registered injection sites

FIG. 23

| 2100 |
| --- |
| Receiving one or more digital images of a body region of an individual, the body region including one or more physical registration landmarks |

| 2110 |
| --- |
| Generating at least one digital representation of the body region using the one or more digital images, the at least one digital representation including one or more digital registration landmarks corresponding to the one or more physical registration landmarks on the body region |

| 2300 | 2310 |
| --- | --- |
| Generating the at least one digital representation of the body region by overlaying the one or more digital images of the body region | Generating a three-dimensional digital model of the body region using the one or more digital images and at least one three-dimensional modeling algorithm |

| 2320 |
| --- |
| Generating an injection-treatment plan based on analysis of the at least one digital representation of the body region |

| 2330 | 2340 | 2350 |
| --- | --- | --- |
| Identifying an area of the body region in need of treatment by comparison of the at least one digital representation of the body region with at least one stored representation of at least one comparable body region | Wherein the injection-treatment plan comprises one or more injections of at least one injectable agent arranged in an injection-treatment pattern specific for the individual | Wherein the injection-treatment plan comprises one or more injections of at least one injectable agent arranged in an injection-treatment pattern specific for a condition being treated |

| 2360 |
| --- |
| Wherein the injection-treatment plan comprises at least one of one or more injection sites, a pattern of injection sites, a type of injectable agent, a type of injector, a dosage of an injectable agent, an injection sequence, an injection timing, an injection depth, or an injection angle |

| 2120 |
| --- |
| Adding one or more digitally registered injection sites to the at least one digital representation of the body region in an injection-treatment pattern, the one or more digitally registered injection sites registered relative to the one or more digital registration landmarks |

| 2130 |
| --- |
| Generating one or more output signals having information for controlling one or more controllable light-emitting elements to illuminate a location on a surface of the body region of the individual corresponding in location to at least one of the one or more digitally registered injection sites |

2100
Receiving one or more digital images of a body region of an individual, the body region including one or more physical registration landmarks 2110
Generating at least one digital representation of the body region using the one or more digital images, the at least one digital representation including one or more digital registration landmarks corresponding to the one or more physical registration landmarks on the body region 2120
Adding one or more digitally registered injection sites to the at least one digital representation of the body region in an injection-treatment pattern, the one or more digitally registered injection sites registered relative to the one or more digital registration landmarks > 2400
> Adding the one or more digitally registered injection sites automatically based on a computed injection-treatment plan > 2410
> Adding the one or more digitally registered injection sites with a user input device > 2420
> Adding one or more of a dot, crosshair, circle, or concentric circles representative of the one or more digitally registered injection sites to the at least one digital representation of the body region > 2430
> Adding one or more of a letter, number, shape, symbol, color, or combination thereof representative of the one or more digitally registered injection sites to the at least one digital representation of the body region
>
>> 2440
>> Wherein the one or more of a letter, number, shape, symbol, color, or combination thereof are representative of at least one treatment parameter
>>
>>> 2450
>>> One or more of a letter, number, shape, symbol, color, or combination thereof representative of at least one of an injection site, a type of injectable agent, a type of injector, a dosage of an injectable agent, a sequence of injecting an injectable agent, a timing of injecting an injectable agent, an injection depth, or an injection angle 2130
Generating one or more output signals having information for controlling one or more controllable light-emitting elements to illuminate a location on a surface of the body region of the individual corresponding in location to at least one of the one or more digitally registered injection sites

FIG. 25

2100
Receiving one or more digital images of a body region of an individual, the body region including one or more physical registration landmarks

2110
Generating at least one digital representation of the body region using the one or more digital images, the at least one digital representation including one or more digital registration landmarks corresponding to the one or more physical registration landmarks on the body region

2120
Adding one or more digitally registered injection sites to the at least one digital representation of the body region in an injection-treatment pattern, the one or more digitally registered injection sites registered relative to the one or more digital registration landmarks

2130
Generating one or more output signals having information for controlling one or more controllable light-emitting elements to illuminate a location on a surface of the body region of the individual corresponding in location to at least one of the one or more digitally registered injection sites 2500
Generating one or more output signals having information for controlling one or more of a controllable projector, light emitting diode, laser, laser diode, collimated light source, or focused light source 2510
Generating one or more output signals having information for controlling the one or more controllable light-emitting elements to illuminate a location on the surface of the body region of the individual with one or more spots, crosshairs, circles, or concentric circles corresponding in location to at least one of the one or more digitally registered injection sites 2520
Generating one or more output signals having information for controlling the one or more controllable light-emitting elements to illuminate a location on the surface of the body region of the individual with one or more of a letter, number, shape, symbol, color, or combination thereof corresponding in location to at least one of the one or more digitally registered injection sites

FIG. 26

2100
Receiving one or more digital images of a body region of an individual, the body region including one or more physical registration landmarks

2110
Generating at least one digital representation of the body region using the one or more digital images, the at least one digital representation including one or more digital registration landmarks corresponding to the one or more physical registration landmarks on the body region

2120
Adding one or more digitally registered injection sites to the at least one digital representation of the body region in an injection-treatment pattern, the one or more digitally registered injection sites registered relative to the one or more digital registration landmarks

2130
Generating one or more output signals having information for controlling one or more controllable light-emitting elements to illuminate a location on a surface of the body region of the individual corresponding in location to at least one of the one or more digitally registered injection sites

2600
Generating one or more output signals having information for controlling the one or more controllable light-emitting elements to illuminate the location on the surface of the body region of the individual corresponding in location to the at least one of the one or more digitally registered injection sites in accordance with an injection-treatment plan

2610
Generating one or more output signals having information for controlling the one or more controllable light-emitting elements to sequentially illuminate one or more locations on the surface of the body region of the individual corresponding in location to one or more digitally registered injection sites in accordance with an injection-treatment plan

2620
Generating one or more output signals having information for controlling the one or more controllable light-emitting elements to sequentially illuminate the one or more locations on the surface of the body region of the individual based on accurate completion of an injection at a previously illuminated injection site

FIG. 27

2100
Receiving one or more digital images of a body region of an individual, the body region including one or more physical registration landmarks

2110
Generating at least one digital representation of the body region using the one or more digital images, the at least one digital representation including one or more digital registration landmarks corresponding to the one or more physical registration landmarks on the body region

2120
Adding one or more digitally registered injection sites to the at least one digital representation of the body region in an injection-treatment pattern, the one or more digitally registered injection sites registered relative to the one or more digital registration landmarks

2130
Generating one or more output signals having information for controlling one or more controllable light-emitting elements to illuminate a location on a surface of the body region of the individual corresponding in location to at least one of the one or more digitally registered injection sites

2700
Generating one or more output signals having information for projecting one or more annotations on the surface of the body region of the individual at or near one or more illuminated injection sites

2710
Generating one or more output signals having information for adjusting the one or more controllable light-emitting elements so at to align one or more illuminated injection sites relative to the one or more physical registration landmarks on the body region of the individual to substantially correspond to the at least one digital representation of the body region

FIG. 28

| 2100
Receiving one or more digital images of a body region of an individual, the body region including one or more physical registration landmarks |

| 2110
Generating at least one digital representation of the body region using the one or more digital images, the at least one digital representation including one or more digital registration landmarks corresponding to the one or more physical registration landmarks on the body region |

| 2120
Adding one or more digitally registered injection sites to the at least one digital representation of the body region in an injection-treatment pattern, the one or more digitally registered injection sites registered relative to the one or more digital registration landmarks |

| 2130
Generating one or more output signals having information for controlling one or more controllable light-emitting elements to illuminate a location on a surface of the body region of the individual corresponding in location to at least one of the one or more digitally registered injection sites |

| 2800
Receiving in real-time one or more second digital images of the body region of the individual including the one or more physical registration landmarks and the one or more illuminated injection sites on the surface of the body region; and
generating one or more output signals having information for adjusting the one or more controllable light-emitting elements so as to align the one or more illuminated injection sites relative to the one or more physical registration landmarks on the body region to substantially correspond to the at least one digital representation of the body region. |

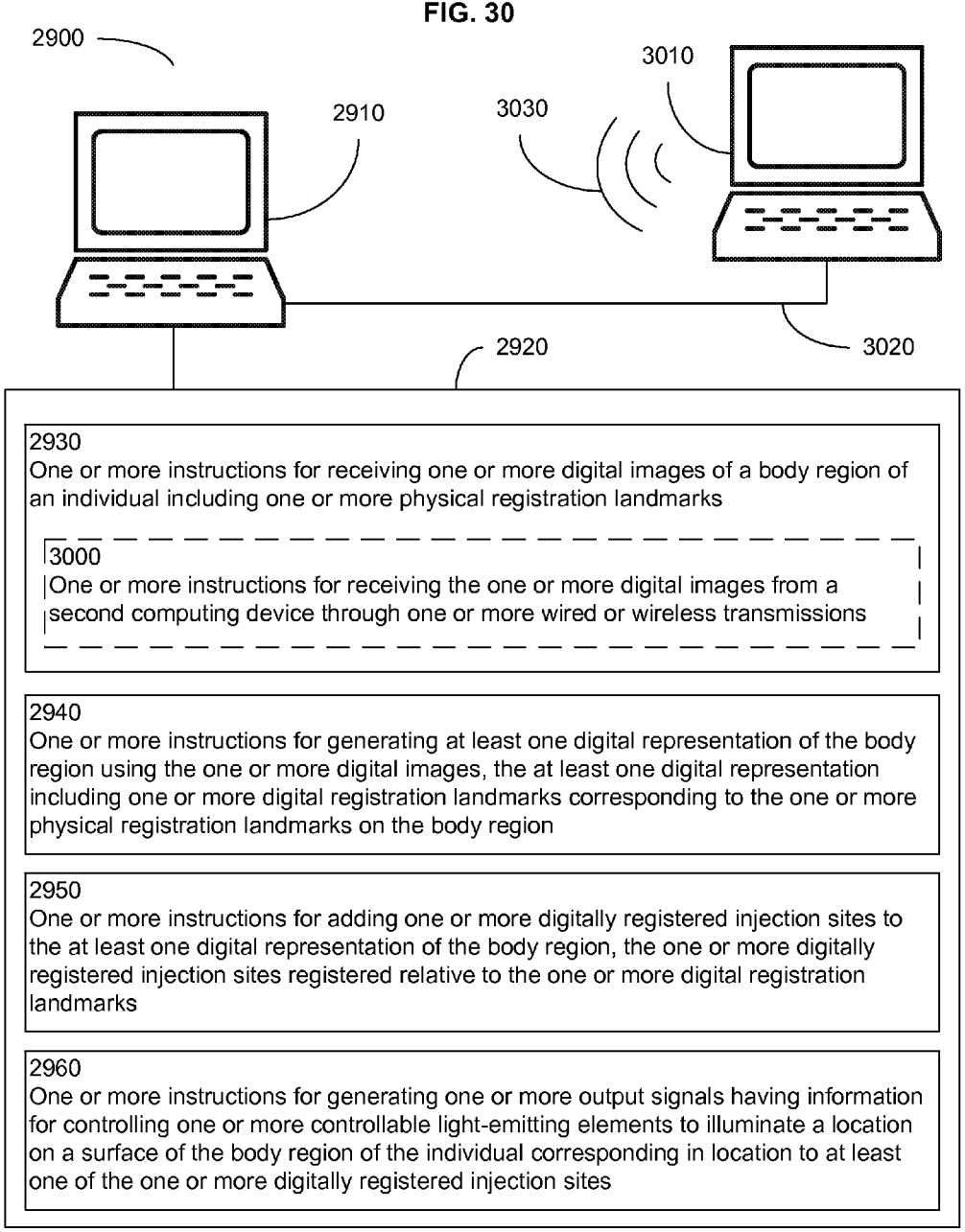

FIG. 31

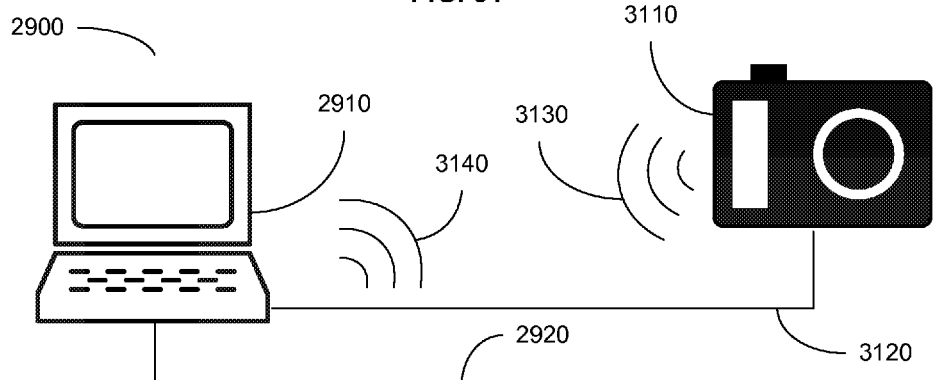

| 2930 One or more instructions for receiving one or more digital images of a body region of an individual including one or more physical registration landmarks |
|---|
| 3100 One or more instructions for receiving the one or more digital images from at least one image capture device through one or more wired or wireless transmission |
| 3150 One or more instructions for controlling one or more functions of the at least one image capture device |
| 3160 One or more instructions for controlling acquisition of the one or more digital images of the body region of the individual with the at least one image capture device |
| 3170 One or more instructions for controlling one or more of an on/off function, positioning function, scanning rate function, exposure function, or energy emission function of the at least one image capture device |

| 2940 One or more instructions for generating at least one digital representation of the body region using the one or more digital images, the at least one digital representation including one or more digital registration landmarks corresponding to the one or more physical registration landmarks on the body region | 2950 One or more instructions for adding one or more digitally registered injection sites to the at least one digital representation of the body region, the one or more digitally registered injection sites registered relative to the one or more digital registration landmarks | 2960 One or more instructions for generating one or more output signals having information for controlling one or more controllable light-emitting elements to illuminate a location on a surface of the body region of the individual corresponding in location to at least one of the one or more digitally registered injection sites |

FIG. 33

| 2930<br>One or more instructions for receiving one or more digital images of a body region of an individual including one or more physical registration landmarks |
|---|
| 2940<br>One or more instructions for generating at least one digital representation of the body region using the one or more digital images, the at least one digital representation including one or more digital registration landmarks corresponding to the one or more physical registration landmarks on the body region |
| 2950<br>One or more instructions for adding one or more digitally registered injection sites to the at least one digital representation of the body region, the one or more digitally registered injection sites registered relative to the one or more digital registration landmarks |
| 3300<br>One or more instructions for adding the one or more digitally registered injection sites to the at least one digital representation of the body region in an injection-treatment pattern as part of an injection-treatment plan |
| 3310<br>One or more instructions for automatically adding the one or more digitally registered injection sites to the at least one digital representation of the body region |
| 3320<br>One or more instructions for adding the one or more digitally registered injection sites to the at least one digital representation of the body region using a user input device |
| 3330<br>One or more instructions for adding one or more colors, letters, numbers, shapes, symbols, or combinations thereof representative of the one or more digitally registered injection sites to the at least one digital representation of the body region |
| 2960<br>One or more instructions for generating one or more output signals having information for controlling one or more controllable light-emitting elements to illuminate a location on a surface of the body region of the individual corresponding in location to at least one of the one or more digitally registered injection sites |

FIG. 34

| 2930 |
| --- |
| One or more instructions for receiving one or more digital images of a body region of an individual including one or more physical registration landmarks |

| 2940 |
| --- |
| One or more instructions for generating at least one digital representation of the body region using the one or more digital images, the at least one digital representation including one or more digital registration landmarks corresponding to the one or more physical registration landmarks on the body region |

| 2950 |
| --- |
| One or more instructions for adding one or more digitally registered injection sites to the at least one digital representation of the body region, the one or more digitally registered injection sites registered relative to the one or more digital registration landmarks |

| 2960 |
| --- |
| One or more instructions for generating one or more output signals having information for controlling one or more controllable light-emitting elements to illuminate a location on a surface of the body region of the individual corresponding in location to at least one of the one or more digitally registered injection sites |
| 3400 One or more instructions for generating one or more output signals having information for controlling one or more of an on/off function, focus, intensity, position, color of light emitted, pattern of light emitted, sequencing, or timing of the one or more controllable light emitting elements |
| 3410 One or more instruction for generating one or more output signals having information for controlling the one or more controllable light-emitting elements to illuminate one or more locations on the surface of the body region of the individual in a temporal sequence in accordance with an injection-treatment plan, the one or more locations corresponding to the one or more digitally registered injection sites |

| 3420 One or more instructions for generating one or more output signals having information for controlling the one or more controllable light-emitting elements to project one or more annotations onto the surface of the body region of the individual |
| --- |

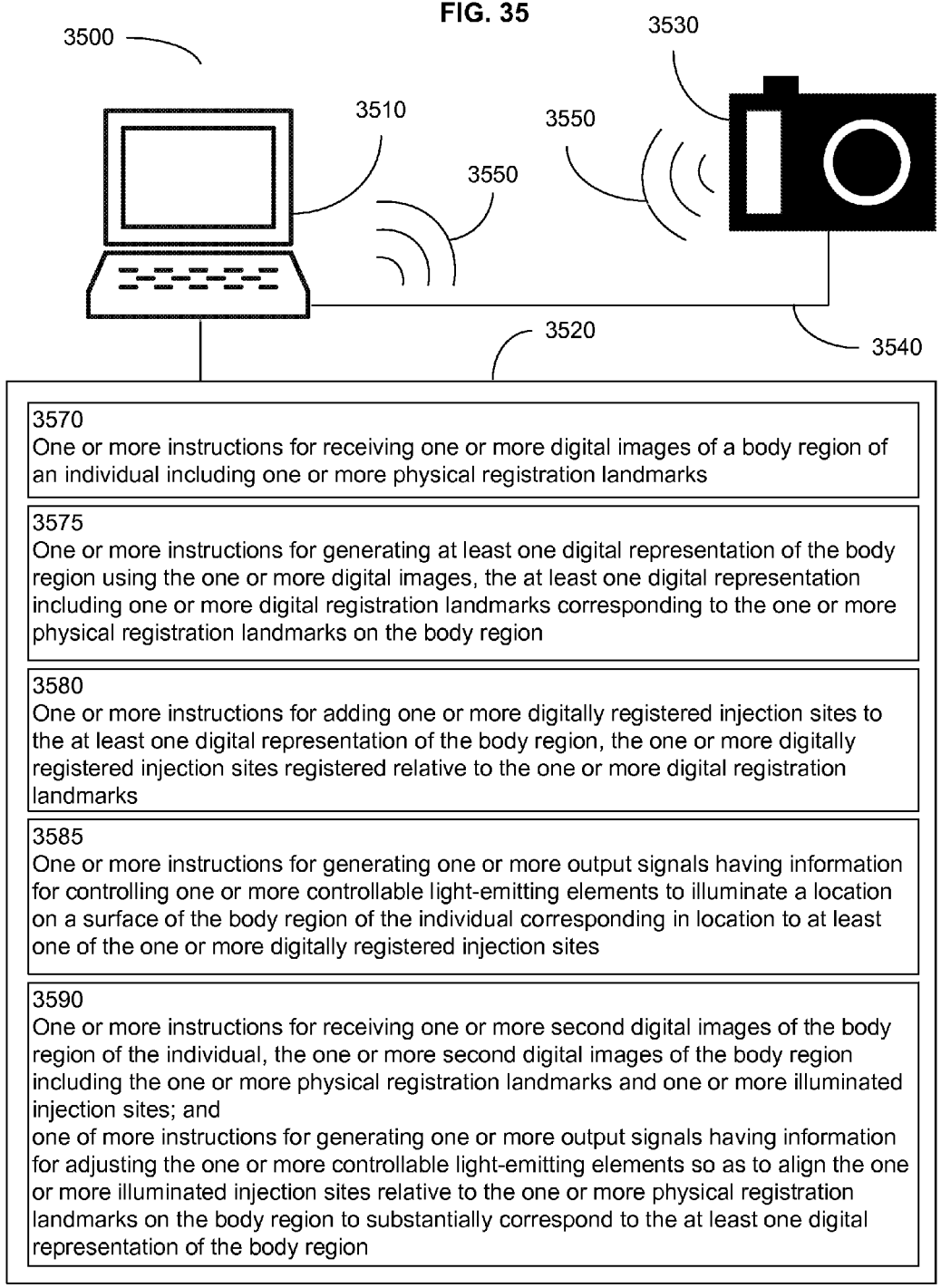

FIG. 36

3600 An article of manufacture

3610
Non-transitory signal-bearing medium bearing one or more instructions for generating an injection guide, the non-statutory signal-bearing medium including:

3620
One or more instructions for receiving one or more digital images of a body region of an individual including one or more physical registration landmarks

3630
One or more instructions for generating at least one digital representation of the body region using the one or more digital images, the at least one digital representation including one or more digital registration landmarks corresponding to the one or more physical registration landmarks on the body region

3640
One or more instructions for adding one or more digitally registered injection sites to the at least one digital representation of the body region, the one or more digitally registered injection sites registered relative to the one or more digital registration landmarks

3650
One or more instructions for generating one or more output signals having information for controlling one or more controllable light-emitting elements to illuminate a location on a surface of the body region of the individual corresponding in location to at least one of the one or more digitally registered injection sites

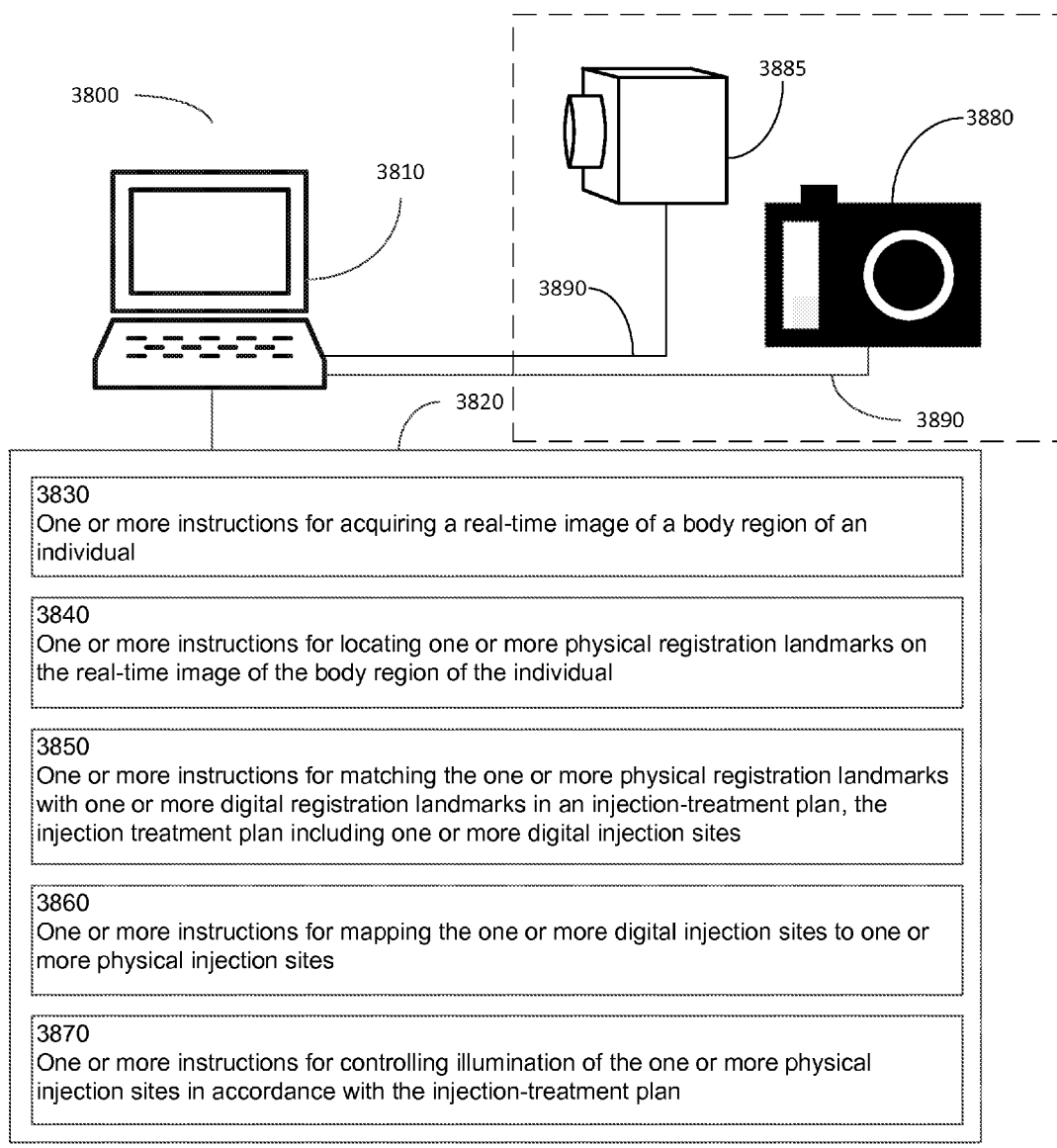

SYSTEMS AND METHODS FOR GUIDING INJECTIONS

CROSS-REFERENCE TO RELATED APPLICATIONS

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

Priority Applications:
  None.
Related Applications:
  U.S. patent application Ser. No. 13/664,273, entitled SYSTEMS AND METHODS FOR GENERATING AN INJECTION GUIDE, naming Edward S. Boyden, Gregory J. Della Rocca, Daniel Hawkins, Roderick A. Hyde, Robert Langer, Eric C. Leuthardt, Terence Myckatyn, Parag Jitendra Parikh, Dennis J. Rivet, Joshua S. Shimony, Michael A. Smith, and Clarence T. Tegreene as inventors, filed 30 Oct. 2012 is related to the present application.
  U.S. patent application Ser. No. 13/567,921, entitled DEVICES AND METHODS FOR WEARABLE INJECTION GUIDES, naming Mahalaxmi Gita Bangera, Edward S. Boyden, Hon Wah Chin, Gregory J. Della Rocca, Daniel Hawkins, Roderick A. Hyde, Muriel Y. Ishikawa, Jordin T. Kare, Robert Langer, Eric C. Leuthardt, Stephen L. Malaska, Terence Myckatyn, Parag Jitendra Parikh, Dennis J. Rivet, Joshua S. Shimony, Michael A. Smith, Elizabeth A. Sweeney, Clarence T. Tegreene, Sharon L. Wolda, and Lowell L. Wood, Jr. as inventors, filed 6 Aug. 2012 is related to the present application.
  U.S. patent application Ser. No. 13/567,995, entitled DEVICES AND METHODS FOR WEARABLE INJECTION GUIDES, naming Mahalaxmi Gita Bangera, Edward S. Boyden, Hon Wah Chin, Gregory J. Della Rocca, Daniel Hawkins, Roderick A. Hyde, Muriel Y. Ishikawa, Jordin T. Kare, Robert Langer, Eric C. Leuthardt, Stephen L. Malaska, Terence Myckatyn, Parag Jitendra Parikh, Dennis J. Rivet, Joshua S. Shimony, Michael A. Smith, Elizabeth A. Sweeney, Clarence T. Tegreene, Sharon L. Wolda, and Lowell L. Wood, Jr. as inventors, filed 6 Aug. 2012 is related to the present application.
  U.S. patent application Ser. No. 13/568,033, entitled SYSTEMS AND METHODS FOR WEARABLE INJECTION GUIDES, naming Mahalaxmi Gita Bangera, Edward S. Boyden, Hon Wah Chin, Gregory J. Della Rocca, Daniel Hawkins, Roderick A. Hyde, Muriel Y. Ishikawa, Jordin T. Kare, Robert Langer, Eric C. Leuthardt, Stephen L. Malaska, Terence Myckatyn, Parag Jitendra Parikh, Dennis J. Rivet, Joshua S. Shimony, Michael A. Smith, Elizabeth A. Sweeney, Clarence T. Tegreene, Sharon L. Wolda, and Lowell L. Wood, Jr. as inventors, filed 6 Aug. 2012 is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

To the extent that the listings of applications provided above may be inconsistent with the listings provided via an ADS, it is the intent of the application to claim priority to all applications listed in the Priority Applications section of either document.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, a system for guiding injection in an individual includes, but is not limited to: one or more controllable light-emitting elements configured to emit non-destructive light; and a computing device operably connected to the one or more controllable light-emitting elements configured to emit non-destructive light, the computing device including a processor operable to receive at least one digital representation of a body region of the individual, the body region of the individual including one or more physical registration landmarks, the at least one digital representation including one or more digitally registered injection sites and one or more digital registration landmarks corresponding to the one or more physical registration landmarks on the body region; and control the one or more controllable light-emitting elements to illuminate a location on a surface of the body region of the individual corresponding in location to at least one of the one or more digitally registered injection sites. In addition to the foregoing, other system aspects are described in the claims, drawings, and text forming a part of the present disclosure.

In an aspect, a method for guiding injection in an individual includes, but is not limited to: illuminating one or more injection sites in an injection-treatment pattern on a surface of a body region of the individual in accordance with an injection-treatment plan; and injecting at least one injectable agent into an underlying tissue of the body region at or near at least one of the one or more illuminated injection sites. In addition to the foregoing, other method aspects are described in the claims, drawings, and text forming a part of the present disclosure.

In an aspect, a method for guiding injection in an individual includes, but is not limited to: projecting an injection-treatment pattern on a surface of a body region of the individual, the injection-treatment pattern part of a digitally-rendered injection-treatment plan and including one or more illuminated injection sites; placing one or more marks on the surface of the body region of the individual, the one or more mark substantially corresponding in location to the one or more illuminated injection sites; and injecting at least one injectable agent into an underlying tissue of the body region of the individual at or near at least one of the one or more marks. In addition to the foregoing, other method aspects are described in the claims, drawings, and text forming a part of the present disclosure.

In an aspect, a system includes, but is not limited to: a computer processor; and non-transitory signal-bearing medium bearing one or more instruction for registering illuminated injection sites, the non-transitory signal-bearing medium including one or more instructions for acquiring a real-time image of a body region of an individual; one or more instructions for locating one or more physical registration landmarks on the real-time image of the body region of the individual; one or more instructions for matching the one or more physical registration landmarks with one or more digital registration landmarks in an injection-treatment plan, the injection treatment plan including one or more digital injection sites; one or more instructions for mapping the one or more digital injection sites to one or more physical injection sites; and one or more instructions for controlling illumination of the one or more physical injection sites. In addition to the foregoing, other system aspects are described in the claims, drawings, and text forming a part of the present disclosure.

In an aspect, an article of manufacture includes, but is not limited to: non-transitory signal-bearing medium bearing one or more instructions for guiding injection in an individual, the non-transitory signal-bearing medium including one or more instructions including one or more instructions for referencing one or more digitally registered sites on a three-dimensional model of a body region of the individual with one or more digital injection sites; and one or more instructions for controlling illumination of injection information for each digital injection site onto a surface of the body region of the individual. In addition to the foregoing, other article of manufacture aspects are described in the claims, drawings, and text forming a part of the present disclosure.

In an aspect, a method implemented on a computing device for generating an injection guide includes, but is not limited to: receiving one or more digital images of a body region of an individual, the body region including one or more physical registration landmarks; generating at least one digital representation of the body region using the one or more digital images, the at least one digital representation including one or more digital registration landmarks corresponding to the one or more physical registration landmarks on the body region; adding one or more digitally registered injection sites to the at least one digital representation of the body region in an injection-treatment pattern, the one or more digitally registered injection sites registered relative to the one or more digital registration landmarks; and generating one or more output signals having information for controlling one or more controllable light-emitting elements to illuminate a location on a surface of the body region of the individual corresponding in location to at least one of the one or more digitally registered injection sites. In addition to the foregoing, other method aspects are described in the claims, drawings, and text forming a part of the present disclosure.

In an aspect, a system includes, but is not limited to: a computer processor; and non-transitory signal-bearing medium bearing one or more instructions for generating an injection guide, the non-transitory signal-bearing medium including one or more instructions for receiving one or more digital images of a body region of an individual including one or more physical registration landmarks; one or more instructions for generating at least on digital representation of the body region using the one or more digital images, the at least one digital representation including one or more digital registration landmarks corresponding to the one or more physical registration landmarks on the body region; one or more instructions for adding one or more digitally registered injection sites to the at least one digital representation of the body region, the one or more digitally registered injection sites registered relative to the one or more digital registration landmarks; and one or more instructions for generating one or more output signals having information for controlling one or more controllable light-emitting elements to illuminate a location on a surface of the body region of the individual corresponding in location to at least one of the one or more digitally registered injection sites. In addition to the foregoing, other system aspects are described in the claims, drawings, and text forming a part of the present disclosure.

In an aspect, an article of manufacture includes, but is not limited to: non-transitory signal-bearing medium bearing one or more instructions for generating an injection guide, the non-transitory signal-bearing medium including one or more instructions for receiving one or more digital images of a body region of an individual including one or more physical registration landmarks; one or more instructions for generating at least one digital representation of the body region using the one or more digital images, the at least one digital representation including one or more digital registration landmarks corresponding to the one or more physical registration landmarks on the body region; one or more instructions for adding one or more digitally registered injection sites to the at least one digital representation of the body region, the one or more digitally registered injection sites registered relative to the one or more digital registration landmarks; and one or more instructions for generating one or more output signals having information for controlling one or more controllable light-emitting elements to illuminate a location on a surface of the body region of the individual corresponding in location to at least one of the one or more digitally registered injection sites. In addition to the foregoing, other article of manufacture aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 11A & 11B are schematics of an embodiment of an injector-tracking device.

FIG. 13 is a flowchart illustrating aspects of a method such as shown in FIG. 12.

FIG. 14 is a flowchart showing aspects of a method such as depicted in FIG. 12.

FIG. 18 is a flowchart depicting aspects of a method such as illustrated in FIG. 12.

FIG. 21 is a flowchart of a method for generating an injection guide.

FIG. 22 is a flowchart illustrating aspects of a method such as shown in FIG. 21.

FIG. 23 is a flowchart showing aspects of a method such as depicted in FIG. 21.

FIG. 24 is a flowchart depicting aspects of a method such as illustrated in FIG. 21.

FIG. 25 is a flowchart illustrating aspects of a method such as shown in FIG. 21.

FIG. 26 is a flowchart showing aspects of a method such as depicted in FIG. 21.

FIG. 27 is a flowchart depicting aspects of a method such as illustrated in FIG. 21.

FIG. 28 is a flowchart illustrating aspects of a method such as shown in FIG. 21.

FIG. 30 is a schematic of an embodiment of a system such as shown in FIG. 29.

FIG. 31 is a schematic of an embodiment of a system such as shown in FIG. 29.

FIG. 33 is a schematic of an embodiment of a system such as shown in FIG. 29.

FIG. 34 is a schematic of an embodiment of a system such as shown in FIG. 29.

FIG. 35 is a schematic of an embodiment of a system for generating an injection guide.

FIG. 36 is a schematic of an article of manufacture.

FIG. 38 is a schematic of a method for guiding injection in an individual.

DETAILED DESCRIPTION

Figure 1:
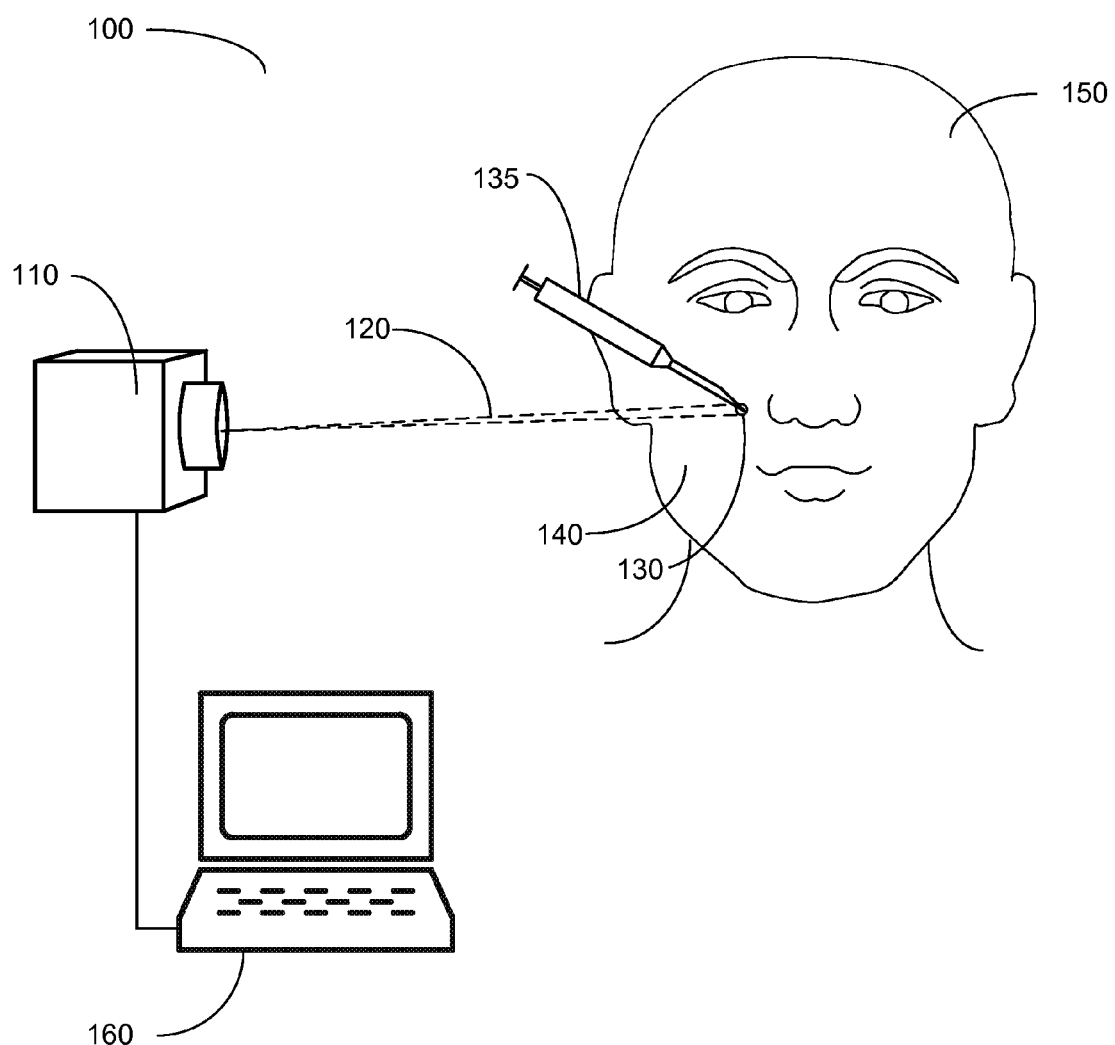
FIG. 1 is a schematic of an embodiment of a system for guiding injection in an individual.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here.

Systems and methods are described for generating and using illuminated injections guides on a surface of a body region of an individual. The injection guides can be used to guide injection of at least one injectable agent into a body region of an individual for treatment of one or more conditions. The systems and methods for generating and using the injection guides can be configured for use on any of a number of body regions of an individual including but not limited to the face, torso, abdomen, head, neck, upper extremity, lower, extremity, buttocks, or any other body region assessable for needle injection. The systems and methods for generating and using the injection guides can be used for guiding injection of injectable agents used to treat any of a number of conditions including but not limited to a cosmetic condition (e.g., wrinkles, sagging skin), pain (e.g., migraine), neurological disorder (e.g., idiopathic neuropathy), neuromuscular disorder (e.g., cervical dystonia, blepharospasm), inflammation (e.g., arthritis, psoriasis), vascular disorder (e.g., varicose veins, rosacea, Reynaud's Syndrome), cancer, infection (e.g., bacterial or viral infection), endocrine condition, metabolic condition (e.g., diabetes), infertility (e.g., ovulatory stimulation for in vitro fertilization), or vitamin deficiency (e.g., vitamin B deficiency). The at least one injectable agent can include any of a number of injectable agents including but not limited to neurotoxins, subcutaneous volume enhancers, dermal fillers, insulin, antibiotics, hormones, anti-inflammatory agents, chemotherapeutic agents, or biological agents.

In an embodiment, a system for guiding injection in an individual includes one or more controllable light-emitting elements configured to emit non-destructive light; and a computing device operably connected to the one or more controllable light-emitting elements configured to emit nondestructive light, the computing device including a processor operable to receive at least one digital representation of a body region of an individual, the body region of the individual including one or more physical registration landmarks, the at least one digital representation including one or more digitally registered injection sites and one or more digital registration landmarks corresponding to the one or more physical registration landmarks on the body region; and control the one or more controllable light-emitting elements to illuminate a location on a surface of the body region of the individual corresponding in location to at least one of the one or more digitally registered injection sites.

With reference to FIG. 1, shown is a schematic view of an embodiment of a system for guiding injection in an individual. System 100 of FIG. 1 includes controllable light-emitting element 110 emitting light 120 onto the surface of body region 140 of individual 150 to illuminate injection site 130. Illuminated injection site 130 on body region 140 of individual 150 is a target for injection of an injectable agent with injector 135. System 100 further includes computing device 160. Computing device 160 is operable to receive one or more digital representations of body region 140 of an individual 150, including one or more physical registration landmarks. The one or more digital representations include one or more digitally registered injection sites. Computing device 160 is further operable to control controllable light-emitting element 110 to emit light 120 on the surface of body region 140 of individual 150 corresponding in location to at least one of the one or more digitally registered injection sites.

System 100 includes one or more controllable light-emitting elements configured to emit non-destructive light, e.g., light of a wavelength, intensity, and/or energy that is non-destructive and/or non-damaging to cells and/or tissue of a body region, including the eyes. In general, light radiation, e.g., laser radiation, is categorized by the United States Food and Drug Administration (FDA) as follows: class I levels of laser radiation are considered non-hazardous, although hazard increases with optical aids, including magnifiers, binoculars, or telescopes; class IIa levels of laser radiation are considered non-hazardous if viewed for any period of time less than or equal to 1000 seconds but are considered to be a chronic viewing hazard for any period of time greater than 1000 seconds; class II levels of laser radiation are considered to be a chronic viewing hazard; class Ma levels of laser radiation are considered to be, depending upon the irradiance, either an acute intrabeam viewing hazard or chronic viewing hazard, and an acute viewing hazard if viewed directly with optical instruments; class IIIb levels of laser radiation are considered to be an acute hazard to the skin and eyes from direct radiation; and class IV levels of laser radiation are considered to be an acute hazard to the skin and eyes from direct and scattered radiation (see, e.g., 21CFR1040.10, *Code of Federal Regulations*, Title 21, Volume 8, Chapter 1, Subchapter J, Radiological Health, which is incorporated herein by reference). It is contemplated that the controllable light-emitting elements for use with the system described herein would exclude either class Mb or class IV levels of radiation unless some type of corrective measures are used to reduce the hazard to either skin or tissue, including the eyes.

In one embodiment, the one or more controllable light-emitting elements are configured to illuminate a location on a surface of the body region of the individual corresponding in size and shape to at least one of one or more digitally registered injection sites included in the at least one digital representation of the body region. In one embodiment, the size of the illuminated portion of the body region is highly focused, e.g., not much larger in cross-sectional diameter than the cross-sectional diameter of a needle associated with an injector (e.g., about 0.2 to 4.5 millimeters). This configuration may be appropriate for injections that require precise placement of the needle into the underlying tissue. In one embodiment, the size of the illuminated portion of the body region is broader, e.g., a patch of light on the surface of the body region. This configuration may be appropriate for injections that can accommodate needle placement in a more general or gross area of the underlying tissue, where accurate placement of the needle is not as important or multiple injections are required in the same general location.

In one embodiment, the one or more controllable light-emitting elements configured to emit non-destructive light include one or more of a controllable light-emitting diode, a laser, a laser diode, a collimated light source, or a focused light source. In one embodiment, the one or more controllable light-emitting elements include one or more light-emitting diodes (LEDs), semiconductor light sources available in a variety of colors and sizes. In one embodiment, the one or more controllable light-emitting elements include one or more lasers, non-limiting examples of which include solid-state lasers (e.g., neodymium-Yag laser), gas lasers (e.g., helium lasers), excimer lasers (e.g., chlorine or fluorine mixed with inert gases), and dye lasers (e.g., rhodamine 6G lasers). In one embodiment, the one or more controllable light-emitting elements include one or more laser diodes, semiconductor lasers which may be incorporated into large arrays. In one embodiment, the one or more controllable light-emitting elements include one or more collimated light sources. For example, light from a laser diode or LED may be collimated by passing the light through one or more collimating lens to achieve a narrower band of emitted light. For example, a divergent beam of light emitted from an LED can be collimated with one or more lens and/or curved mirrors. In one embodiment, the one or more controllable light-emitting elements include one or more focused light sources, in which light from a source has been focused with one or more lens to a relatively small point of light.

In one embodiment, the one or more controllable light-emitting elements include one or more controllable projectors. Examples of projectors include but are not limited to movie projectors, video projectors, image projectors, slide projectors, and the like. In one embodiment, the one or more projectors include one or more miniaturized projectors, e.g., handheld projectors, pocket projectors, mobile projectors, pico projectors, or mini beamers. The one or more miniaturized projectors can include digital light processing, beam-steering, and/or light crystal on silicon technologies.

In one embodiment, at least one of the one or more controllable light-emitting elements illuminates a location on the surface of the body region with at least one of a color or pattern of light indicative of at least one treatment parameter. In one embodiment, the color of light emitted by the one or more controllable light-emitting elements is derived from a colored light source, e.g., a light-emitting diode (LED), laser, or laser diode emitting light of a specific wavelength, spectrum, or color. In one embodiment, the color of light emitted by the one or more controllable light-emitting elements is derived from one or more colored filters placed so as to modulate the color of light emitted by a controllable light-emitting element. For example, the color of light emitted may be controlled by one or more colored filters placed in the path of white light emitted from one or more light-emitting elements. In one embodiment, the color of light emitted by the one or more controllable light-emitting elements is derived from a projected color image that includes projected injection sites of a specific color.

In one embodiment, the pattern of light emitted by the at least one of the one or more controllable light-emitting elements comprises a dot or spot, a crosshair, a circle, concentric circles, or crosshairs. In one embodiment, the pattern of light emitted by the at least one of the one or more controllable light-emitting elements includes one or more of a letter, number, shape, symbol, or combinations thereof.

The pattern of light emitted from the one or more controllable light-emitting elements to illuminate a surface of a body region can be formed using any of a number of methods, non-limiting examples of which include beam/splitting, multispot, beam shaping, or TopHat. In one embodiment, a form of beam shaping is performed to generate a particular pattern of illuminated light from the controllable light-emitting elements. In one embodiment, beam transformers perform a one-to-one mapping of points in an input plane to points in an output plane, a non-limiting example of which is a Gaussian-to-TopHat shaper for a single-mode laser. In one embodiment, band-limited diffusers, diffractive beamsplitters, and/or beam integrators can be used to perform a many-to-one mapping of points in one plane to multiple points in another plane of the beam. The beam is broken up into multiple beamlets and either overlapped (beam integration) or directed into different directions (diffusers and beam splitters). For example, light emitted from laser diodes can be shaped into a variety of patterns, e.g., linear, square, rectangle, grid, round, elliptical, circle/concentric circles, crosshair, or scope using beam-shaping optics, e.g., beam splitters and/or pattern generators, examples of which are commercially available (from, e.g., Frankfurt Laser Company, Freidrichsdorf, Germany). For example, light emitted from LEDs can be collected, collimated and then diffused to shape the beam of light using LED LightShapters™ and Engineered Diffusers™ (from RPC Photonics, Inc., Rochester, N.Y.). In one embodiment, the patterns, e.g., circles, dot matrix, grid, line, square, or crosshair, can be generated using an optical projection head (from, e.g., Edmund Optics, Inc., Barrington, N.J.) attached to a laser or laser diode. Beam splitters, beam shapers, diffusers, Fourier holograms for generating structured light patterns are also available from HOLOEYE Systems Inc., Carlsbad, Calif.; Holo/Or Ltd., Rehovot, Israel; Coherent Inc., Santa Clara, Calif.; and Luminit, LLC, Torrance, Calif.

In one embodiment the pattern of light emitted by the one or more controllable light-emitting elements is derived from one or more physical lighting template, e.g., a gobo, placed in the path of the emitted light (from e.g., InLight Gobos, Dallas Tex.).

In one embodiment, the pattern of light emitted by the one or more controllable light-emitting elements to illuminate one or more injection sites is part of a projected image, the projected image including projected injection sites.

In one embodiment, the one or more illuminated injection sites are round in shape. However, the shape of the one or more illuminated injection sites is not restricted to being circular in shape and can include, for example, oval, square, rectangular, trapezoid or triangular shapes.

In one embodiment, the one or more illuminated injection sites are linear in shape, e.g., a line. In one embodiment, an illuminated injection site that is linear in shape may be used for serial needle sticks or linear threading along the path of the linear shape. In one embodiment, the one or more illuminated injection sites can be one or more straight lines of illuminated light projected onto the surface of the body region. In one embodiment, the one or more illuminated injection sites can be one or more curved lines of illuminated light projected onto the surface of the body region. The one or more straight lines or curved lines of illuminated light can be continuous or discontinuous depending upon the preferred injection-treatment pattern.

In one embodiment, the at least one of a color or pattern of light emitted by the one or more controllable light-emitting elements is indicative of at least one treatment parameter, the at least one treatment parameter including, but not limited to an injection site, a type of injectable agent for injection at an injection site, a type of injector, a dosage of an injectable agent for injection at an injection site, a sequence of injecting an injectable agent at an injection site, a timing of injecting an injectable agent at an injection site, an injection depth for injection of an injectable agent at an injection site, or an injection angle for injection of an injectable agent at an injection site.

In one embodiment, the at least one treatment parameter is part of an injection-treatment plan indicated for treatment of a specific condition. The injection-treatment plan can include one or more injectable agents, dosing of the one or more injectable agents, timing of dosing of each of the one or more injectable agents, sequence of dosing of each of the one or more injectable agents, or placement of injection of each of the one or more injectable agents. For example, the injection-treatment plan may be represented by at least one of a color or pattern of light emitted by the one or more controllable light-emitting elements indicating the time intervals at which a specific injectable agent should be repeatedly injected at the same or different illuminated injection sites over a period of time, e.g., over the course of a 30 to 60 minute office visit. When two or more injectable agents are indicated for use in the condition, the injection-treatment plan may be represented by at least one of a color or pattern of light emitted by the one or more controllable light-emitting elements indicative of the sequence of injection of the two or more injectable agents.

In one embodiment, the at least one of a color or pattern of light emitted by the controllable light-emitting elements is indicative of a type of injectable agent to be injected at a given injection site. Non-limiting examples of injectable agents include neurotoxins, subcutaneous dermal enhancers, insulin, antibiotics, hormones, chemotherapeutic agents, anti-inflammatory agents, or other biological agents.

Returning to FIG. 1, system 100 includes computing device 160. Computing device 160 is operably connected (e.g., communicatively, electromagnetically, magnetically, ultrasonically, optically, inductively, electrically, or capacitively connected, or the like) to one or more controllable light-emitting elements 110. In one embodiment, computing device 160 is operably connected to one or more controllable light-emitting elements 110 through one or more wired transmissions, e.g., one or more electrical connections. In one embodiment, computing device 160 is operably connected to one or more controllable light-emitting elements 110 through one or more wireless transmissions, e.g., one or more radio frequency transmissions. Wired transmission can further include, but is not limited to, transmission through one or more of a telephone line, cable line, internet line, fiber optic line, coaxial cable, UPT/STP or any other like wired communication line. Wireless transmission can further include, but is not limited to, one or more radio transmission, microwave transmission (e.g., wireless LAN, Wi-Fi, wireless PAN, Bluetooth, wireless WAN, 2G/3G, broadband, MAN, WiMAX, radar and satellite communications), or infrared transmission (e.g., point-to-point or broadcast communication).

Figure 2:
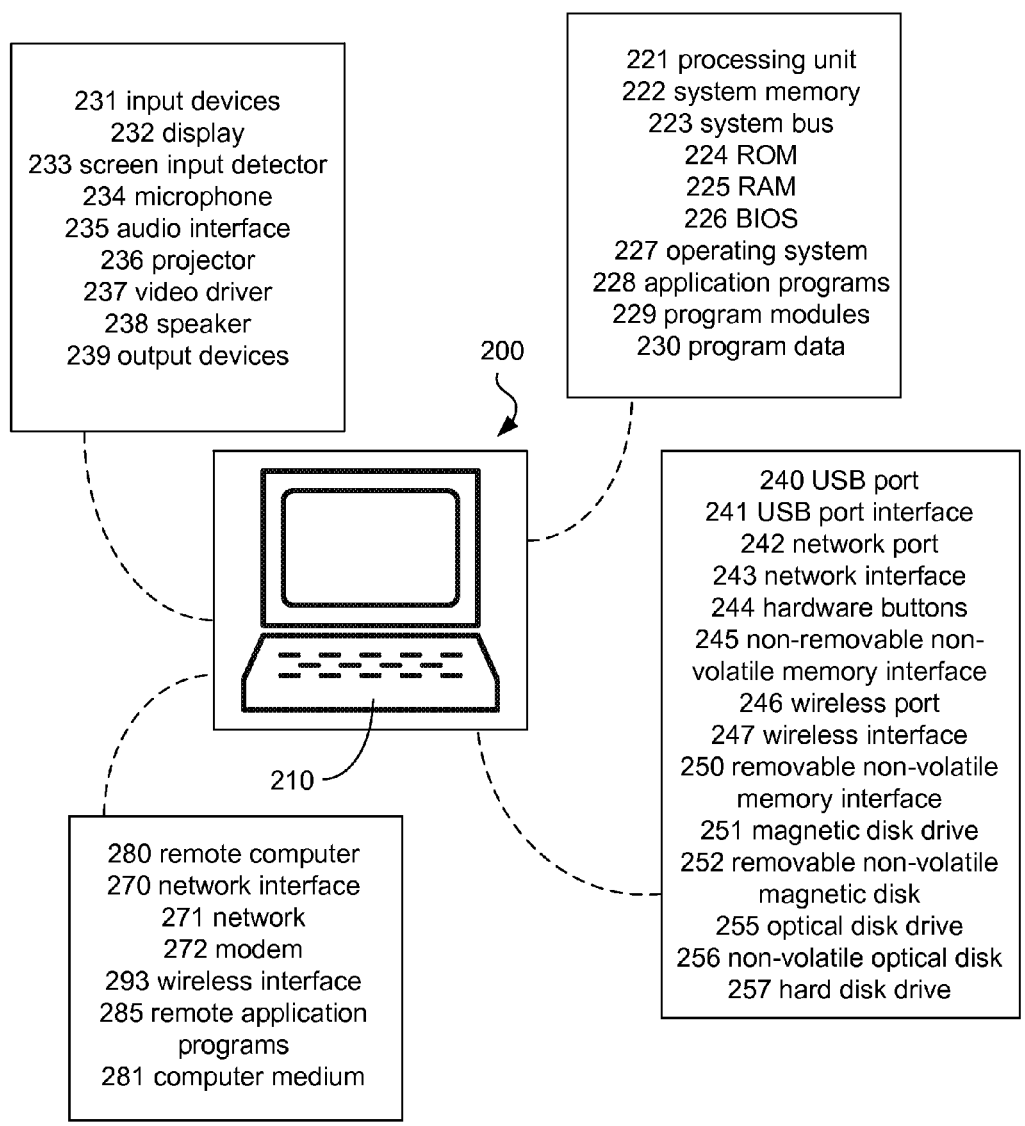
FIG. 2 is a schematic of an embodiment of a computing device.

FIG. 2 illustrates further embodiments of a computing device. Computing device 200 includes a processing unit 221, a system memory 222, and a system bus 223 that couples various system components including the system memory 222 to the processing unit 221. Processing unit 221 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGA having a plurality of programmable logic commands.

The system bus 223 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing device can include one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In one embodiment, one or more user input/output components are operably coupled to the computing device to control (electrical, electromechanical, software-implemented, firmware-implemented, or other control, or combinations thereof) generation of an injection guide specific to an individual and/or to control illumination from one or more controllable light-emitting elements.

The system memory includes read-only memory (ROM) 224 and random access memory (RAM) 225. A basic input/output system (BIOS) 226, containing the basic routines that help to transfer information between sub-components within computing device 200, such as during start-up, is stored in the ROM 224. A number of program modules may be stored in the ROM 224 or RAM 225, including an operating system 227, one or more application programs 228, other program modules 229 and program data 230.

A user may enter commands and information into the computing device 200 through user input devices, such as a number of switches and buttons, illustrated as hardware buttons 244, connected to the system via a suitable non-removable non-volatile memory interface 245. Input devices 231 may further include a touch-sensitive display with suitable input detection circuitry, illustrated as a display 232 and screen input detector 233. The output circuitry of the touch-sensitive display 232 is connected to the system bus 223 via a video driver 237. Other input devices may include a microphone 234 connected through a suitable audio interface 235, and a physical hardware keyboard 210. Output devices may include at least one display 232, or a projector 236.

In addition to the display 232, the computing device 200 may include other peripheral output devices, such as at least one speaker 238. Other external input devices 231 or output devices 239, such as a joystick, game pad, satellite dish, scanner or the like, may be connected to the processing unit 221 through a USB port 240 and USB port interface 241, to the system bus 223. Alternatively, the other external input devices 231 and output devices 239 may be connected by other interfaces, such as a parallel port, game port or other port. The computing device 200 may further include or be capable of connecting to a flash card memory (not shown) through an appropriate connection port (not shown). The computing device 200 may further include or be capable of connecting with a network through a network port 242 and network interface 243, and through wireless port 246 and corresponding wireless interface 247 may be provided to facilitate communication with other peripheral devices, including light-emitting elements, image capture devices, other computers, printers, and so on (not shown). It will be appreciated that the various components and connections shown are examples and other components and means of establishing communication links may be used.

A user may enter commands and information into the computing device 200 through input device 231 such as a microphone, keyboard, or pointing device, commonly referred to as a mouse, trackball, or touch pad. Other input devices may include at least one of a touch sensitive display, joystick, game pad, satellite dish, and scanner. These and other input devices are often connected to the processing unit through a user input interface that is coupled to the system bus, but may be connected by other interface and bus structures, such as a parallel port, game port, or a universal serial bus (USB).

The computing device 200 may be designed to include a user interface. The user interface may include a character, a key-based, or another user data input including a keyboard or touch sensitive display. The user interface may include a stylus (not shown). Moreover, the user interface is not limited to an actual touch-sensitive panel arranged for directly receiving input, but may alternatively or in addition respond to another input device such as the microphone 234. For example, spoken words may be received at the microphone 234 and recognized.

In certain instances, the computing system typically includes a variety of computer-readable media products. Computer-readable media may include any media that can be accessed by the computing device 200 and may include both volatile and nonvolatile media, removable and non-removable media. By way of example, and not of limitation, computer-readable media may include computer storage media. By way of further example, and not of limitation, computer-readable media may include a communication media. By way of further example, and not of limitation, computer readable media may include non-transitory signal bearing media.

Communication media may typically embody computer-readable instructions, data structures, program modules, or other data in a modulated data signal such as a carrier wave or other transport mechanism, and include any information delivery media. The term "modulated data signal" means a signal that has one or more of its characteristics set or changed in such a manner as to encode information in the signal. By way of example, and not limitation, communication media may include wired media, such as a wired network and a direct-wired connection, and wireless media such as acoustic, RF, optical, and infrared media.

The computing device 200 may also include other removable/non-removable, volatile/nonvolatile computer storage media products. For example, such media includes a non-removable non-volatile memory interface (hard disk interface) 245 reads from and writes for example to non-removable, non-volatile magnetic media, or a removable non-volatile memory interface 250 that, for example, is coupled to a magnetic disk drive 251 that reads from and writes to a removable, non-volatile magnetic disk 252, or is coupled to an optical disk drive 255 that reads from and writes to a removable, non-volatile optical disk 256, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 257 is typically connected to the system bus 223 through a non-removable memory interface, such as the interface 245, and magnetic disk drive 251 and optical disk drive 255 are typically connected to the system bus 223 by a removable non-volatile memory interface, such as interface 250.

The drives and their associated computer storage media discussed above provide storage of computer-readable instructions, data structures, program modules, and other data for the computing device 200.

The computing device may operate in a networked environment using logical connections to one or more remote computers, such as a remote computer 280. The remote computer 280 may be a personal computer, a server, a router, a network PC, a peer device, or other common network node, and typically includes many or all of the elements described above relative to the computing device 200. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing device is connected to the network 271 through a network interface, such as the network interface 270, the modem 272, or the wireless interface 293. The network may include a LAN network environment, or a WAN network environment, such as the Internet. In a networked environment, program modules depicted relative to the computing device 200, or portions thereof, may be stored in a remote memory storage device. By way of example, and not limitation, remote application programs 285 may reside on computer medium 281. It will be appreciated that the network connections shown are examples and other means of establishing a communication link between the computers may be used.

In certain instances, one or more elements of the computing device 200 may be deemed not necessary and omitted. In other instances, one or more other components may be deemed necessary and added to the computing device 200.

In one embodiment, image-based applications such as viewers and/or toolkits (e.g., Insight Segmentation and Registration Toolkit (ITK)), are incorporated for further intake of information. In one embodiment, CAD implementations or image segmentation may allow processing of received digital images.

In one embodiment, the computing device includes a computer-readable media drive or memory slot that is configured to accept non-transitory signal-bearing medium (e.g., computer-readable memory media, computer-readable recording media, or the like). In one embodiment, a program for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, cloud, or the like.

In one embodiment, the computing device includes one or more modules optionally operable for communication with one or more input/output components that are configured to relay user output/input. In one embodiment, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electromechanical systems (MEMS) elements, or other actuators.

Figure 3:
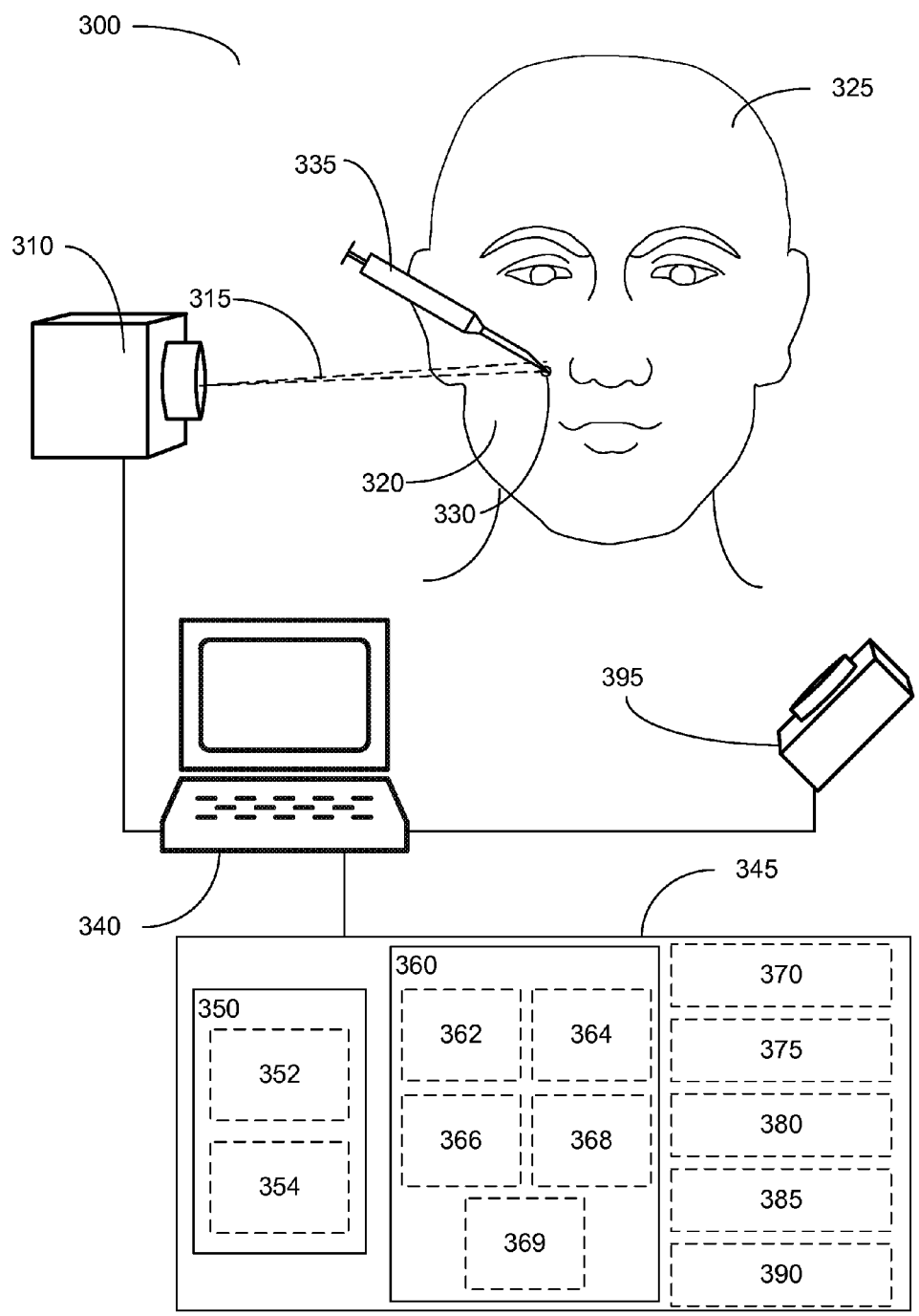
FIG. 3 is a schematic of an embodiment of a system for guiding injection in an individual.

FIG. 3 illustrates further embodiments of a system for guiding injection in an individual. System 300 of FIG. 3 includes a controllable light-emitting element 310 emitting light 315 onto the surface of body region 320 of individual 325 to illuminate injection site 330. Illuminated injection site 330 on body region 320 of individual 325 is a target for injection of an injectable agent with injector 335.

System 300 further includes computing device 340. Block diagram 345 illustrates further embodiments of computing device 340. Block 350 illustrates that computing device 340 is operable to receive at least one digital representation of a body region of an individual, the body region of the individual including one or more physical registration landmarks, the at least one digital representation including one or more digitally registered injection sites and one or more digital registration landmarks corresponding to the one or more physical registration landmarks on the body region. In one embodiment, the at least one digital representation including one or more digitally registered injection sites and one or more digital registration landmarks corresponding to the one or more physical registration landmarks on the body region are received from another device, e.g., another computing device, an image capture device, or other device capable of storing and transmitting the at least one digital representation. In one embodiment, the at least one digital representation may be received from a physician or other practitioner at a location remote from computing device 340. For example, the at least one digital representation may be captured and annotated with one or more digitally registered injection sites on a computing device in a first physician's office and transmitted to a second computing device in a second physician's office, other practitioner's office, or a treatment room. In the case of self-injection therapy, the at least one digital representation including one or more digitally registered injection sites may be sent to a computing device in a system for guiding injection at the individual's home, place of work, or other location where the individual engages in self-injection. In one embodiment, the at least one digital representation is received internally from one portion of a computing device to another portion of the computing device, having been generated on said computing device using one or more digital images of the body region of the individual.

Block 350 includes optional blocks 352 and 354. Block 352 illustrates computing device 340 optionally operable to receive the at least one digital representation of the body region of the individual through a wired transmission or a wireless transmission. For example, computing device 340 can include a transceiver unit capable of receiving a wireless transmission including information regarding the at least one digital representation of the body region. In one embodiment, computing device 340 can include a port, e.g., a USB port, for wired transmission of the one or more digital representations of the body region from another device, e.g., a computing device and/or an external image capture device.

Block 354 illustrates computing device 340 optionally operable to receive at least one digital representation of a face, head, neck, torso, abdomen, upper extremity, lower extremity, buttocks, or other body region accessible for injection by an injectable agent. The body region can further include one or more physical registration landmarks. The one or more physical registration landmarks can include one or more markings placed on the body region of the individual. For example, the one or more physical registration landmarks can include one or more markings, e.g., washable inks, adhesive dots or stickers, or other marking agents, placed on the surface of the skin by a physician or other practitioner. In one embodiment, the one or more physical registration landmarks include one or more of a pigmentation, pigmented area, skin texture pattern, tattoo, blemish, scar, anatomical feature, or subsurface blood vessel on the body region of the individual. For example, the one or more physical registration landmarks can include one or more pigmented areas such as freckles or moles or one or more anatomical features such as a nose, lip, cheek, eye, brow, joint, or other anatomical features. An extensive list of landmarks of the facial area, for example, are described in Buckley et al., *Am. J. Psychiatry* (2005) 162:606-608, which is incorporated herein by reference.

The at least one digital representation of the body region received by the computing device includes one or more digital registration landmarks corresponding to the one or more physical registration landmarks on the body region. In general, the one or more digital registration landmarks corresponding to the one or more physical registration landmarks on the body region may be used to register digitally registered injection sites relative to illuminated injection sites to ensure that the light emitted from the one or more controllable light-emitting elements illuminates the proper locations on the surface of the body region of the individual despite movement of either the individual or the one or more controllable light-emitting elements.

The digital representation of the body region includes one or more digitally registered injection sites. The one or more digitally registered injection sites are digital representations of one or more injection sites on the body region of the individual. In one embodiment, the one or more digitally registered injection sites are added to a digital representation of the body region prior to the digital representation being received by the computing device. For example, the one or more digitally registered injection sites may be added to the at least one digital representation of the body region by a physician or other practitioner. In one embodiment, the one or more digitally registered injection sites are added automatically to the at least one digital representation of the body region based on a computational analysis. The one or more digitally registered injection sites can be registered relative to one or more of the digital registration landmarks, the one or more digital registration landmarks substantially corresponding to the one or more physical registration landmarks on the body region of the individual. For example, a digitally registered injection site may be situated at a location represented by XYZ coordinates relative to one or more digital registration landmarks. The illuminated injection site is similarly situated at the same XYZ coordinates relative to the physical registration landmarks. Methods for registering points with anatomical image data are provided in Hopenfeld et al., *Ann. Biomed. Eng.* (2007) 35:1771-1781, which is incorporated herein by reference.

The one or more digitally registered injection sites correspond in location to one or more illuminated injection sites on the body region of the individual and in one embodiment may be arranged in an injection-treatment pattern as part of an injection-treatment plan. The injection-treatment pattern can include the location of each intended injection site as represented by the digitally registered injection sites. In one embodiment, the injection-treatment pattern can include the sequence and/or timing of injection at two or more injection sites. The pattern may be specific to the individual or to the condition being treated. For example, the injection-treatment pattern may be predetermined depending upon the type of injectable agent and/or the condition being treated. For example, cosmetic treatment of a portion of the face, e.g., the glabella frown lines, may follow a predetermined pattern of injection sites. In one embodiment, the predetermined injection-treatment pattern is provided by a computing device that stores injection-treatment patterns specific for a condition, specific for an injectable agent, and/or specific for an individual.

In one embodiment, the injection-treatment pattern is part of an injection-treatment plan. In one embodiment, the injection-treatment plan is specific to the individual. For example, the one or more illuminated injection sites may be arranged in an injection-treatment pattern based on the specific needs of the individual for whom the injection-treatment plan is designed. In this case, the number and placement of the one or more illuminated injection sites are specifically prescribed for the individual. In one embodiment, the injection-treatment plan is specific to a condition in need of treatment. In one embodiment, the injection-treatment plan is generic for a given condition. For example, the injection-treatment pattern can be a series of rows and/or columns of illuminated injection sites, any one or more of which may be accessed during the course of treatment.

In one embodiment, the one or more injection-treatment plan is predetermined. For example, the injection-treatment plan may be predetermined depending upon the type of injectable agent and/or the condition being treated. For example, cosmetic treatment of a portion of the face, e.g., the glabella frown lines, may follow a predetermined pattern of injection sites. In one embodiment, the predetermined injection-treatment plan is provided by a computing device that stores injection-treatment plans specific for a condition, specific for an injectable agent, or for a specific individual.

In one embodiment, the injection-treatment plan is anatomical feature dependent. For example, an injection-treatment plan designed for use on the face of an individual may include a pattern of injections dependent upon a particular anatomical feature of the face, e.g., the eye brow, the glabella, or cheek folds. In one embodiment, the anatomical feature can include an anatomical feature that might be contraindicated as an injection site, e.g., an underlying blood vessel, joint, or inside the orbit of the eye, and as such the one or more illuminated injection sites are located to avoid this anatomical feature. In one embodiment, the anatomical features of the body region are fairly uniform, e.g., the anatomical features of the upper thigh, and as such the arrangement of the one or more illuminated injection sites can be more generalized or less specific to the individual.

In one embodiment, an injection-treatment plan including an injection-treatment pattern of one or more illuminated injection sites is developed for the specific needs of an individual. In the case of an injection-treatment plan designed for use on the face of an individual for cosmetic use, for example, the arrangement of the one or more illuminated injection sites can include situating the one or more illuminated injection sites over, for example, one or more lines, wrinkles, folds, or pouches in need of treatment on the individual's face. In one embodiment, the one or more illuminated injection sites are situated over one or more horizontal forehead lines, glabellar frown lines, periorbital lines, preauricular lines, cheek lines, nasolabial folds, upper radial lip lines, lower radial lip lines, corner of the mouth lines, marionette lines, labiomental crease, and/or horizontal neck folds.

In one embodiment, an injection-treatment plan designed for use on the face of an individual can include an injection-treatment pattern of one or more illuminated injection sites situated over one or more muscles associated with creating lines and wrinkles on the individual's face. For example, the one or more illuminated injection sites can be situated over the occipito-frontalis muscle of the forehead for treatment of horizontal forehead wrinkles; the procerus muscle between the eyebrows for treatment of horizontal wrinkling above the bridge of the nose; the corrugators muscle for treatment of the wrinkles that appear between the eyebrows; the orbicularis oculi muscles around the eyes for the treatment of "crow's feet;" the nasalis muscles of the nose for the treatment of "bunny lines" along the side of the nose; the orbicularis oris muscles around the lips for the treatment of radial pucker lines on the lips; and the depressor anguli oris muscles under the lips.

In one embodiment, the injection-treatment plan can include an injection-treatment pattern of one or more illuminated injection sites arranged in such a way as to create volume upon injection of a filler substance. For example, a series of illuminated injection sites can be arranged in a linear treatment pattern along a skin fold. In another example, the one or more illuminated injection sites can be arranged in a square injection pattern to facilitate threading of an injectable agent in a crisscross pattern.

In one embodiment, an injection-treatment plan can include an injection-treatment pattern of one or more illuminated injection sites arranged so as to avoid portions of the underlying tissue of the body region that might be contraindicated for administration of an injectable agent. For example, the one or more illuminated injection sites may be arranged so as to avoid injection of an injectable agent into an underlying blood vessel. Other non-limiting examples of contraindicated injection sites include areas of infection, skin disease or inflammation (unless the injectable agent is being used to treat said conditions) or areas too close to the orbits (to prevent ptosis).

Returning to FIG. 3, block 360 illustrates that computing device 340 is operable to control the one or more controllable light-emitting elements to illuminate a location on a surface of the body region of the individual corresponding in location to at least one of the one or more digitally registered injection sites. For example, the computing device may be operable to control an on/off function and/or position of one or more controllable light-emitting elements to direct illumination on the surface of the body region to a location corresponding to one or more injection sites. For example, the computing device may be operable to control sequencing of an array of controllable light-emitting elements such that each of the one or more controllable light-emitting elements in the array are sequentially turned on or off according to an injection-treatment pattern.

Block 360 includes optional blocks 362, 364, 366, 368, and 369. Block 362 illustrates computing device 340 optionally operable to control one or more of an on/off function, position, intensity, focus, color of emitted light, or pattern of emitted light of the one or more controllable light-emitting elements. Block 364 illustrates computing device 340 optionally operable to dynamically control one or more of an on/off function, position, intensity, focus, color of emitted light, or pattern of emitted light of the one or more controllable light-emitting elements before, during, or after injection at one or more illuminated injection sites. For example, the computing device may be operable to change the color of an illuminated injection site, e.g., from green to red, once injection has occurred at said illuminated injection site. Block 366 illustrates computing device 340 optionally operable to control the one or more controllable light-emitting elements to illuminate the surface of the body region in at least one of a spatial or temporal sequence of illumination. For example, the one or more controllable light-emitting elements may be turned on/off in a spatial or temporal sequence to illuminate a single location on the surface of the body region at any given time. For example, the location of any given illuminated injection site may move over the surface of the body region before or after an injection is completed at a previously injected illuminated injection site. In one embodiment, the sequence of illumination is indicative of future injection sites, e.g., illuminating the injection sites that need to be injected next. In one embodiment, the sequence of illumination is indicative of success at a previous injection site, e.g., illuminating the injection sites that have been successfully injected. Block 368 illustrates computing device 340 optionally operable to control at least one of a spatial or temporal sequence of at least one of a color or pattern of light emitted from the one or more controllable light-emitting elements. Block 369 illustrates computing device 340 optionally operable to control the one or more controllable light-emitting elements to illuminate a location on a surface of the body region of the individual corresponding in size to at least one of the one or more digitally registered injection sites.

FIG. 3 illustrates further embodiments of computing device 340. Block 370 illustrates that computing device 340 is optionally operable to control the one or more controllable light-emitting elements to project one or more pieces of information or annotations onto the surface of the body region. For examples, the one or more pieces of information can include one or more pieces of information projected on the surface of the body region to instruct a user, e.g., a physician, practitioner or other user, as to the injection-treatment pattern or injection-treatment plan. In one embodiment, the one or more pieces of information are projected at or near one or more illuminated injection sites. The one or more pieces of information can be represented by one or more letters, numbers, shapes, text, symbols, colors, or combinations thereof. In one embodiment, the one or more pieces of information can include one or more treatment parameters. For example, the one or more pieces of information projected onto the surface of the body region may include text describing the injectable agent, e.g., a neurotoxin, and the dosage of said injectable agent, e.g., units per injection, to be used at a given illuminated injection site. In one embodiment, the one or more pieces of information can include one or more injection status updates, the one or more injection status updates including, but not limited to, one or more of a running clock, a number of injections completed, a number of injections remaining, or a status of alignment of one or more illuminated injection sites with the one or more physical registration landmarks on the body region. For example, a running clock may be projected onto the surface of the body region, e.g., on the surface of the individual's forehead, to inform the physician or other practitioner as to how much time has expired between injections or over the course of an injection treatment session. For example, the number of injections completed and/or the number of injections still needed to be performed may be projected onto the surface of the body region to inform the user, e.g., a physician or other practitioner, as to how well the injection treatment session is progressing.

Block 375 illustrates that computing device 340 is optionally operable to receive one or more digital images of the body region including the one or more physical registration landmarks and one or more illuminated injection sites on the body region from at least one image capture device 395; and adjust the one or more controllable light-emitting elements 310 so as to align the one or more illuminated injection sites relative to the one or more physical registration landmarks on the body region to substantially correspond to the at least one digital representation of the body region. In one embodiment, the computing device is operable to align the one or more digital images of the body region including the one or more physical registration landmarks and the one or more illuminated injection sites with the digital representation of the body region including one or more digital registration landmarks and one or more digitally registered injection sites using one or more of an image registration algorithm. In general, the computing device is operable to detect features depicted in the digital images, e.g., the physical registration landmarks, and match these features with features in the digital representation, e.g., the digital registration landmarks. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. The computing device is further operable to match the features detected in the one or more images of the body region with features in the digital representation of the body region using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser *Image Vision Computing* (2003) 21:977-1000. The computing device is operable to adjust the one or more light-emitting elements to keep the components of the digital images, i.e., the one or more physical registration landmarks and the one or more illuminated injections sites, aligned with the components of digital representation, i.e., the one or more digital registration landmarks and the one or more digitally registered injection sites. In one embodiment, adjusting the one or more light-emitting elements can include instructing the one or more light-emitting elements to move so as to change the location of the illuminated injection site on the surface of the body region. In one embodiment, adjusting the one or more light-emitting elements can include instructing the one or more light-emitting elements in an array to turn on or off so as to change the location of the illuminated injection site on the surface of the body region.

Block 380 illustrates that computing device 340 is optionally operable to control the one or more controllable light-emitting elements configured to emit non-destructive light to illuminate a location on the surface of the body region of the individual corresponding in location to at least one of the one or more digitally registered injection sites based on registration of the one or more digitally registered injection sites with the one or more digital registration landmarks corresponding to the one or more physical registration landmarks on the body region.

Block 385 illustrates that computing device 340 is optionally operable to record to one or more data storage devices information regarding an injection treatment session including at least one of one or more injections given at one or more illuminated injection sites, a type of injectable agent, a dosage of an injectable agent, a type of injector, a sequence of injections, a timing of injection, an injection depth, or an injection angle, the length of the injection treatment session, a treatment outcome, and any adverse reactions associated with the injection treatment session.

Block 390 illustrates that computing device 340 is optionally operable to receive one or more digital images of the body region including one or more physical registration landmarks from at least one image capture device; generate at least one digital representation of the body region using the one or more digital images, the at least one digital representation including one or more digital registration landmarks corresponding to the one or more physical registration landmarks on the body region; generate an injection-treatment plan based on analysis of the at least one digital representation of the body region; and add one or more digitally registered injection sites to the at least one digital representation of the body region, the one or more digitally registered injection sites registered relative to the one or more digital registration landmarks.

Returning to FIG. 3, system 300 further optionally includes image capture device 395. In one embodiment, image capture device 395 is configured to acquire one or more digital images of body region 320 including the one or more physical registration landmarks and illuminated injection site 330 on the surface of body region 320 of individual 325. In one embodiment, image capture device 395 can be used to provide real-time feedback as to the registration of the illuminated injection sites relative to the one or more physical registration landmarks in accordance with the at least one digital representation of the body region. In one embodiment, image capture device 395 is configured to capture an image of an injector relative to an illuminated injection site to assist in accurate placement of the injector. In one embodiment, image capture device 395 is configured to document successful or erroneous injection of an injectable agent at a given illuminated injection site. In one embodiment, image capture device 395 is configured to acquire one or more digital images used to generate the at least one digital representation of the body region of the individual.

Image capture device 395 can include one or more passive or active scanners, digital cameras, charge-coupled device (CCD), complementary metal oxide semiconductor (CMOS), infrared sensor, or any other device suited to capturing an image of a body region. Other non-limiting examples of an image capture device include an ultrasound device, a photoacoustic device, a thermal imaging device, a contact scanning device, a non-contact scanning device, a magnetic resonance imaging device, a computed tomography device, a capacitance measuring device, an electomyographic device, or other biomedical imaging devices. Image capture device 395 is further configured to transmit one or more output signals having information associated with the one or more digital images to computing device 395 through one or more wired or wireless transmissions.

Figure 4:
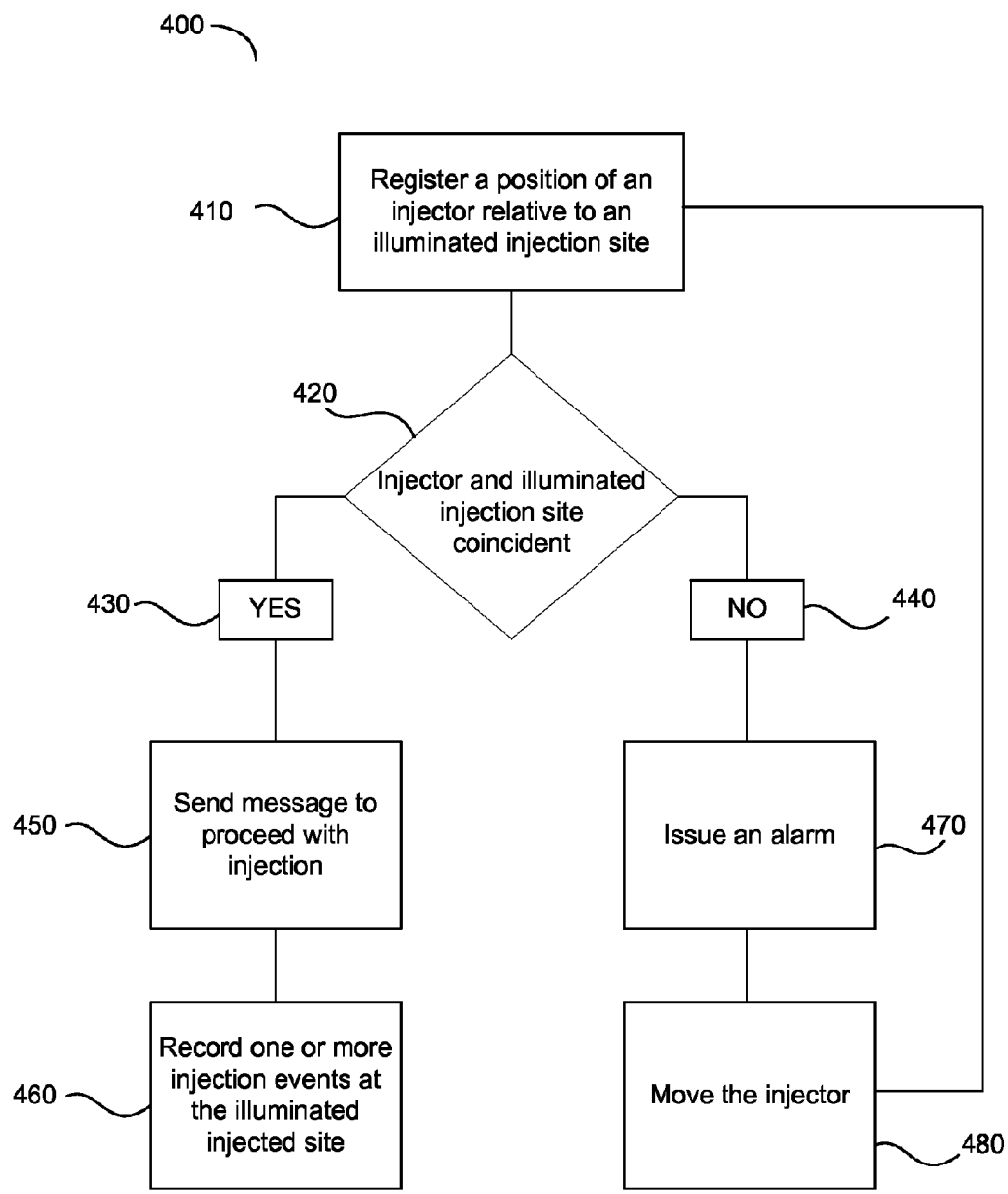
FIG. 4 is a flow-diagram of an embodiment of a method for guiding injection in an individual.

FIG. 4 illustrates further embodiments of a system for guiding injection. In one embodiment, as illustrated in flow diagram 400, the computing device of the system is operable to register a position of an injector relative to an illuminated injection site at step 410. The position of an injector may be registered based on analysis of one or more digital images that include the injector and an illuminated injection site. Alternatively, the injector may include a sensor, e.g., a photo-sensor, which is activated when the injector is in the path of the light beam illuminating the injection site. The computing device is operable to determine whether the injector and illuminated injection sites are coincident at step 420. If the injector and the illuminated injection site are coincident at step 430, then a message is sent to proceed with injection at step 450. The message can be an audio, visual, or haptic message. The computing device is then operable to record one or more injection events at the illuminated injection site at step 460. If the injector and the illuminated injection site are not coincident at step 440, then the computing device is operable to issue an alarm at step 470. The alarm can be an audio, visual, haptic alarm. In one embodiment, the alarm can include haptic feedback. In response, the user moves the injector at step 480, and the computing device again registers the position of the injector relative to the illuminated injection site 410.

Figure 5:
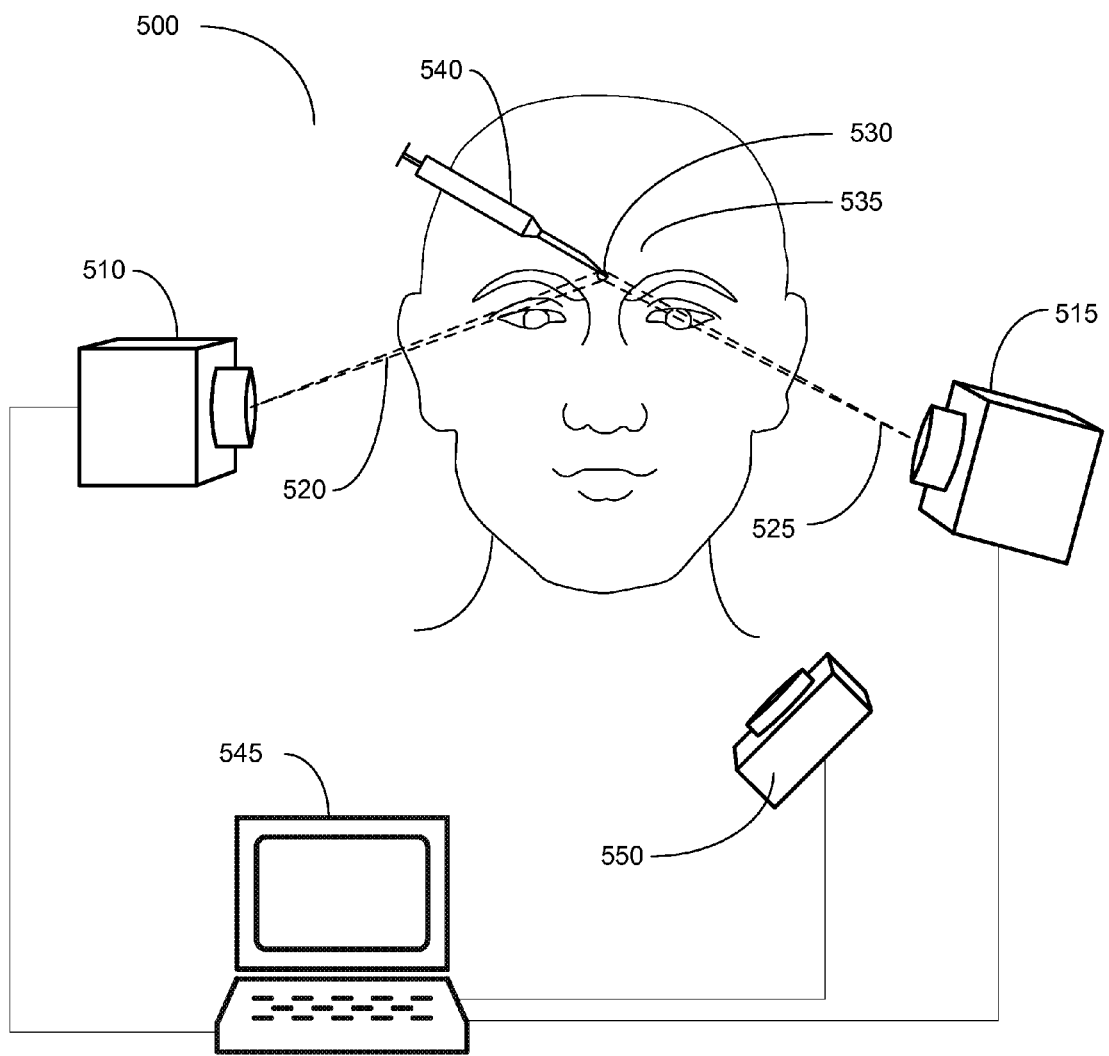
FIG. 5 is a schematic of an embodiment of a system for guiding injection in an individual.

In one embodiment, a system for guiding injection includes at least two or more controllable light-emitting elements configured to emit non-destructive light and positioned to illuminate an injection site on a body region of an individual from two or more angles or positions relative to the surface of the body region. Two or more controllable light-emitting elements positioned at two or more angles are used to ensure that at least one beam of light from the two or more controllable light-emitting elements is able to reach the intended injection site. For example, in a treatment room containing two or more controllable light-emitting elements located so as to emit light onto the surface of a body region of an individual, it is conceivable that the user, e.g. a physician or other practitioner, will inadvertently block one or more beams of emitted light in the process of trying to place a needle of an injector at or near an illuminated injection site. In one embodiment, the computing device of the system is operable to selectively turn on and/or off one or more of the two or more controllable light-emitting elements depending upon whether a light beam is broken to ensure that at least one of the two or more controllable light-emitting elements is illuminating the one or more injection sites. FIG. 5 illustrates an embodiment of a system for illuminating an injection site with two controllable light-emitting elements. System 500 includes first controllable light-emitting element 510 and second controllable light-emitting element 515. First controllable light-emitting element 510 emits beam 520 to illuminate injection site 530 on body region 535. Second controllable light-emitting element 515 emits beam 525 to also illuminate injection site 530 on body region 535. Illuminated injection site 530 is a target of injection by injector 540. System 500 further includes computing device 545 operable to receive one or more digital representations of body region 535 of an individual and to control first controllable light-emitting element 510 and second controllable light-emitting element 515.

System 500 optionally includes image capture device 550. In one embodiment, image capture device 550 is configured to capture one or more images of the body region of an individual, including one or more illuminated injection sites and an injector, to monitor registration of the illuminated injection sites and proper placement of the injector. In one embodiment, image capture device 550 is also configured to capture one or more images of a body region for use in developing at digital representation of the body region.

In one embodiment, all or part of a system for guiding injection of an individual are incorporated into a treatment room of a physician's office or of a clinic. In one embodiment, all or part of a system for guiding injection of an individual are incorporated into an individual's home. In one embodiment, all or part of the system is incorporated into a piece of furniture, e.g., a chair, table, or bed. In one embodiment, all or part of the system is incorporated into the walls or other structural features of a room. In one embodiment, all or part of the system is free-standing.

Figure 6A:
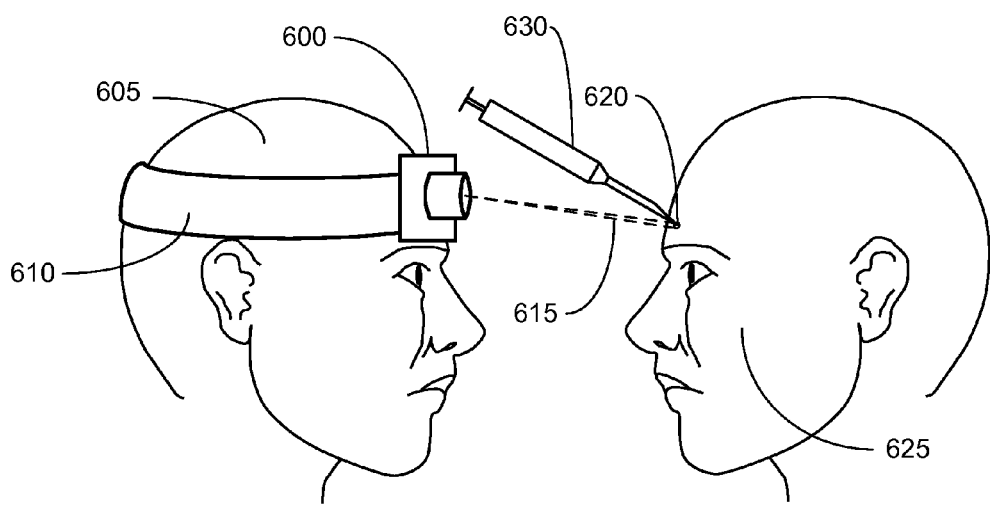
FIGS. 6A-6C are schematics of an embodiment of a system for guiding injection in an individual mounted on a head region of a user.
Figure 6B:
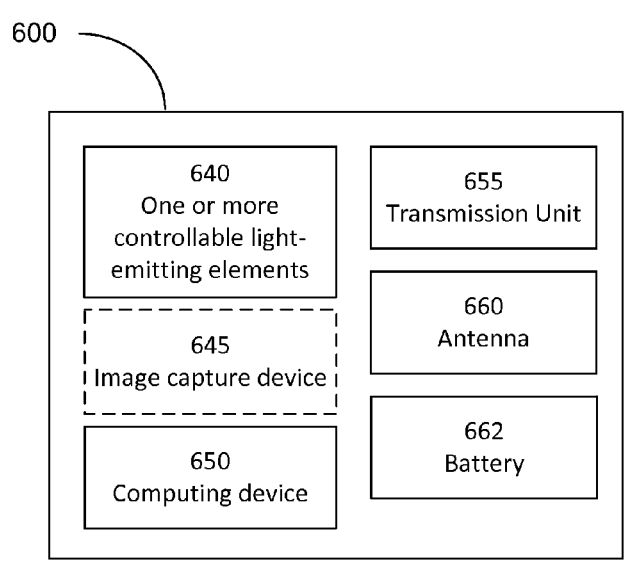
Figure 6C:
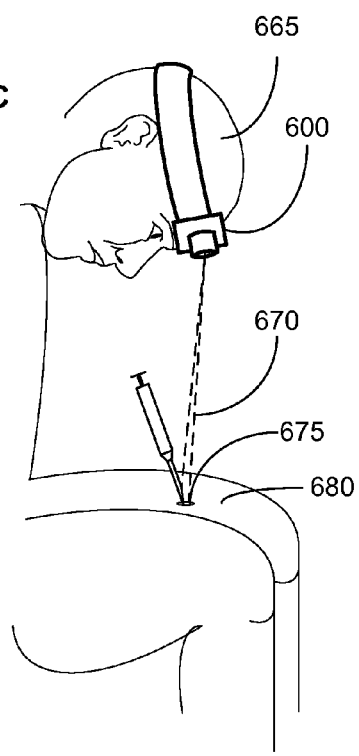

In one embodiment, all or part of a system for guiding injection of an individual is mounted on the head of a user. FIGS. 6A, 6B, and 6C illustrate embodiments of a system mounted on the head of a user for guiding injection of an injectable agent into a body region of an individual. In an embodiment, as illustrated in FIG. 6A, system 600 can be mounted on a head region of user 605. In one embodiment, user 605 is a physician or other practitioner who is carrying out the injections in accordance with an injection-treatment plan. In one embodiment, the user is the individual who uses the head-mounted system for guiding self-injection onto an accessible body region, e.g., lower abdomen or upper thigh, as illustrated in FIG. 6C. System 600 is mounted to head region of a user 605 with head encircling piece 610. In one embodiment, system 600 may be incorporated into a helmet or hat-like structure. In one embodiment, system 600 may be incorporated into a device worn over the eyes, e.g., a pair of glasses. As illustrated in FIG. 6B, system 600 includes one or more controllable light-emitting elements 640 (e.g., one or more laser diodes or LEDs), optionally at least one image capture device 345 (e.g., a camera), and a computing device including a processor 650. One or more controllable light-emitting elements 640 of system 600 emits beam of light 615 onto the surface of a body region of an individual 625. Beam of light 615 illuminates injection site 620, which in turn becomes a target for injection by injector 630.

System 600 further includes transmission unit 655 and antenna 660 configured to receive and transmit input/output signals. For example, transmitter unit 655 and antenna 660 may be configured to receive input signals having information regarding at least one digital representation of a body region of an individual. In one embodiment, transmission unit 655 is directly connected to head-mounted computing device 640. In one embodiment, transmission unit 655 has its own processor that is operably connected to computing device 640. In one embodiment, all or part of computing device 650 may be in a location remote from the controllable light-emitting elements mounted on the head region of an individual. As such, transmitter unit 655 and antenna 660 may be configured to receive input signals from the remote computing device having information for controlling the one or more controllable light-emitting elements. Similarly, transmission unit 655 and antenna 660 may be configured to send output signals having information regarding one or more digital images captured by the at least one image capture device mounted on the head region of the individual.

A "transmission unit," as used herein, can be one or more of a variety of units that are configured to send and/or receive signals, such as signals carried as electromagnetic waves. A transmission unit generally includes at least one antenna and associated circuitry. A transmission unit can include a transmitter and a receiver. A transmission unit can include volatile or non-volatile memory. A transmission unit can include a processor and/or be operably connected to a processor. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice*, 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. A transmission unit can include a hybrid backscatter system configured to function in an RFID, IEEE 802.11x standard and Bluetooth system (see, e.g., U.S. Pat. No. 7,215,976, which is incorporated herein by reference). A transmission unit can include a near field communication (NFC) device. A transmission unit can include a Wireless Identification and Sensing Platform (WISP) device. A transmission unit can be operably coupled to a data storage unit, for example as described in U.S. Pat. No. 7,825,776 and US Patent Application No. 2009/0243813, which are each incorporated herein by reference.

System 600 further includes battery 662 for providing power to the various components of the system. For example, battery 662 can include a camera or watch sized alkaline, lithium, or silver-oxide battery or other appropriately sized and powered battery.

FIG. 6C shows system 600 for use in guiding self-injection of an injectable agent. In this example, individual 665 is performing self-injection on body region 680, e.g., the upper leg of individual 665. One or more controllable light-emitting elements 640 incorporated into system 600 emit beam of light 670 to illuminate injection site 675 on the surface of body region 680.

Figure 7A:
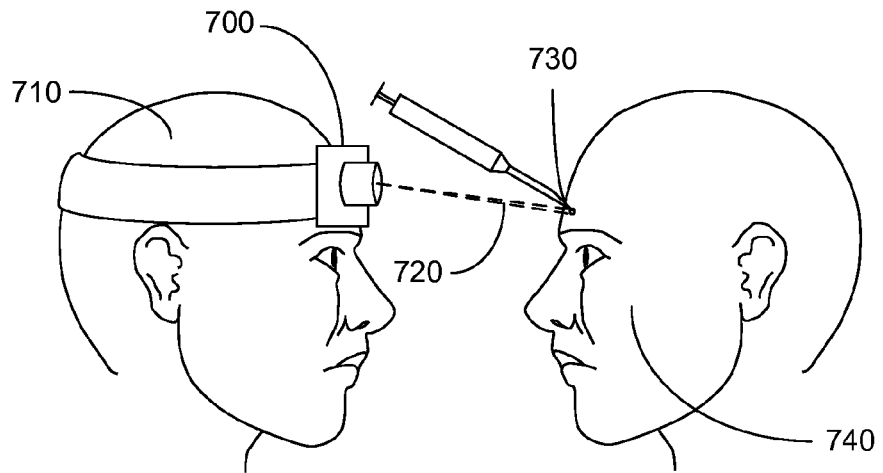
FIGS. 7A-7C are schematics of an embodiment of a system for guiding injection in an individual at first, second, and third illuminated injection sites.
Figure 7B:
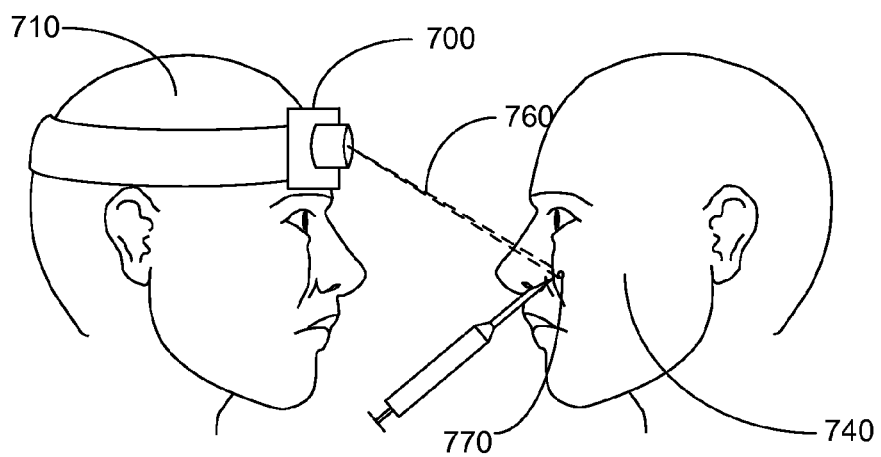
Figure 7C:
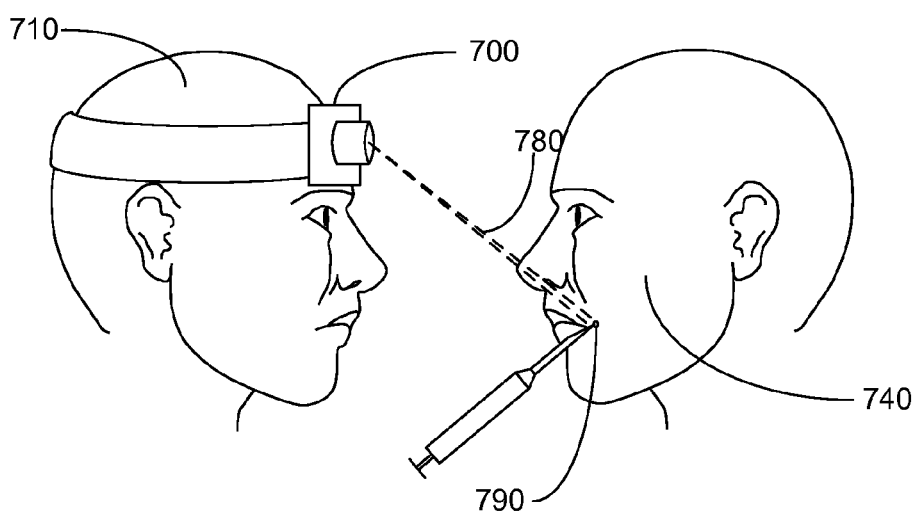

In one embodiment, the one or more injection sites are illuminated on the surface of the body region of an individual in a sequential pattern in accordance with an injection-treatment plan. In an embodiment, the first illuminated injection site is injected first, and after successful completion of the first injection, a second illuminated injection site becomes visible and ready for the second injection. In one embodiment, the first illuminated injection site remains or changes in property, e.g., color or pattern, to indicate that a successful injection has already occurred at this site. In one embodiment, each injection site is illuminated one at a time in a sequence. FIGS. 7A-C illustrate an embodiment of a system for guiding injection in an individual mounted on a user's head in which each injection site is illuminated sequentially under control of the computing device. FIGS. 7A-C further illustrate the steps of sequentially illuminating different injection sites over time. FIG. 7A shows system 700 mounted on a head region of a user 710. One or more controllable light-emitting elements associated with system 700 emit first light beam 720. First light beam 720 illuminates first injection site 730 on the surface of body region 740 of an individual. FIG. 7B shows system 700 emitting second light beam 760 and illuminating second injection site 770 on body region 740 of the individual. FIG. 7C shows system 700 emitting third light beam 780 and illuminating third injection site 790 on body region 740 of the individual. In this way, each injection site is illuminated at a location and in sequence respectively dictated by the digital representation of the body region and associated digitally registered injection sites and the injection-treatment pattern and/or the injection-treatment plan. In one embodiment, the sequencing can be contingent on completing injection at a previously illuminated injection site. For example, system 700 may include a feedback system, e.g., an image capture device, which documents injection at a first illuminated injection site and does not illuminate a second injection site until the injection at the first illuminated injection site is successfully completed. It is further contemplated that the system for sequentially guiding injection in an individual in which each injection site is illuminated sequentially can be positioned relative to the individual in a location that is not necessarily mounted on the head of a user.

In one embodiment, a system for guiding an injection in an individual includes a computing device operable to control the one or more controllable light-emitting elements to project one or more pieces of information or annotation onto a surface of a body region of an individual, as illustrated in FIG. 3. In one embodiment, the one or more pieces of information are projected at or near one or more illuminated injection sites. However, it is contemplated that one or more pieces of information can be projected anywhere on the surface of the body region regardless of the location of the one or more illuminated injection sites. The one or more pieces of information can be represented by one or more letters, numbers, shapes, symbols, text, color, or combinations thereof. The one or more pieces of information can include one or more treatment parameters and/or one or more injection status updates.

Figure 8:
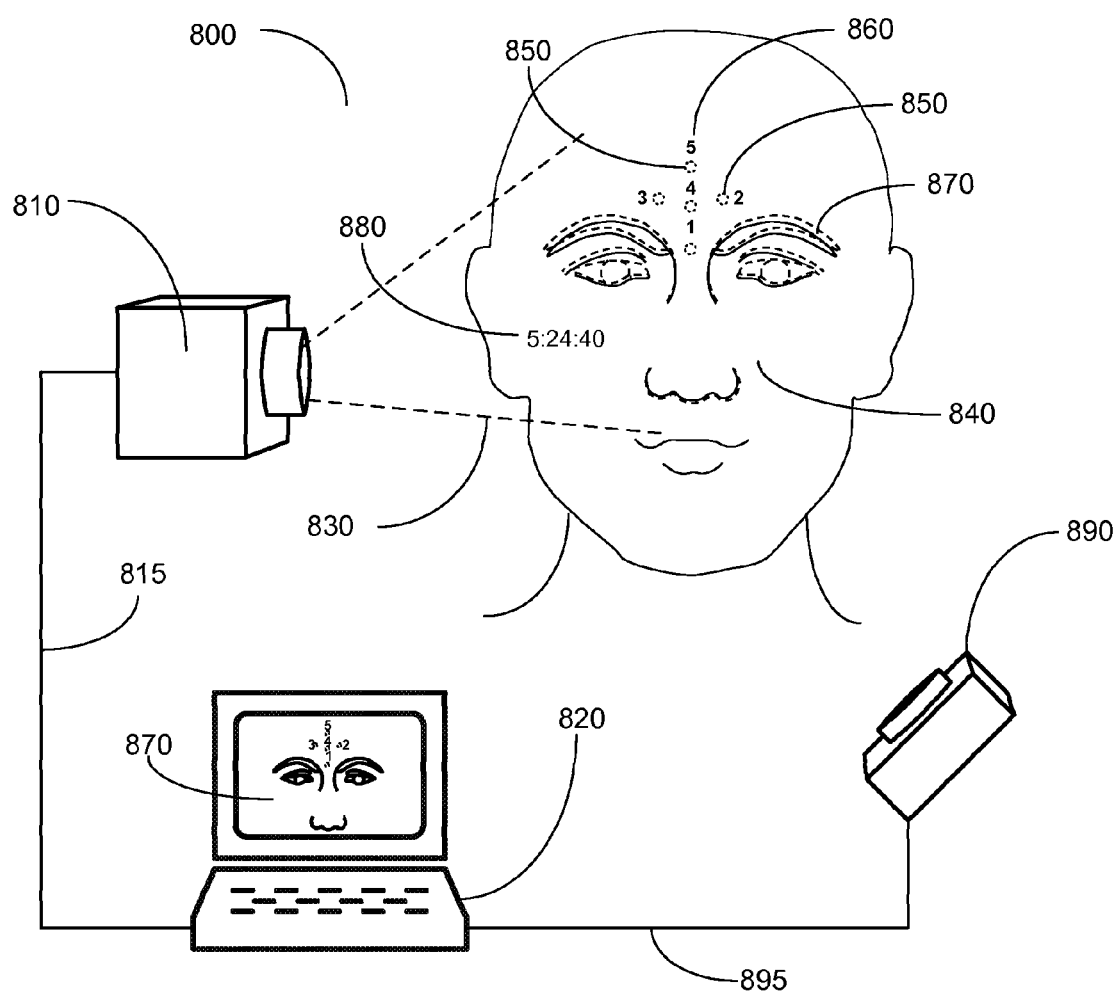
FIG. 8 is a schematic of an embodiment of a system for guiding injection in an individual.

FIG. 8 illustrates an embodiment of a system for guiding an injection into an individual that includes one or more controllable light-emitting elements configured to project one or more pieces of information as well as illuminate one or more injection sites on the surface of a body region of an individual. System 800 includes controllable light-emitting element 810 operably connected to computing device 820 through wired or wireless transmission means 815. Controllable light-emitting element 810 emits a beam of light 830 that illuminates injection sites 850 on the surface of body region 840. In one embodiment, as illustrated in FIG. 8, more than one injection site can be illuminated simultaneously. Controllable light-emitting element 810 also projects pieces of information 860, e.g., numbers, onto the surface of body region 840 indicating a treatment parameter, e.g., an order in which injections at illuminated injection sites 850 should be carried out. In this particular example, each projected piece of information, e.g., a number from 1-5, is projected near an illuminated injection site. Controllable light-emitting element 810 also projects pieces of information 880, e.g., an injection status update in the form of a running clock, at a location distinct from the illuminated injection sites. In one embodiment, the at least one digital representation 870 of body region 840 (shown on the monitor of computing device 820 and on the face of the individual as dotted lines) may also be projected onto the surface of the same said body region, the digital registration landmarks of the at least one digital representation aligning with the physical registration landmarks, e.g., anatomical features such as the nose, eyes, and eye brows as illustrated in FIG. 8. In one embodiment, the one or more pieces of information may be projected in a sequence to coincide with sequential illumination of one or more injection sites on the surface of the body region. System 800 can optionally include image capture device 890 for acquiring one or more digital images of the body region to provide feedback during the injection-treatment session. Image capture device 890 is operably connected to computing device 820 through wired or wireless transmission means 895.

In one embodiment, each of the illuminated injection sites is annotated with one or more pieces of information projected from the controllable light-emitting element. In one embodiment, only a subset of the illuminated injection sites are annotated with one or more pieces of information projected from the controllable light-emitting element. In one embodiment, the one or more pieces of information projected from the controllable light-emitting element are generic and appropriate for use for any individual undergoing treatment for a specific condition. In one embodiment, the one or more pieces of information projected from the controllable light-emitting element are specific to an individual for whom an injection-treatment plan has been designed. For example, the type of injectable agent and/or dosage used may be based on the specific condition of the individual as well as other criteria, e.g., weight, age, skin thickness, allergic response, or other physiological criteria relevant to administration of an injectable agent.

In an embodiment, the one or more pieces of information 860 projected from the controllable light-emitting element are indicative of at least one type of injectable agent to be injected at at least one of the one or more illuminated injection sites. For example, a cosmetic treatment of the face can include one or more pieces of information annotating one or more illuminated injection sites for treating a facial region with at least one injectable agent, e.g., a neurotoxin, subcutaneous volume enhancer, or dermal filler (see, e.g., Carruthers et al., *Plast. Reconstr. Surg.* (2008) 121 (Suppl): 5S-30S, which is incorporated herein by reference). Non-limiting examples of other injectable agents include insulin, antibiotics, hormones, chemotherapeutics or biological agents. In an embodiment, the one or more pieces of information 860 projected from the controllable light-emitting element are indicative of at least one dosage of at least one injectable agent to be injected at at least one of the one or more illuminated injection sites. The dosage of the injectable agent can include one or more units or parts thereof, one or more milliliters or parts thereof, or one or more other measures of dosage. For example, the neurotoxin onabotulinumtoxinA (BOTOX®) is typically injected in 3-5 unit increments per injection. The dosage can also include timing and sequence of injection of the injectable agent. For example, an injectable agent may be injected over a prescribed period of time, e.g., quickly or slowly. For example, a needle of an injector may be left penetrating the injection site for a prescribed period of time. For example, an injectable agent may be injected multiple times over the course of hours, days, or weeks. For example, an injection-treatment plan may include two or more injectable agents and each of two or more injectable agents may be injected in a preferred or prescribed sequence.

In one embodiment, the one or more pieces of information 860 projected from the one or more controllable light-emitting elements are indicative of at least one needle injection depth of at least one type of injectable agent to be injected at at least one of the one or more illuminated injection sites. In one embodiment, the one or more needle injection depth is dependent upon the length of the injection needle. The length of the injection needle can be measured in inches or millimeters (mm). In one embodiment, the length of the injection needle can vary from about 4 mm ($\frac{5}{32}$ inches) to about 12.7 mm ($\frac{1}{2}$ inches). Injection needles of shorter or longer length, e.g., up to about 50 mm (2 inches) or more can also be contemplated for injection at the one or more illuminated injection sites.

In one embodiment, the one or more pieces of information include an injection angle. The angle at which one or more injection needles are injected at the one or more illuminated injection sites can be dependent on the injectable agent and the desired depth of the needle injection into the underlying tissue of the body region of the individual and the desired pattern of injection. For example, injections into the muscle, i.e., intramuscular injection, may be done with an injection needle at a 90 degree angle; injections into the subcutis, i.e, subcutaneous injection, may be done with an injection needle at a 45 degree angle; and injections into the epidermis or dermis may be done with an injection needle at a 10 to 15 degree angle.

The systems and methods described herein for guiding injection into an individual with one or more illuminated injection sites can be implemented on any of a number of body regions including, but not limited to the face, the torso, the abdomen, the neck, the head, the upper extremities, the lower extremities, the buttocks, or any other body region of the individual accessible to injection.

In one embodiment, the systems and methods described herein are used by a physician or other practitioner to guide injection of injectable agents into a patient. In one embodiment, the systems and method described herein are used by an individual to guide self-injection of an injectable agent. Non-limiting examples of injectable agents for self-injection include antibiotics, insulin, fertility hormones (e.g., FSH, ganirelix, cetrotide, Lupron, HCG), immunomodulators (e.g., etanercept), glatiramer (injected daily to treat multiple sclerosis), teriparatide (injected daily to treat osteoporosis), enoxaparin (injected daily to treat deep vein thrombosis), vitamins (e.g., vitamin B12).

Figure 9A:
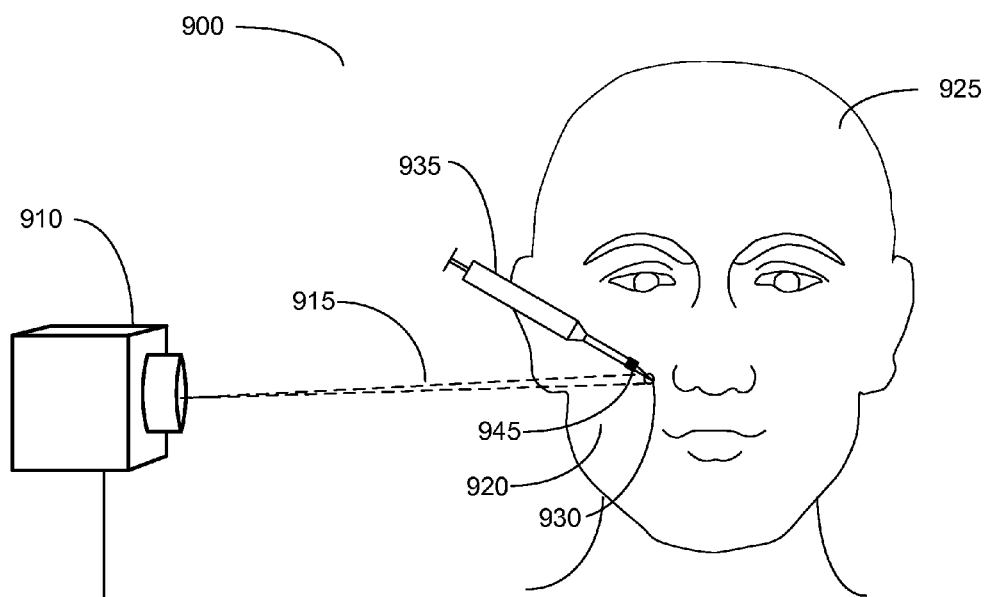
FIGS. 9A & 9B are schematics of an embodiment of a system for guiding injection in an individual with an injector-tracking device.

In one embodiment, a system for guiding injection into an individual includes an injector-tracking device. The injector-tracking device is sized for attachment to an injector and includes at least one alert component and one or more photo-sensors. FIG. 9A illustrates an embodiment of a system including an injector-tracking device. System 900 includes at least one controllable light-emitting element 910 operably connected to computing device 940. The at least one controllable light-emitting element 910 emits light 915 to illuminate injection site 930 on body region 920 of individual 925. Injector 935 includes injector-tracking device 945 attached to the shaft of the injection needle associated with injector 935. Injector-tracking device 945 associated with injector 935 includes one or more photo-sensors. When injector 935 and associated injector-tracking device 945 come close to the illuminated injection site, e.g., cross in the path of light 915, the one or more photo-sensors are activated.

Figure 9B:
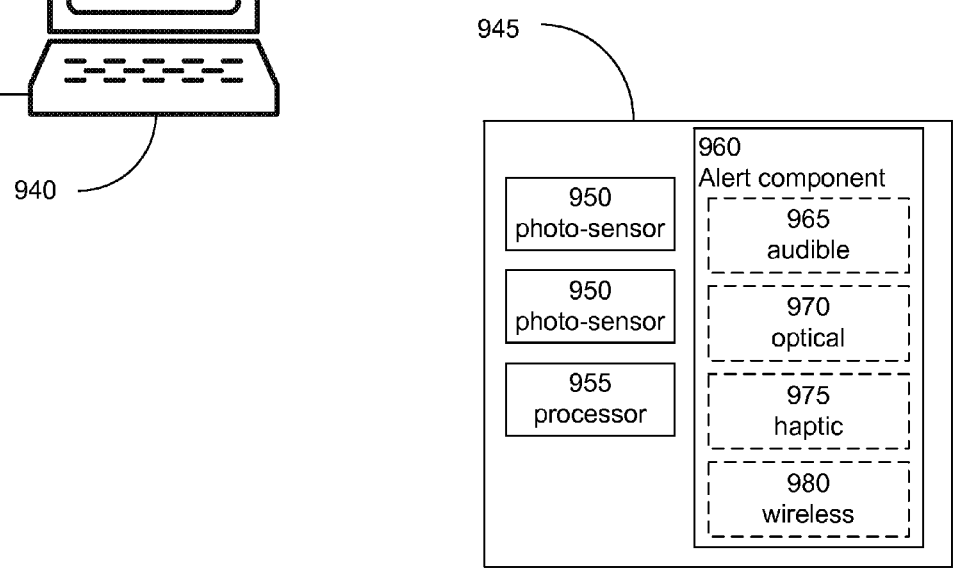

FIG. 9B illustrates further aspects of an injector-tracking device sized for attachment to an injector. Injector-tracking device 945 can include one or more photo-sensors 950. The one or more photo-sensors 950 are operably connected to microprocessor 955 configured to receive one or more signals from the one or more photo-sensors 950 and activate alert component 960. Alert component 960 is configured to output an alert in response to activation of the one or more photo-sensors 950. Alert component 960 can further include one or more of an audible alert component 965, an optical alert component 970, a haptic alert component 975, and/or a wireless alert component 980. In one embodiment, the injector-tracking device includes a processor operable to calculate a distance between the tip of the injector, e.g., the tip of a needle attached to the injector, and the surface of skin at the illuminated injection site.

The injector-tracking device is sized for attachment to an injector. In one embodiment, the injector-tracking device is sized for attachment to the needle shaft of an injector. In one embodiment, the injector-tracking device is sized for attachment to the needle hub or a portion of the syringe attached to the injector. In one embodiment, the injector-tracking device is permanently attached to the injector. In one embodiment, the injector-tracking device is removable, allowing for use on more than one injector. The injector-tracking device may be attached to the injector through one or more of a strap, an adhesive, a sleeve, a clamp, or a clip.

Injector-tracking device 945 includes one or more photo-sensors 950 configured to detect light associated with the one or more illuminated injection sites. The one or more photo-sensors can include one or more complementary metal-oxide-semiconductor (CMOS) sensors, charge coupled device (CCD) sensors, photodiodes, photoresistors, photovoltaic cells, photomultiplier, phototransistors, or quantum dot photoconductors. Photo-sensors are available from a variety of commercial sources (from, e.g., Hamamatsu Photonics, Japan; Advanced Photonix, Inc., Ann Arbor, Mich.; OSI Optoelectronics, Hawthorne, Calif.).

Figure 10A:
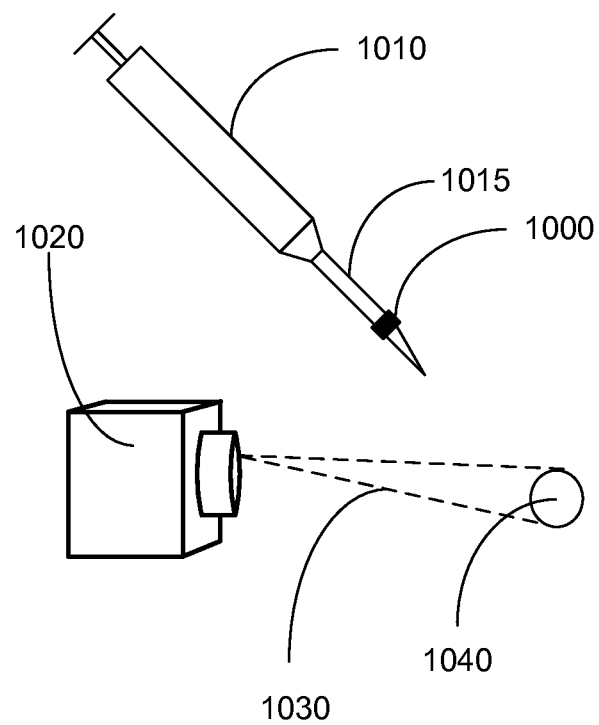
FIGS. 10A & 10B are schematics of an embodiment of an injector-tracking device.
Figure 10B:
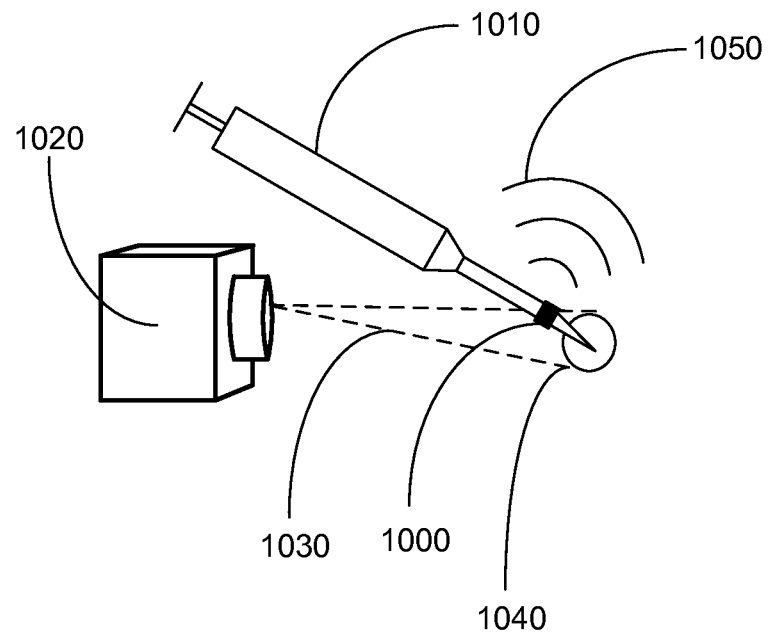

In one embodiment, the alert component of the injector-tracking device includes an audible alert component. The audible alert component includes a speaker for emitting an audible alert. FIGS. 10A and 10B illustrate an embodiment of a system including an injector-tracking device with an audible alert component. In FIG. 10A, injector-tracking device 1000 is attached to injector 1010, in this instance toward the end of needle shaft 1015. Controllable light-emitting element 1020 emits light 1030 to illuminate injection site 1040. Injector-tracking device 1000 is outside light 1030 and not emitting any sound. In FIG. 10B, injector-tracking device 1000 has moved into light 1030 and now emits an audible alert. In one embodiment, the audible alert component is turned on and issues a sound audible to the user when the injector-tracking device has come in appropriate contact with an illuminated injection site. For example, the injector-tracking device may not emit any audible sound until the injector is in the appropriate location, as illustrated in the embodiment of FIG. 10. In one embodiment, the audible alert component changes the tone, frequency, or volume of a continuously emitted sound audible to the user when the injector-tracking device comes in appropriate contact with an illuminated injection site. For example, the injector-tracking device may emit a constant beeping sound, the beeping sound changing in quality, e.g., tone, frequency, or volume, when the injector-tracking device and consequently the associated injector is in the appropriate location. The audible alert component can include one or more of a sound chip, sound card, or a microchip. In one embodiment, the audible alert component can include a piezoelectric speaker. A variety of suitable piezoelectric speakers are available, including from Murata Manufacturing Co., Ltd., (Smyra, Ga.). In one embodiment, an audible alert component can include a piezoelectric speaker configured to generate a beeping noise in response to a signal from the processor and/or photo-sensor.

In one embodiment, the alert component includes an optical alert component. The optical alert component includes one or more elements that emit light. FIGS. 11A and 11B illustrate an embodiment of a system including an injector-tracking device with an optical alert component. In FIG. 11A, injector-tracking device 1100 is attached to injector 1110, in this instance toward the end of needle shaft 1115. Controllable light-emitting element 1120 emits light 1130 to illuminate injection site 1140. Injector-tracking device 1100 is outside light 1130 and not emitting any optical alert, e.g., visible light. In FIG. 11B, injector-tracking device 1100 has moved into light 1130 and now emits an optical alert. In one embodiment, the optical alert component is turned on and emits light visible to the user when the injector-tracking device has come in appropriate contact with an illuminated injection site. For example, the injector-tracking device may not emit light until the injector is in the appropriate location. In one embodiment, the optical alert component changes a color, continuity, or brightness of a continuously or intermittently emitted light when the injector-tracking device comes in appropriate contact with an illuminated injection site. For example, the injector-tracking device may emit a flashing optical signal which changes to continuous emission when the injector-tracking device and consequently the associated injector is in the appropriate location. For example, the injector-tracking device may emit a first color of light, e.g., red light, which changes to a second color of light, e.g., green light, when the injector is in the appropriate location based on detection of the illuminated injection site by the one or more photo-sensors on the injector-tracking device. Examples of light sources for use in an optical alert component include controllable light-emitting diodes, quantum dots, laser diodes, or other relatively small light sources.

In one embodiment, the alert component is a wireless alert component, capable of transmitting a wireless transmission to a receiver. In one embodiment, the alert component includes a transmission unit, non-limiting components of which have been described herein. In one embodiment, the wireless alert component sends a wireless transmission back to the computing device of the system. The computing device in turn may change the quality of the light emitted from the controllable light-emitting elements to indicate that an injection has been successfully completed at a given spot. For example, the color or pattern of light illuminating an injection site may change in response to a wireless signal from the injector-tracking device. In one embodiment, the wireless alert component sends a wireless transmission back to another device, e.g., a head-set, a hand-held device, an ear-piece, a display, or other device capable of receiving a wireless transmission and sending an audible or visible alert to the user.

Figure 12:
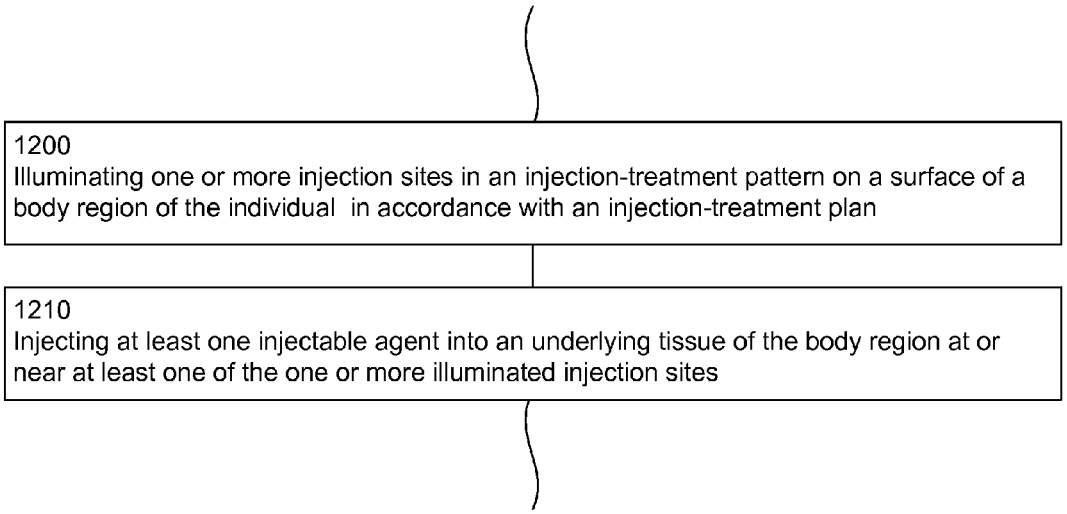
FIG. 12 is a flowchart of a method of guiding injection in an individual.

FIG. 12 illustrates a method for guiding injection in an individual. Block 1200 shows illuminating one or more injection sites in an injection-treatment pattern on a surface of a body region of the individual. Illuminating one or more injection sites in an injection-treatment pattern on a specific body region of the individual is dependent upon the condition being treated and the injection-treatment plan. For example, specific treatment of the individual's face or the individual's neck would necessitate illuminating one or more injection sites in an injection-treatment pattern on a face or neck, respectively. In another example, a self-injection injection-treatment plan that includes intramuscular injections, e.g., antibiotic or fertility treatment, may include illuminating one or more injection sites on any of a number of body regions easily accessible to the individual, e.g., the thigh or abdomen areas. Block 1210 of FIG. 12 depicts injecting at least one injectable agent into an underlying tissue of the body region of the individual at or near at least one of the one or more illuminated injection sites. The one or more injection sites can be illuminated by one or more controllable light-emitting elements configured to emit non-destructive light, the one or more controllable light-emitting elements controlled by a computing device including a process as described herein.

FIG. 13 depicts further aspects of the method illustrated in FIG. 12 for guiding injection in an individual. FIG. 13 includes block 1300. Block 1300 shows optionally illuminating the one or more injection sites on the surface of a face, torso, abdomen, head, neck, upper extremity, lower extremity, or buttocks region of an individual. In general, injection sites may be illuminated on any portion of the body accessible to injection by a user, e.g., a physician or other practitioner, or the individual in the case of self-injection.

FIG. 13 further includes block 1310. Block 1310 depicts optionally illuminating the one or more injection sites on the surface of the body region of the individual with one or more controllable light-emitting elements configured to emit non-destructive light. Block 1310 further includes optional block 1320. Block 1320 depicts optionally illuminating the one or more injection sites on the surface of the body region of the individual with one or more of a controllable light-emitting diode, laser, laser diode, collimated light source, projector, or focused light source configured to emit non-destructive light. Non-limiting examples of controllable light-emitting elements have been described above herein.

FIG. 13 further includes block 1330. Block 1330 depicts optionally illuminating the one or more injection sites on the surface of the body region of the individual with one or more controllable light-emitting elements mounted on a head region of the user, the one or more controllable light-emitting elements configured to emit non-destructive light. In one embodiment, the user is a physician or other practitioner performing injection on an individual. In one embodiment, the user is an individual performing self-injection. Embodiments of a system for illuminating injection sites using controllable light-emitting elements mounted on a head region of a user have been described above herein and an embodiment illustrated in FIG. 6.

FIG. 13 further includes block 1340. Block 1340 shows optionally autonomously illuminating the one or more injection sites using a computing device operably connected to one or more controllable light-emitting elements, the computing device accessing a stored injection-treatment plan and controlling illumination from the one or more controllable light-emitting elements to illuminate the one or more injection sites on the surface of the body region of the individual in accordance with the stored injection-treatment plan. In one embodiment, the injection-treatment plan is specific to the individual. In one embodiment, the injection-treatment plan is specific to a condition being treated.

FIG. 14 depicts further aspects of the method illustrated in FIG. 12 for guiding injection in an individual. FIG. 14 includes block 1400. Block 1400 depicts optionally illuminating the one or more injection sites on the surface of the body region of the individual with one or more of a color or pattern of light. Block 1400 further includes blocks 1410 and 1420. Block 1410 shows optionally illuminating the one or more injection sites on the surface of the body region of the individual with one or more of a crosshair, ring, circle, or concentric circles. Block 1420 shows optionally illuminating the one or more injection sites on the surface of the body region of the individual with one or more of a letter, number, symbol, or shape. Methods for illuminating a surface with a pattern of light include using diffusers, filters, and/or projected images have been described above herein.

FIG. 14 further includes optional block 1430. Block 1430 depicts wherein the one or more of the color or pattern of light is representative of at least one injection-treatment parameter. Block 1430 further includes optional block 1440. Block 1440 depicts wherein the at least one injection-treatment parameter comprises at least one of an injection site, a type of injectable agent, a type of injector, a dosage of an injectable agent, a sequence of dosing an injectable agent, a timing of dosing an injectable agent, an injection depth, or an injection angle.

Figure 15:
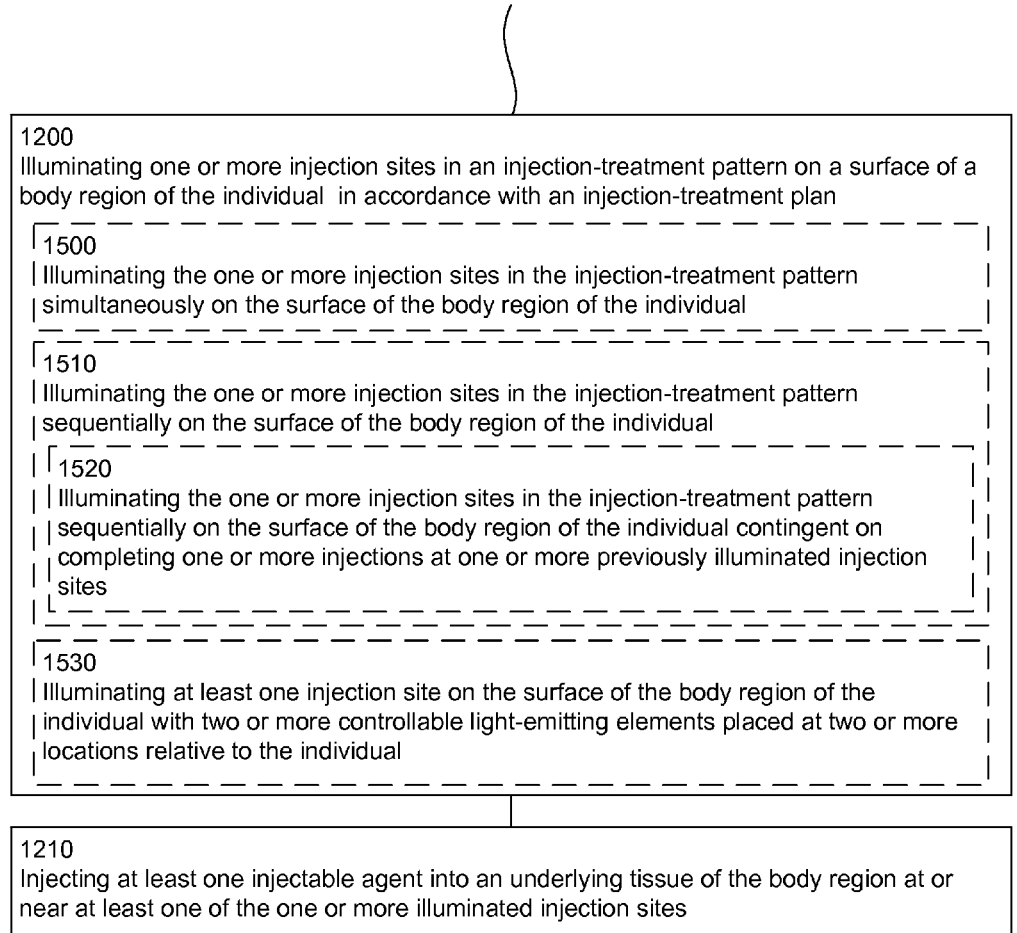
FIG. 15 is a flowchart depicting aspects of a method such as illustrated in FIG. 12.

FIG. 15 shows further aspects of the method of FIG. 12 for guiding injection in an individual. FIG. 15 includes block 1500. Block 1500 depicts optionally illuminating the one or more projected injection sites in the injection-treatment pattern simultaneously on the surface of the body region of the individual. In one embodiment, all of the one or more injection sites are illuminated at the same time. In one embodiment, each injection site is illuminated with light emitted from a single controllable light-emitting element. In one embodiment, all of the one or more injection sites are illuminated simultaneously with light emitted from a projector, projecting an image onto the body surface that includes the entirety of the illuminated injection sites. FIG. 15 further includes block 1510. Block 1510 depicts optionally illuminating the one or more injection sites in the injection-treatment pattern sequentially on the surface of the body region of the individual. In one embodiment, sequentially illuminating the one or more injection sites is accomplished using a single controllable light-emitting element that alters the beam of emitted light so as to alter the location of illumination on the surface of the body region. In one embodiment, a sequence of illuminated injection sites is generated by sequentially activating a series of controllable light-emitting elements that sequentially illuminate different locations on the surface of the body region. In one embodiment, a sequence of illuminated injection sites is generated by projecting onto the surface of the body region a sequentially changing image, e.g., a series of images in which digitally registered injection sites associated with the images sequentially appear and disappear according to an injection-treatment plan. Block 1510 of FIG. 15 further includes optional block 1520. Block 1520 illustrates optionally illuminating the one or more injection sites in the injection-treatment pattern sequentially on the surface of the body region of the individual contingent on completing one or more injections at one or more previously illuminated injection sites. In one embodiment, completion of one or more injections at a specific illuminated injection site is monitored with an image capture device. The injector itself may include a sensor, e.g., a photo-sensor, which activates when the injector is in the vicinity of the beam of light illuminating an injection site. Once the system determines that an injection has occurred at a given illuminated injection site, the next injection site in the sequence is illuminated and available for injection.

FIG. 15 further includes block 1530. Block 1530 depicts optionally illuminating at least one injection site on the surface of the body region of the individual with two or more controllable light-emitting elements placed at two or more locations relative to the individual. It is contemplated that during the course of injecting an injectable agent at an illuminated injection site, the user, e.g., a physician, other practitioner, or the individual may disrupt the beam of light illuminating an injection site. In one embodiment, it may be preferable to illuminate one or more injection sites from more than one locations relative to the individual such that if the user performing the injections blocks illumination from one source, e.g., by getting one's head or hand in the way of the light emitted from one of the one or more controllable light-emitting elements, the illuminated injection site will still be visible on the surface of the body region from a second, unblocked source. As such, a redundancy in illumination is contemplated in which multiple beams of light from multiple locations illuminate an injection site with at least one of the beams of light illuminating a given injection site at any point during the injection-treatment session despite movement by the physician or other user that might disrupt any one of the multiple beams of light. An example of an embodiment of a system for illuminating an injection site on the surface of the body region of an individual with two or more controllable light-emitting elements is illustrated in FIG. 5.

Figure 16:
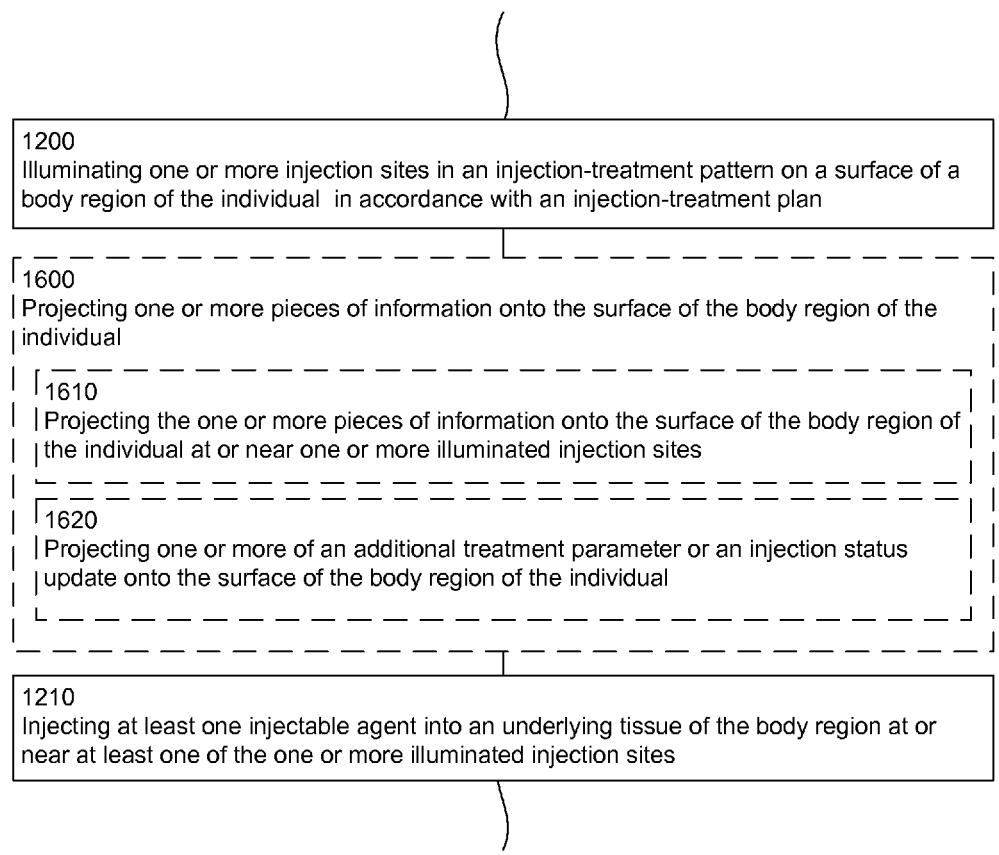
FIG. 16 is a flowchart illustrating aspects of a method such as shown in FIG. 12.

FIG. 16 shows further aspects of the method of FIG. 12 for guiding injection in an individual. FIG. 16 shows that in one embodiment, the method of FIG. 12 can optionally include block 1600. Block 1600 shows optionally projecting one or more pieces of information onto the surface of the body region of the individual. Block 1600 further includes optional blocks 1610 and 1620. Block 1610 shows optionally projecting the one or more pieces of information onto the surface of the body region of the individual at or near one or more illuminated injection sites. Block 1620 shows optionally projecting one or more additional treatment parameters or an injection status update onto the surface of the body region of the individual. In an embodiment, the one or more pieces of information, e.g., one or more additional treatment parameters, are meant to annotate the illuminated injection sites to provide additional information to the user performing the injections as to the type of injectable agent, the dosage, the type of injector, the depth or angle of injection, and/or the sequence or timing of injection. In an embodiment, the one or more pieces of information are not projected with any specific illuminated injection site, but provide information that might be applicable to all of the injection sites. For example, a general piece of information including the type of drug and the dosage may be projected on the body region indicating to the user that all of the illuminated injection sites are to be injected with the same drug at the same dosage. In an embodiment, the one or more pieces of information may provide an injection status update, e.g., a running clock, the number of injections completed and/or remaining, or other pieces of information pertinent to an injection treatment session.

Figure 17:
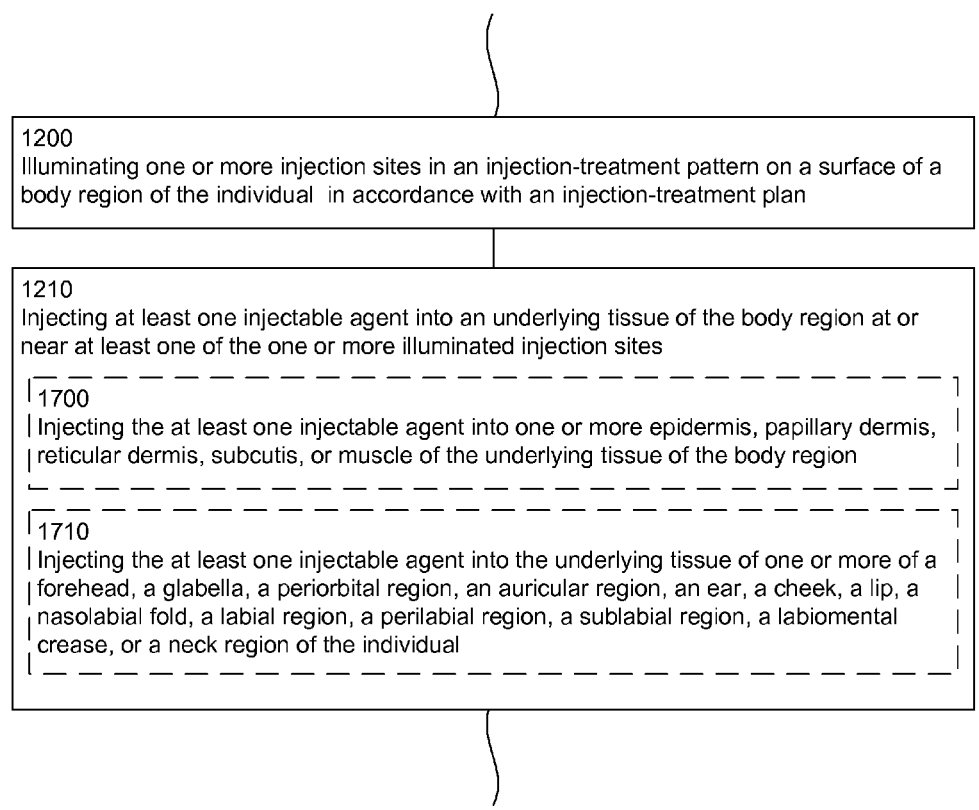
FIG. 17 is a flowchart showing aspects of a method such as depicted in FIG. 12.

FIG. 17 shows further aspects of the method of FIG. 12 for guiding injection in an individual. FIG. 17 illustrates that in one embodiment, block 1210 can include one or more of optional blocks 1700 and 1710. Block 1700 depicts optionally injecting the at least one injectable agent into one or more of epidermis, papillary dermis, reticular dermis, subcutis, or muscle of the underlying tissue of the body region at or near at least one of the one or more illuminated injection sites. For example, the method can include injecting one or more doses of *botulinum* neurotoxin into the papillary dermis at one or more illuminated injection sites on an individual's forehead region. For example, the method can include injecting one or more doses of fertility hormones into the muscle at one or more illuminated injection sites on the surface of an individual's upper thigh. In one embodiment, the method can include injecting the at least one injectable agent into one or more lines, wrinkles or folds on an individual's face, e.g., as part of a cosmetic treatment. Block 1710 depicts optionally injecting the at least one injectable agent into the underlying tissue of one or more of a forehead, a glabella, a periorbital region, a preauricular region, an ear, a cheek, a lip, a nasolabial fold, a labial region, a perilablial region, a sublabial region, a labiomental crease, or a neck region of the individual. For example, the method can include injecting one or more doses of collagen at one or more illuminated injection sites on the nasolabial folds of an individual's face.

FIG. 18 shows further aspects of the method of FIG. 12 for guiding injection in an individual. FIG. 18 illustrates that in one embodiment, block 1210 can include one or more of optional blocks 1800, 1810, 1820, 1830, 1840 and 1850. Block 1800 depicts optionally injecting at least one neurotoxin. In one embodiment, the at least one neurotoxin can include one or more forms of the neuromuscular blocking agent *botulinum* toxin. In one embodiment, *botulinum* toxin is used for treating wrinkles in a facial region of an individual. For example, the one or more illuminated injection sites can be used for guiding injection *botulinum* toxin into wrinkles associated with the forehead, e.g., glabellar frown lines, of an individual's face. In one embodiment, *botulinum* toxin is used for treating one or more of primary axillary hyperhidrosis (excessive sweating), blepharospasm (eye twitching), strabismus (cross-eyed), cervical dystonia, chronic migraine, and upper limb spasticity. Non-limiting examples of *botulinum* toxin for use as an injectable agent include onabotulinumtoxinA, abotulinumtoxinA, incobotulinymtoxinA, rimabotulinumtoxinB and like agents (see, e.g., Park et al., *Clin. Ophthalmol.* (2011) 5:725-732, which is incorporated herein by reference).

Block 1810 of FIG. 18 depicts optionally injecting at least one of a subcutaneous volume enhancer or dermal filler at or near at least one of the one or more illuminated injection sites. Block 1810 further includes optional blocks 1820, 1830, and 1840. Block 1820 illustrates optionally injecting at least one of a collagen filler into an underlying tissue of the body region of the individual at or near at least one of the one or more illuminated injection sites. For example, the one or more illuminated injections sites can be used for guiding injection of a collagen filler into the upper or lower lip of an individual to achieve lip augmentation. Other non-limiting examples of injecting collagen filler include injecting into the grooves and/or lines that form wrinkles and sagging skin of the face. In one embodiment, the at least one collagen filler can be used to treat depressed scars, e.g., pitted acne scars. Non-limiting examples of bovine-, porcine-, or human-derived collagen fillers are available and are sold under their trademarked names ARTEFILL, COSMO- PLAST, COSMODERM, EVOLENCE, ZYDERM, and ZYPLAST. For example, ZYPLAST can be injected using a 30-gauge needle into the middle and deep reticular dermis to correct deeper lines and wrinkles or for lip augmentation. The depth of injection can vary from superficial/papillary dermis for treatment of wrinkles and fine lines to mid to deep dermis for treatment of moderate to deep facial wrinkles and folds (see, e.g., Hanke et al., *J. Am. Acad. Dermatol.* (2011) 64:S66-85, which is incorporated herein by reference).

Block 1830 of FIG. 18 depicts optionally injecting at least one of a hyaluronic acid filler into an underlying tissue of the body region of the individual at or near at least one of the one or more illuminated injection sites. For example, the one or more illuminated injections sites can be used for guiding injection of at least one hyaluronic acid filler into an underlying tissue of a body region to temporarily smooth wrinkles, augment lips, reduce facial folds, and attenuate scars. A variety of hyaluronic fillers are available and are sold under their trademarked names, including BELOTERO BALANCE (Merz Aesthetics, San Mateo, Calif.); HYALAFORM, JUVEDERM ULTRA and JUVEDERM ULTRA PLUS (Allergan, Inc., Irvine, Calif.); PERLANE and RESTYLANE (Medicis Pharmaceutical Corp., Scottsdale, Ariz.); and PREVELLE and PURAGEN (Mentor Worldwide, LLC, Santa Barbara, Calif.). Hyaluronic acid can be injected with needles ranging in size from 27 to 30 gauge to a depth ranging from the mid to deep dermis to the superficial subcutaneous space (see, e.g., Allemann & Baumann *Clinical Interventions in Aging* (2008) 3:629-634; Brandt & Cazzaniga *Clinical Interventions in Aging* (2008) 3:153-159, which are incorporated herein by reference).

Block 1840 of FIG. 18 depicts optionally injecting at least one of adipose, fibroblasts, calcium microspheres, or poly L lactic acid into an underlying tissue of the body region of the individual at or near at least one of the one or more illuminated injection sites. In one embodiment, adipose tissue can be isolated from one region of the individual's body, e.g., the abdomen or thigh, and reinjected into another region of the individual's body, e.g., the face, to augment or repair features of the facial region (see, e.g., Meier et al., *Arch. Facial Plast. Surg.* (2009) 11:24-28, which is incorporated herein by reference). In one embodiment, fibroblasts can be isolated from the individual, expanded in vitro, and reinjected into the individual (see, e.g., U.S. Pat. No. 7,846,465, which is incorporated herein by reference). In one embodiment, calcium hydroxyapatite microspheres, sold under the trademark RADIESSE (Merz Aesthetics, San Mateo, Calif.), can be injected using a 27 gauge needle, e.g., to correct moderate to severe nasolabial folds. The calcium hydroxyapatite microspheres can be injected with an aqueous gel, the latter of which is highly viscous, requiring a larger bore needle, e.g., a 27 gauge needle. The gel degrades over the course of several months, leaving behind the calcium microspheres to stimulate collagen synthesis. In one embodiment, poly L lactic acid (PLLA, sold under the trademark SCULPTRA by Sanofi-Aventis U.S. LLC, Bridgewater, N.J.) can be injected at or below the level of the dermal-subcutaneous junction for augmentation of the lower two-thirds of the face in individuals with lipoatrophy associated with HIV infection. PLLA can also be used for cosmetic purposes as a deep dermal filler (see, e.g., Sherman *Clin. Dermatol.* (2009) 27:S23-S32, which is incorporated herein by reference). PLLA is viscous solution and as such requires injection using larger bore needles, e.g., 25- or 26-gauge needles. In one embodiment, PLLA may be used in conjunction with lidocaine and/or epinephrine to lessen the pain of injection with a relatively large needle. For example, lidocaine and/or epinephrine can be included in the injection along with the PLLA.

Block 1850 of FIG. 18 depicts optionally injecting at least one of insulin, an antibiotic, a hormone, a chemotherapeutic agent, cells, an anti-inflammatory agent or a biological agent into an underlying tissue of the body region of the individual at or near at least one of the one or more illuminated injection sites. In one embodiment, injecting at least one of insulin includes injecting at least one of rapid acting insulin, short-acting insulins, intermediate-acting insulins, premixed insulins, or long-acting insulins. Commercial sources of insulin are available from, e.g., Eli Lilly (Indianapolis, Ind.), Sanofi-Aventis U.S. LLC (Bridgewater N.J.), Novo Nordisk Inc. (Princeton, N.J.), or Pfizer (New York, N.Y.).

In one embodiment, injecting at least one antibiotic includes injecting at least one of penicillins, e.g., penicillin, ampicillin, piperacillin; cephalosporins and other beta-lactam drugs, e.g., cefazolin, ertapenem; tetracyclines, e.g., doxycycline; macrolides, e.g., erythromycin; clindamycin; aminoglycosides, e.g., streptomycin, gentamicin; spectinomycin; sulfonamides; quinolones and fluoroquinolones.

In one embodiment, injecting at least one hormone includes injecting at least one of a hypothalamic or pituitary hormone, synthetic analogs, and/or antagonist thereof, e.g., adrenocorticotropic hormone, corticotropin-releasing hormone, follicle stimulating hormone, gonadotropin-releasing hormone and synthetic analogs, luteinizing hormone, prolactin; at least one of an adrenocoricosteroid, synthetic analogs, and/or antagonists thereof, e.g., dexamethasone, hydrocortisone, prednisolone, methylprednisolone, triamicinolone; gonadal hormones, e.g., estrogens, progestins, androgens, and anabolic steroids; glucagon and analogs thereof.

In one embodiment, injecting at least one cancer chemotherapeutic or associated therapy includes injecting at least one of alpha interferon, erythropoietin and derivatives thereof, colony stimulating factor and analogs thereof, somatostatin and analogs thereof.

In one embodiment, injecting at least one biological agent includes injecting at least one of teriparatide, etanercept, interferon, abatacept, anakinra, bevacizumab, cetuximab, cyclophosphamide, gemtuzumab, muromonab-CD3, omalizumab, pegademase, immune globulin, tacrolimus, or tositumomab.

In one embodiment, injecting at least one of cells includes injecting stem cells, differentiated cells, adipose, fibroblasts, myocytes, inflammatory cells, neural cells, or any other cell type that can be injected into an individual for use in treating a condition.

In one embodiment, injecting at least one anti-inflammatory agent includes injection of one or more steroidal compound, e.g., one or more corticosteroids. In one embodiment, injecting at least one anti-inflammatory agent includes injecting at least one non-steroidal anti-inflammatory agent, non-limiting examples of which include aspirin, COX-2 inhibitor, indomethacin, diclofenac, naproxen, and ibuprofen.

In one embodiment, the at least one injectable agent is injected into the muscle of the underlying tissue of the body region of the individual. Non-limiting examples of injectable agents that are injected intramuscularly include neurotoxins, codeine, morphine, methotrexate, metoclopramide, olanzapine, streptomycin, diazepam, prednisone, penicillin, interferon beta-1a, testosterone, estradiol, dimercaprol, ketamine, Lupron, maloxone, quinine, vitamin B12, Gardasil, hepatitis A vaccine, rabies vaccine, and influenza vaccine. In one embodiment, the at least one injectable agent is injected subcutaneously. Non-limiting examples of injectable agents that are injected subcutaneously include insulin, morphine, diacetylmorphine, and goserelin. In one embodiment, the at least one injectable agent is injected intradermally. Non-limiting examples of injectable agents that are injected intradermally include influenza vaccines, tuberculosis skin tests, and allergy shots.

In one embodiment, the at least one injectable agent is injected in combination with one or more analgesic agents, for example lidocaine, to lessen the pain associated with injection. For example, ZYDERM (from, e.g., McGhan Medical Corporation, Fremont, Calif.) is a collagen filler that includes the analgesic lidocaine.

In one embodiment, the method further includes applying one or more topical agents to the surface of the body region of the individual prior to, during, and/or after injection treatment. The one or more topical agents can include one or more analgesics, disinfectants, antiseptics, sterilants, therapeutic agents, or combinations thereof. Non-limiting examples of analgesics include lidocaine, prilocaine, tetracaine, cocaine, pramoxine, dibucaine, benzocaine, dyclonine, a NSAID, or an opiate. For example, lidocaine, either alone or in combination with prilocaine as a eutectic mixture (2.5% lidocaine/2.5% prilocaine) can be used to ease the acute pain of needle insertion (see, e.g., McCleane, Curr. Opin. Anesthesiol., (2010) 23:704-707; Kundu & Achar, Am. Fam. Physician (2002) 66:99-102, which are incorporated herein by reference). In one embodiment, the at least one analgesic can include one or more of a vapocoolant or skin refrigerant, e.g., menthol; ethyl chloride; dichlorodifluromethane mixed with trichloromonofluoromethane; or pentafluoropropane mixed with tetrafluoroethane; and the like. Non-limiting examples of disinfectants, antiseptics and/or sterilants include isopropanol, silver compounds, ethanol, povidone, iodine, glutaraldehyde, formaldehyde, chlorhexidine gluconate, sodium hypochlorite, quaternary ammoniums compounds, hydrogen peroxide, and phenols. Non-limiting examples of therapeutic agents for topical use include retinoids, corticosteroids, and chemotherapeutics.

In one embodiment, the one or more topical agents include one or more antimicrobial agents. The one or more antimicrobial agents can further include at least one of an antibacterial agent, antiviral agent, or antifungal agent. In one embodiment, the at least one antimicrobial is configured to prevent or minimize infection associated with the injection treatment. In one embodiment, the at least one antimicrobial agent is configured to treat or prevent or minimize other infections on the individual's skin. Non-limiting examples of antibacterial agents commonly used for topical applications include benzoyl peroxide, sodium sulfacetamide, erythromycin, mupirocin, retapamulin, bacitracin, neomycin, polymyxin b/e, silver sulfadiazine, or tetracycline. Non-limiting examples of antiviral agents commonly used for topical applications include acyclovir, docosanol, famciclovir, imiquimod, penciclovir, valacyclovir, and vidarabine. Non-limiting examples of antifungal agents commonly used for topical applications include amphotericin B, butaconazole, butenafine, ciclopirox olamine, clotrimazole, econazole, ketoconazole, miconazole, naftifine, natamycin, nystatin, oxiconazole, sulconazole, terbinafine, terconazole, tioconazole, tolnaftate, and metronidazole.

In one embodiment, the surface temperature of the body region of the individual may be altered above or below about 98.6° F. (or above or below about 37° C.) prior to, during, and/or after one or more injections. In one embodiment, the surface of the body region is cooled below about 98.6° F. (37° C.) prior, during and/or after injection with an injectable agent. Cooling the body region may lessen the pain associated with needle injection and/or prevent swelling and/or bruising post injection. In one embodiment, the surface of the body region is cooled by placing a cooling element, e.g., an ice pack, a chemical ice pack, or a chilled object with a high heat capacity, onto the body region of an individual. The cooling temperature can range from about 10° C. to about 0° C. It is understood that the cooling temperature can fall outside this range, but is contemplated to be sufficiently cool enough to reduce pain and swelling but not so cold as to be painful to the underlying tissue of the body region.

In one embodiment, the surface of the body region is heated above about 98.6° F. (37° C.) prior, during and/or after injection with an injectable agent. Heating the body region may increase vasodilation and/or circulation in the underlying tissue. In one embodiment, the surface of the body region is heated by placing a heating element, e.g., a chemical heating pack, or a heated object with a high heat capacity, onto a body region of an individual. In one embodiment, the surface of the body region is heated using the one or more controllable light-emitting elements. The heating temperature can range from about 40° C. to about 45° C. It is understood that the heating temperature can fall outside this range, but is contemplated to be sufficiently warm enough to increase circulation but not so warm as to be painful, damaging, or destructive to the skin, eyes, or underlying tissue of a body region.

Figure 19:
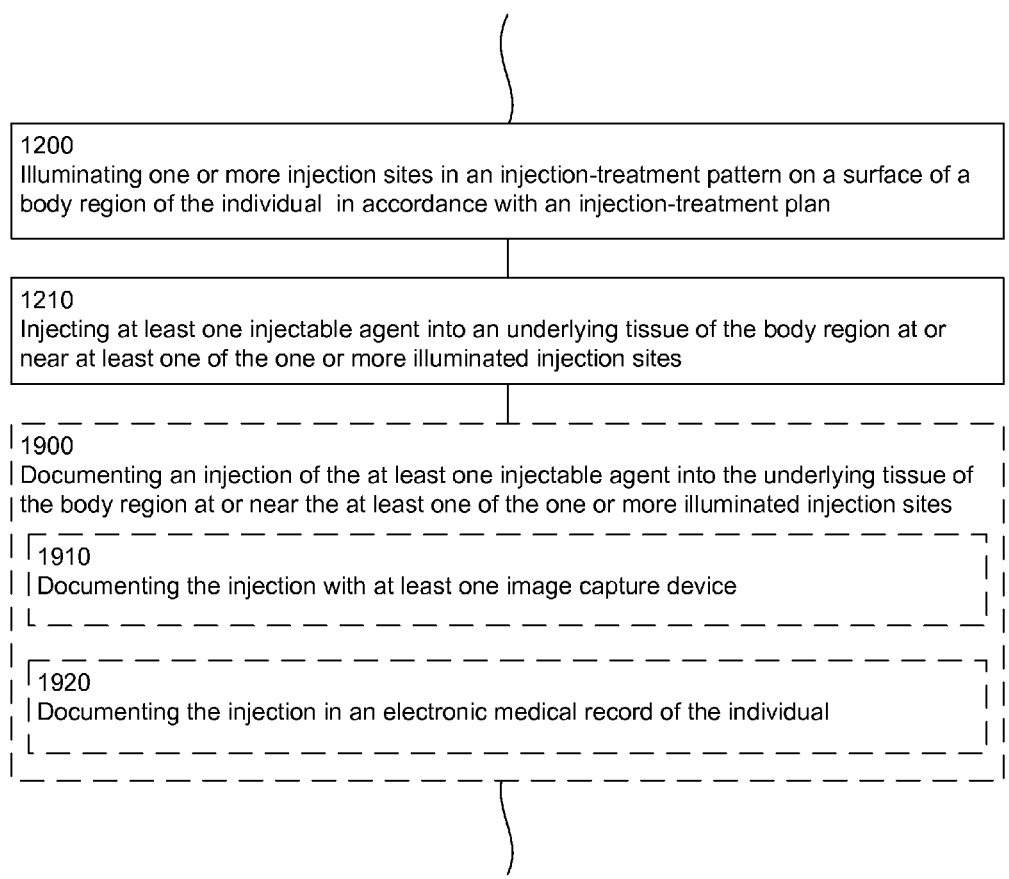
FIG. 19 is a flowchart illustrating aspects of a method such as shown in FIG. 12.

FIG. 19 illustrates further aspects of the method of FIG. 12 for guiding injection in an individual. FIG. 19 includes block 1900. Block 1900 depicts optionally documenting an injection with the at least one injectable agent into the underlying tissue of the body region at or near the at least one or more illuminated injection sites. Documenting the injection can include documenting where the injection was made on the body region, the type of injectable agent used for the injection, the dosage of injectable agent used at each injection site, the sequence of injecting the injectable agent at more than one site, the timing of injecting the injectable agent, the angle of injection and the depth of injection. Documenting can further include documenting how the individual responded to the injection, e.g., any side effects such as redness, swelling, treatment outcome and/or over-correction of a cosmetic condition.

Block 1900 further includes optional blocks 1910 and 1920. Block 1910 shows optionally documenting the injection with at least one image capture device. Documenting the injection with the at least one image capture device can include documenting the condition of the body region before and after injection, any visible adverse reactions to the injection, e.g., swelling and/or redness, the actual act of injecting at an illuminated injection site, injection misses, injection errors, treatment outcome, and the like. Block 1920 shows optionally documenting the injection in an electronic medical record of the individual. Documenting the injection in an electronic medical record can include dictating into the electronic medical record, typing into an electronic medical record, and/or transmitting one or more images or video documenting the injection from an image capture device to the individual's electronic medical record. In one embodiment, documenting the injection may include a sensor on the injector that interacts with the illuminated injection sites and wirelessly transmits information regarding the injection process to the electronic medical record.

Figure 20:
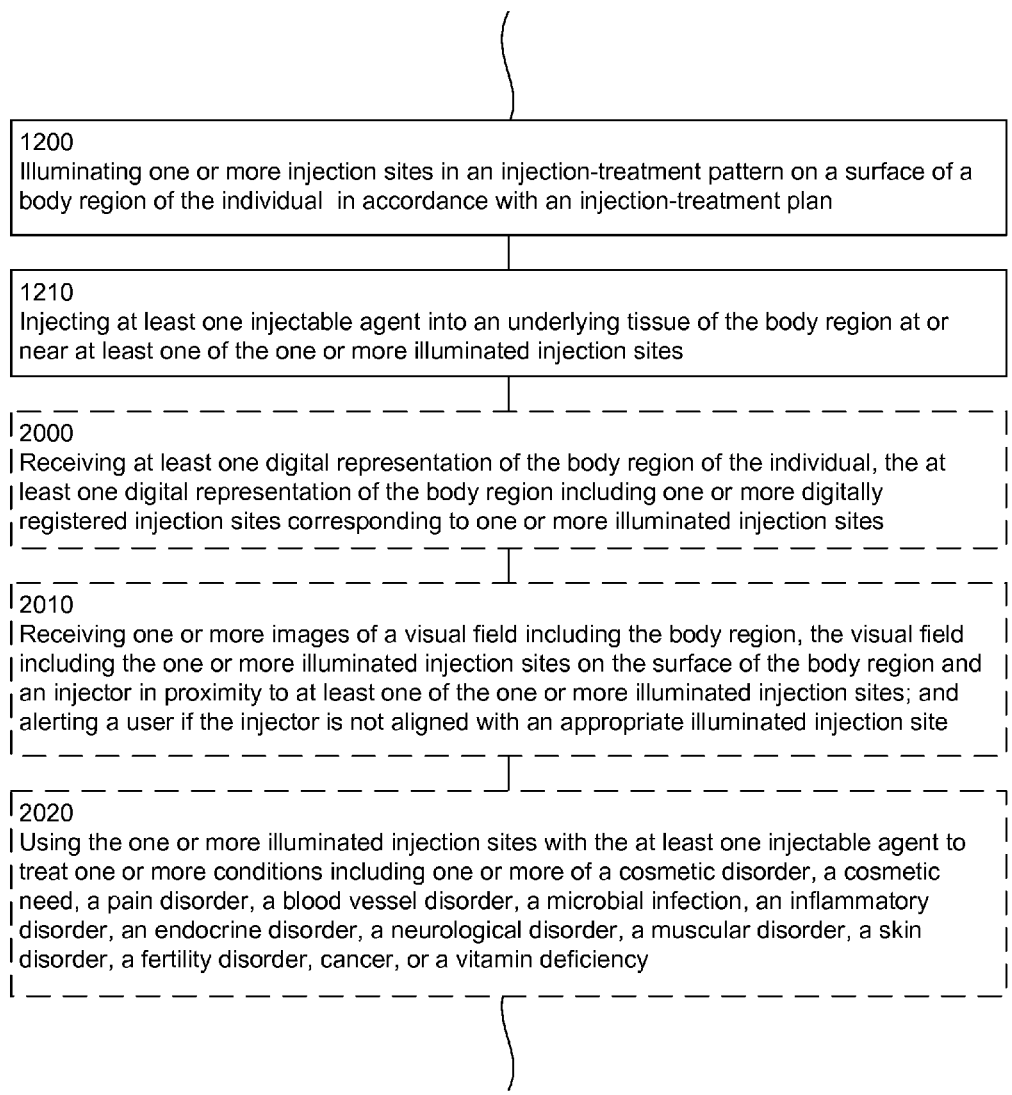
FIG. 20 is a flowchart showing aspects of a method such as depicted in FIG. 12.

FIG. 20 illustrates further aspects of the method of FIG. 12 for guiding injection in an individual. FIG. 20 includes block 2000. Block 2000 shows optionally receiving at least one digital representation of the body region of the individual, the at least one digital representation of the body region including one or more digitally registered injection sites corresponding to the one or more illuminated injection sites. The digital representation can be received through a wired or wireless transmission from a computing device. In one embodiment, the digital representation is received directly from one or more image capture device.

FIG. 20 further includes block 2010. Block 2010 shows optionally receiving one or more images of a visual field including the body region, the visual field including the one or more illuminated injection sites on the surface of the body region and an injector in proximity to at least one of the one or more illuminated injection sites, and alerting a user if the injector is not aligned with an appropriate illuminated injection site.

In one embodiment, a method for guiding injection in an individual further includes verifying whether an injection-treatment plan including one or more illuminated injection sites is appropriate for a given individual based on one or more patient identifiers. In one embodiment, this may include using a form of facial recognition software in combination with the one or more physical registration landmarks, e.g., a unique pattern of freckles or other pigmented areas. As such, the ability to align digital registration landmarks associated with a digital representation of a body region with a unique pattern of physical registration landmarks on the body region of an individual can be used to determine whether the digital representation is being used with the appropriate individual.

FIG. 20 further includes block 2020. Block 2020 illustrates optionally using the one or more illuminated injection sites with the at least one injectable agent to treat one or more conditions including one or more of a cosmetic disorder, a cosmetic need, a pain disorder, a blood vessel disorder, a microbial infection, an inflammatory disorder, an endocrine disorder, a neurological disorder, a muscular disorder, a skin disorder, a fertility disorder, cancer, or a vitamin deficiency.

Systems and methods are described herein for generating an injection guide including one or more illuminated injection sites.

FIG. 21 illustrates a method implemented on a computing device for generating an injection guide. Block 2100 shows receiving one or more digital images of a body region of an individual, the body region including one or more physical registration landmarks. Block 2110 shows generating at least one digital representation of the body region using the one or more digital images, the at least one digital representation including one or more digital registration landmarks corresponding to the one or more physical registration landmarks on the body region. Block 2120 shows adding one or more digitally registered injection sites to the at least one digital representation of the body region in an injection-treatment pattern, the one or more digitally registered injection sites registered relative to the one or more digital registration landmarks. Block 2130 shows generating one or more output signals having information for controlling one or more controllable light-emitting elements to illuminate a location on a surface of the body region of the individual corresponding in location to at least one of the one or more digitally registered injection sites.

In one embodiment, the method includes receiving one or more digital images of a face, neck, head, torso, abdomen, upper extremity, lower extremity, or buttocks region of an individual. In general the method can include receiving one or more digital images of any portion of the body accessible to injection with an injector. As defined herein, receiving digital images includes receiving any digital information related to the body region of the individual and the underlying tissue. In one embodiment, receiving one or more digital images of the body region of an individual includes receiving one or more images of the surface topography of the body region. The topography of the body region can include both the micro-topography, e.g., the texture and/or pattern of the skin surface, and the macro-topography, e.g., anatomical features such as nose, lips, cheeks, large wrinkle, joints, and the like.

The method further includes receiving one or more digital images of a body region including one or more physical registration landmarks. In one embodiment, the one or more physical registration landmarks comprise one or more markings placed on the surface of the body region of the individual prior to acquiring the one or more digital images. For example, one or more markings, e.g., a removable ink or adhesive pieces, may be placed on the surface of the body region of an individual prior to acquiring one or more digital images of the body region with an image capture device, e.g., a camera. In one embodiment, the one or more physical registration landmarks comprises one or more of pigmentation, pigmented areas, tattoos, scars, blemishes, anatomical features, or subsurface blood vessels associated with the body region of the individual.

In one embodiment, receiving the one or more digital images of the body region of an individual can include receiving one or more digital images of features of the body region that are themselves the focus of treatment, for example a scar (e.g., an acne scar) or other blemish on the surface of the skin. For example, one or more digital images of a scar on the body region can aide in determining where the one or more digitally registered injection sites should be added to the digital representation of the body region for injection treatment of the scar. As an example, injectable dermal fillers can be used to raise depressions in the surface of the skin caused by severe acne scarring.

In one embodiment, receiving the one or more digital images of the body region can include receiving one or more digital images of body region features contraindicated as sites of injection. For example, injecting a neurotoxin, e.g., *botulinum* toxin, or other injectable agents directly into a blood vessel may lead to unwanted systemic complications. As such, an injection-treatment plan that includes *botulinum* toxin injection, for example, would necessarily avoid overlaying the one or more digitally registered injection sites representative of illuminated injections sites over one or more blood vessels associated with the body region. In an embodiment, one or more of the superficial blood vessels on the body region can be imaged and incorporated into the at least one digital representation of the body region. Non-limiting examples of non-invasive imaging techniques for superficial blood vessels include photoacoustic imaging, ultrasound, near-infrared imaging (see, e.g., Wieringa et al., *Ann Biomed Eng* (2006) 34:1870-1878, which is incorporated herein by reference). Images of superficial blood vessels generated using one or more of these methods can be combined with the images of the body region of the individual to aid in determining an injection-treatment plan and placement of the one or more digitally registered injection sites.

The one or more physical registration landmarks are represented by digital registration landmarks in the digital representation of the body region and are used to register the digitally registered injection sites representative of illuminated injection sites to a physical area on the body region.

FIG. 22 illustrates further aspects of the method of FIG. 21 for generating an injection guide. Block 2100 optionally includes blocks 2200, 2210, 2220, and 2230. Block 2200 shows optionally receiving the one or more digital images of the body region from a data storage device. For example, the one or more digital images may be received from a data storage device incorporated in a computing device. In one embodiment, the one or more digital images are received from a data storage device in a remote computing device. In one embodiment, the one or more digital images can be received from a flash drive or other portable data storage device. In one embodiment, the one or more digital images are received from a data storage device incorporated into an image capture device.

Block 2210 shows optionally receiving the one or more digital images of the body region from one or more of a camera, active scanner, or passive scanner. The one or more digital images of the body region can be received from one or more cameras, active scanners, or passive scanners positioned at one or more locations relative to the individual. For example, multiple images received from multiple directions will allow for obtaining information from all sides of the individual. In one embodiment, the one or more digital images are received with sufficient digital information to differentiate between the color of the skin and other skin features, e.g., freckles, tattoo, moles, or blemishes, the latter of which can be used as physical registration landmarks.

In one embodiment, the one or more digital images are received from at least one active scanner. An active scanner emits some form of radiation or light which when beamed on an individual creates a measureable reflection. The emitted radiation or light can include electromagnetic radiation, ultrasound, or x-ray. Non-limiting examples of active non-contact scanners include hand-held laser scanners as well as a number of three-dimensional scanners (3D scanners) including time-of-flight scanners, triangulation laser scanners, structured-light scanners, and modulated light scanners (see, e.g., Kolb et al., *Computer Graphics Forum* (2010) 29:141-159, which is incorporated herein by reference). In one embodiment, the one or more active scanners can include one or more triangulation scanners in which a laser emitter, a laser dot on the surface being scanned, and a detection camera are used to triangulate the distance between the laser and the laser dot. The topography of the body region, e.g., the face, differentially reflects the distorted light of the laser, which is then captured by a charge-coupled device (CCD) associated with the camera and converted into distance information using triangulation. In one embodiment, the one or more active scanners can include one or more time-of-flight laser scanners in which a laser rangefinder is used to determine the distance between a surface, e.g., the body region of an individual, and the laser emitter by timing the round-trip time of a pulse of light. The time-of-flight laser scanner scans the entire field of view one point at a time by changing the rangefinders view. In one embodiment, the one or more active scanners can include one or more structured-light 3D scanners in which a pattern of light is projected onto the body region of an individual and the deformation of the projected pattern. Scanners for scanning head, face and/or whole body are commercially available (from, e.g., Cyberware, Monterery Calif.; Accurex Measurement Inc., Swathmore, Pa.; 3dMD Atlanta, Ga.; Konica/Minolta, Ramsey, N.J.)

In one embodiment, the one or more digital images are received from at least one passive scanner. A passive scanner relies on detecting reflected ambient radiation, e.g., visible or infrared light. A non-limiting example of a passive scanner includes a digital camera. In one embodiment, the one or more passive scanners include stereoscopic systems using two video cameras, slightly apart, imaging the same portion of the body region of the individual. In one embodiment, the passive scanner can include a single camera taking multiple images under different lighting conditions or from different positions. As an example, one or more digital images of the body region of an individual can be acquired in a point-cloud format using a three-dimensional sensing system consisting of two or more digital cameras and one or more projectors connected to a personal computer. The camera position and shutter can be adjusted to the body region, which is exposed to structured light, allowing for optical representation of the surface by a cloud of up to 300,000 points in three-dimensional coordinates (see, e.g., Feng et al., *Br. J. Oral Maxillofac. Surg.* (2010) 48:105-109, which is incorporated herein by reference).

In one embodiment, the combination of stereophotogrammetry and 3D laser scanner techniques can be combined to generate a three-dimensional model of the body region of an individual (see, e.g., Majid, et al. *International Archives of the Photogrammetry, Remote Sensing and Spatial Information Science*. Vol. XXXVII. Part B5. (2008) 805-811; Markiewicz & Bell, *Facial Plast. Surg. Clin. N. Am.* (2011) 19:655-682; van Heerbeek et al., *Rhinology* (2009) 47:121-125, which are incorporated herein by reference).

Returning to FIG. 22, block 2220 depicts optionally receiving the one or more digital images of the body region from one or more of an ultrasound device, a photoacoustic device, a thermal imaging device, a contact scanning device, a non-contact scanning device, a magnetic resonance image device, a computed tomography device, a capacitance measuring device, electromyographic device, or other biomedical imaging device. For example, skin topographic structures, e.g., wrinkles, can be imaged using a capacitive device with sensor plates pressed lightly on the skin surface (see, e.g., Bevilacqua et al., (2006) *IEEE International Conference on Video and Signal Based Surveillance*, pp. 53, which is incorporated herein by reference). For example, electromyography can be used to determine muscle anatomical features and in particular facial muscle anatomical features (see, e.g., Lapatki et al., *J. Neurophysiol.* (2006) 95:342-354, which is incorporated herein by reference).

Block 2230 of FIG. 22 shows optionally receiving the one or more digital images of the body region through one or more wireless transmissions. In some embodiments, the one or more digital images of the body region are received through one or more wired transmissions. In one embodiment, the one or more digital images are received through one or more of a wired transmission or a wireless transmission from a second computing device. For example, the one or more digital images may be captured with one or more image capture devices at a remote location, downloaded to a second computing device, the one or more digital images received from the second computing device through a wired or wireless transmission. In one embodiment, the one or more digital images are received through one or more wired or wireless transmissions directly from one or more image capture devices. For example, the one or more digital images may be received from one or more image capture devices in real-time as the images are being acquired. Wired transmission can include, but is not limited to, transmission through one or more telephone line, cable line, internet line, fiber optics, coaxial cables, UPT/STP or any other like-wired communication line. Wireless transmission can include, but is not limited to, one or more radio or microwave transmission (e.g., wireless LAN, Wi-Fi, wireless PAN, Bluetooth, wireless WAN, 2G/3G, broadband, MAN, WiMAX, radar and satellite communications), or infrared transmission (e.g., point-to-point or broadcast communication).

FIG. 23 illustrates further aspects of the method of FIG. 21 for generating an injection guide including generating at least one digital representation of the body region. In one embodiment, the at least one digital representation of the body region can be a series of numbers or coordinates representative of the body region. In one embodiment, the at least one digital representation of the body region may be visible on a display, e.g., a computer monitor, as a literal image of the body region, e.g., a digital photograph displayed on a computer monitor or other digital display. Further aspects of generating at least one digital representation of the body region are illustrated in blocks 2300 and 2310. Block 2300 shows optionally generating the at least one digital representation of the body region by overlaying the one or more digital images of the body region. For example, one or more digital images may be received from two or more cameras positioned in a semi-circle in front of the body region being imaged. Block 2310 shows optionally generating a three-dimensional digital model of the body region using the one or more digital images and at least one three-dimensional modeling algorithm. Generating a three-dimensional digital model of the body region using the received one or more digital images includes using a computing device and appropriate software or instructions. In one embodiment, the one or more digital images are received into a computing device that is capable of aligning or registering the images into a common coordinate system and then integrating the images into a single three-dimensional digital model.

In one embodiment, active or passive scanners may produce point clouds of data that are reconstructed using one or more three-dimensional modeling algorithms to form a three-dimensional digital model of the body region. For example, surface scanning software can be used to import individual points of the body region, e.g., of the face, and then combine them in the X, Y, and Z axes to render a three-dimensional representation of the body region. One or more modeling programs can be used for this purpose. Non-limiting examples of types of modeling programs include polygonal mesh three-dimensional modeling programs, non-uniform rational basis spline (NURBS) surface modeling programs, or editable feature-based computer aided design (CAD) modeling programs. In one embodiment, the data may be modeled using a first modeling approach, for example, a NURBS based modeling program and further refined using a second modeling approach, for example, a CAD-based modeling program. Numerous software programs are available for generating three-dimensional models from scanned images. For example, non-limiting examples of CAD/CAM software programs applicable to medical imaging include Amira (Visage Imaging GmbH, Berlin Germany); Analyze (AnalyzeDirect, Inc, Overland Park, Kans.); iNtellect Cranial Navigation System (Stryker, Freiburg, Germany); iPlan (BrainLab, Westchester, Ill.); Maxilim (Medicim, Bruges Belgium), Mimics, SurgiCase CMF, and SimPlant OMS (Materialise, Leuven, Belgium); Voxim (IVS Solutions, Chemnitz, Germany), 3dMD (Atlanta, Ga.); Alma3D (Alma IT Systems, Barcelona, Spain); and ImageJ (National Institutes of Health, Boston, Mass.) (see, e.g., Markiewicz & Bell, *Facial Plast. Surg. Clin. N. Am.* (2011) 19:655-682, which is incorporated herein by reference). Facial feature extraction can be acquired using one or more of an active shape model algorithm (see, e.g., Sun & Xie, 11*th IEEE International Conference on Communication Technology Proceedings*, (2008) pp. 661-664; Zheng & Yang *IEEE Proceedings of the Seventh International conference on Machine Learning and Cybernetics*, (2008) pp. 2841-2845, which are incorporated herein by reference). Other software packages capable of generating a three-dimensional digital model from one or more digital images of a body region of an individual can be used for this purpose. Additional approaches for generating three-dimensional digital models are described in Bernardini & Rushmeier *Computer Graphics Forum* (2002) 21:149-172, which is incorporated herein by reference.

FIG. 23 illustrates an embodiment of the method FIG. 21 for generating an injection guide that optionally includes block 2320. Block 2320 shows optionally generating an injection-treatment plan based on analysis of the at least one digital representation of the body region. The injection-treatment plan, as illustrated in block 2360, can include at least one of one or more injection sites, a pattern of injection sites, a type of injectable agent, a type of injector, a dosage of an injectable agent, an injection sequence, an injection timing, an injection depth, and/or an injection angle. In one embodiment, as illustrated in block 2330, generating an injection-treatment plan based on analysis of the at least one digital representation of the body region can include identifying an area of the body region in need of treatment by comparison of the at least one digital representation of the body region with at least one stored representation of at least one comparable body region. In one embodiment, as shown in block 2340 of FIG. 23, the injection-treatment plan comprises one or more injections of at least one injectable agent arranged in an injection-treatment pattern specific for the individual. In some embodiment, as shown in block 2350 of FIG. 23, the injection-treatment plan comprises one or more injections of at least one injectable agent arranged in an injection-treatment pattern specific for a condition being treated.

In one embodiment, generating an injection-treatment plan can include generating an injection-treatment plan based on one or more digital images of the body region of an individual in at least one first expression state and at least one second expression state. For example, one or more images of a body region of an individual's face can be acquired while the individual is in a first expression state, e.g., in a relaxed state, and used to reveal lines or wrinkles present on the individual's face in the first expression state. One or more images of the individual's face are acquired in a second expression state, e.g., a tensed or animated state. Non-limiting examples of tensed or animated states include laughing, smiling, frowning, grimacing or other non-relaxed states of the individual's face. The one or more images of the individual's face in the second expression state, e.g., the animated state, can be used to reveal additional lines or wrinkles present on the individual's face in the second expression state relative to the first expression state, e.g., the relaxed state. For example, the one or more images of the individual's face can be acquired while the individual is frowning and generating associated frown-line/wrinkles (glabellar lines) between the eyebrows. As another example, the one or more images of the body region of the individual's face can be acquired while the individual is smiling and generating laugh lines (nasolabial folds) and/or crow's feet near the eyes. In one embodiment, comparing the one or more digital images of the body region of the individual in the at least one first expression state and the at least one second expression state to generate an injection-treatment plan includes overlaying the one or more digital images in the first expression state and the one or more digital images in the second expression state to identify one or more areas of the body region in need of treatment. For example, the one or more images of the individual's face in a first expression state, e.g., a relaxed state, are overlaid with the one or more images of the individual's face in a second expression state, e.g., an animated state. In this manner, areas in need of treatment, e.g., frown lines between the eye brows or smile lines around the mouth, can be identified and placed into the at least one digital representation of the body region and viewed by the physician or other practitioner. The injection-treatment plan including at least one treatment parameter can then be formulated based on the treatment need. Accordingly, one or more digitally registered injection sites indicative of one or more injections sites and/or at least one treatment parameter can be added either automatically by the computing device or by a physician, other practitioner, or the individual to the at least one digital representation of the body region.

FIG. 24 illustrates further aspects of the method of FIG. 21 for generating an injection guide. Block 2120 shows adding one or more digitally registered injection sites to the at least one digital representation of the body region in an injection-treatment pattern, the one or more digitally registered injection sites registered relative to the one or more digital registration landmarks and optionally includes blocks 2400, 2410, 2420, and 2430. Block 2400 shows optionally adding the one or more digitally registered injection sites automatically based on a computed injection-treatment plan. For example, the one or more digitally registered injection sites can be automatically added in an injection-treatment pattern based on computational analysis of the at least one digital representation of the body region of the individual. The computational analysis includes determining where treatment is needed on the body region and the appropriate pattern of injection sites to administer that treatment. In one embodiment, the pattern of injection sites is generic for a particular condition or treatment option. In one embodiment, the pattern of injection sites is specific to an individual, patterned to accommodate specific needs and/or anatomical features of the individual. In one embodiment, the pattern of injection sites is part of an injection-treatment plan, the injection-treatment plan is either a generic injection-treatment plan, an injection-treatment plan specific for an individual, or combinations thereof.

A computed injection-treatment plan can include a comparison of the at least one digital representation of the body region with stored data that includes one or more images of standard, normal or ideal body regions or previously captured images of the body region of the individual. In one embodiment, the stored data includes idealized aesthetics of a female or male face (see, e.g., Carruthers et al., *Plast. Reconstr. Surg.* (2008) 121 (Suppl):5S-30S, which is incorporated herein by reference). In one embodiment, the stored data include normalized skin characteristics based on age or other demographics (see, e.g., Wolff et al., *Fertil. Steril.* (2011) 95:658-662, which is incorporated herein by reference). In one embodiment, the one or more digitally registered injection sites can be added automatically to the at least one digital representation of the body region by a computing device based on data from the database of stored treatment parameters. In one embodiment, the computed injection-treatment plan can include algorithms for predicting the outcome of a particular treatment regimen. For example, the computed injection-treatment plan may be used to show an individual via a display, e.g., a computer monitor, how a given facial feature, e.g., nasolabial folds, will change in response to injection of an injectable agent, e.g., a dermal filler.

Block 2410 of FIG. 24 shows optionally adding the one or more digitally registered injection sites with a user input device. The user input device can include a keyboard or interactive display panel, e.g., a touchpad or stylus. In one embodiment, the user input device is a keyboard in communication with the computing device that is implementing the method for generating an injection guide. In one embodiment, the user input device is a wireless device, e.g., a cell phone or other handheld device, capable of wirelessly adding one or more digitally registered injection sites to the at least one digital representation of the body region. In one embodiment, the one or more digitally registered injection sites can be added by a physician or other practitioner using an input device based on consulting data from a database of stored treatment parameters. In one embodiment, the one or more digitally registered injection sites can be added to the at least one digital representation of the body region based on preferences of the individual. For example, the individual can sit with a physician or other practitioner in front of a display, e.g., a computer monitor, and interactively add or subtract one or more digitally registered injection sites. In one embodiment, the individual is also able to see the consequences, e.g., predicted changes in facial features or other body structures, of adding a digitally registered injection site to a given location of the digital representation of the body region.

Block 2420 of FIG. 24 shows optionally adding one or more of a dot, a crosshair, a circle, or concentric circles representative of the one or more digitally registered injection sites to the at least one digital representation of the body region. The one or more dot, crosshair, circle, or concentric circles representative of the one or more digitally registered injection site will be illuminated onto the surface of the body region of the individual to indicate one or more injection sites on the body region. It is intended that actual injection into the underlying skin of the body region will occur at or near one or more dot, crosshair, circle, or concentric circles illuminated on the surface of the body region. For example, injection may occur at the cross-section of lines comprising the crosshairs, in the middle of the concentric circles, or in the center of the circle or dot.

Block 2430 of FIG. 24 shows optionally adding one or more of a letter, number, shape, symbol, color, or combination thereof representative of the one or more digitally registered injection sites to the at least one digital representation of the body region. The one or more of a letter, number, shape, symbol, color, or combinations thereof representative of the one or more digitally registered injection sites will be illuminated onto the surface of the body region of the individual to indicate one or more injection sites on the body region. In one embodiment, the one or more of the letter, number, shape, symbol, color, or combinations thereof further represent at least one treatment parameter, as illustrated in block 2440. In one embodiment, the one or more letter, number, shape, symbol, color, or combinations thereof indicates both the site of injection as well as a treatment parameter associated with that site of injection. For example, a blue X may be added to the digital representation, the blue color indicative of a dose of a particular neurotoxin, e.g., 5 Units of *botulinum* toxin, and the X indicating where the injection should be made. In one embodiment, two or more letters, numbers, shapes, symbols, colors, or combinations thereof are illuminated on the surface of the body region. For example, a first letter, number, shape, symbol, or color may indicate an injection site while a second letter, number, shape, or color may indicate one or more treatment parameters. Block 2450 shows optionally wherein the one or more of a letter, number, shape, symbol, color, or combinations thereof are representative of at least one of an injection site, a type of injectable agent, a type of injector, a dosage of an injectable agent, a sequence of injecting an injectable agent, a timing of injection an injectable agent, an injection depth, or an injection angle.

In one embodiment, the one or more of a letter, number, shape, symbol, color, or combination thereof are representative of at least one type of injectable agent to be injected at one or more illuminated injection site. The type of injectable agent can include one or more of a neurotoxin, subcutaneous dermal enhancer, dermal filler, insulin, antibiotic, hormone, chemotherapeutic agent, anti-inflammatory agent, or biological agent, non-limiting examples of which have been described above herein. Illuminating the surface of the body region with one or more of a letter, number, shape, symbol, color, or combination thereof indicative of other injectable agents not explicitly described herein is also contemplated. In one embodiment, the one or more letter, number, shape, symbol, color, or combination thereof representative of the one or more digitally registered injection sites are representative of the dosage of a particular injectable agent, e.g., the units of *botulinum* toxin or milliliters of collagen filler, to be injected at a given illuminated injection site.

In one embodiment, the one or more of a letter, number, shape, symbol, color, or combination thereof are representative of at least one type of injector to be used at one or more illuminated injection site. In one embodiment, the injector includes a needle attached to a syringe, e.g., a hypodermic needle, for penetrating the surface of the body region. Other needle systems are contemplated, including one or more microneedles. In one embodiment, the injector is needleless, non-limiting examples of which include jet injectors, electroporation, iontophoresis, ultrasound, microshock wave, powder injection, and tape stripping (see, e.g., Jagadeesh et al., *Clin. Vaccine Immunol.* (2011) 18:539-545, which is incorporated herein by reference). In one embodiment, the at least one type of injector is a syringe with a standard length injection needle. For example, standard injection needles range in length from 3/16 inches (5 mm) to 1½ inches (38 mm) from the tip of the needle bevel to the needle hub. The choice of injection needle will also be dependent upon how deep the injection is intended to go. For example, needles ranging in length from ½ inch to ⅝ inch can be used for subcutaneous injections, while needles ranging in length from 1 inch to 1½ inch can be used for intramuscular injections. Injection needles are further defined by the outer diameter, i.e., gauge, of the needle shaft. The gauge of an injection needle is inversely proportional to its outer diameter. Injections needle range in gauge from 7 gauge (outer diameter approximately 4.6 mm) to 34 gauge (outer diameter approximately 0.19 mm). Injection needles commonly used for injecting agents into mammalian tissue range in size from 21 to 32 gauge.

In one embodiment, the one or more of a letter, number, shape, symbol, color, or combination thereof are representative of at least one depth of injection at the one or more illuminated injection sites. The depth to which a needle, for example, is inserted at any given illuminated injection site and into the underlying tissue of the body region is dependent upon both the specific features of the body region and on the injectable agent being injected at said illuminated injection site. For example, specific features of an individual's face could dictate injection depth, including the severity of lines or wrinkles and/or the thickness of the tissue layers at any given injection site. For example, the thickness of the epidermis (top layer of skin) is about 0.05 mm near the eye lids while the epidermis on the rest of the face is on average of about 0.1 to 0.3 mm. In addition, the injection depth may be dependent upon the age of the individual, as the tissue layers thin with increasing age. Furthermore the depth may be dependent upon the injectable agent being injected and the type of tissue into which said injectable agent is injected. For example, the dermal filler hyaluronic acid can be injected into the superficial papillary dermis for treating fine wrinkles and scars, but is injected deeper into the reticular dermis for deeper lines. Similarly, collagen filler can be injected into the papillary and middle dermis to treat fine lines and wrinkles in the upper lip, the periorbital area, and glabella of the face. Polymethylmethacrylate microspheres filler can be injected subdermally, e.g., into the border of the dermis and subcutaneous fat, to treat rhytids and scars. *Botulinum* toxin can be injected to about 2 to 3 mm below the surface of the skin.

In one embodiment, the one or more of a letter, number, shape, symbol, color, or combination thereof are representative of at least one angle of injection at the one or more illuminated injection sites. The angle at which a needle of an injector is inserted into the underlying tissue of the body region is dependent upon the nature of the injectable agent and the depth to which the injectable agent is being injected. In one embodiment, the at least one injectable agent is injected with an injector at the one or more illuminated injection sites at a 90 degree angle relative to the surface of the body region. In one embodiment, the at least one injectable agent is injected with an injector at the one or more illuminated injection sites at less than a 90 degree angle relative to the surface of the body region. For example, injections into the muscle with, e.g., penicillin may be done with an injector at a 90 degree angle; injections into the subcutaneous tissue with, e.g., morphine, may be done with an injector at a 45 degree angle; and injections into the epidermis or dermis with, e.g., a vaccine may be done with an injector at a 10 to 15 degree angle.

FIG. 25 illustrates further aspects of the method of FIG. 21 for generating an injection guide including generating one or more output signals having information for controlling one or more controllable light-emitting elements to illuminate a location on a surface of the body region of the individual corresponding in location to at least one of the one or more digitally registered injection sites. The one or more output signals having information for controlling one or more of the controllable light-emitting elements can include one or more output signals having information for controlling one or more of an on/off function, position, intensity, focus, color of emitted light, or pattern of emitted light. The one or more output signals having information for controlling one or more controllable light-emitting elements can include one or more output signals having information for dynamically controlling one or more of an on/off function, position, intensity, focus, color of emitted light, or pattern of emitted light. Dynamically controlling the one or more controllable light-emitting elements can include controlling a spatial or temporal sequence of illumination on the surface of the body region. For example, the method can include generating one or more output signals having information for controlling an on/off sequence or color of emitted light during the course of an injection treatment such that the different injection sites are illuminated in a sequence or different colors are illuminated at different times on the surface of the body region as part of an injection-treatment plan.

Block 2130 of FIG. 25 optionally includes blocks 2500, 2510, and 2520. Block 2500 shows optionally generating one or more output signals having information for controlling one or more of a controllable projector, light-emitting diode, laser, laser diode, collimated light source, or focused light source. Non-limiting examples of controllable light-emitting elements have been described above herein. Block 2510 shows optionally generating one or more output signals having information for controlling one or more controllable light-emitting elements to illuminate a location on the surface of the body region of the individual with one or more spots, crosshairs, circles, or concentric circles corresponding in location to at least one of the one or more digitally registered injection sites. Block 2520 shows optionally generating one or more output signals having information for controlling one or more controllable light-emitting elements to illuminate a location on the surface of the body region of the individual with one or more of a letter, number, shape, symbol, color, or combination thereof corresponding in location to at least one of the one or more digitally registered injection sites.

FIG. 26 illustrates further aspects of the method of FIG. 21 for generating an injection guide. Block 2130 optionally includes blocks 2600, 2610, and 2620. Block 2600 shows optionally generating one or more output signals having information for controlling the one or more controllable light-emitting elements to illuminate the location on the surface of the body region of the individual corresponding in location to the at least one of the one or more digitally registered injection sites in accordance with an injection-treatment plan. Block 2610 shows optionally generating one or more output signals having information for controlling the one or more controllable light-emitting elements to sequentially illuminate one or more locations on the surface of the body region of the individual corresponding in location to one or more digitally registered injection sites in accordance with an injection-treatment plan. Block 2610 further includes block 2620. Block 2620 shows optionally generating one or more output signals having information for controlling the one or more controllable light-emitting elements to sequentially illuminate the one or more locations on the surface of the body region of the individual based on accurate completion of an injection at a previously illuminated injection site.

FIG. 27 illustrates further aspects of the method of FIG. 21 for generating an injection guide. Block 2700 shows optionally generating one or more output signals having information for projecting one or more annotations on the surface of the body region of the individual at or near one or more illuminated injection sites. The one or more annotations can include letters, text, numbers, shapes, symbols, colors, or combinations thereof representative of one or more pieces of information relating to one or more treatment parameters and/or an injection status update. In one embodiment, the one or more annotations are projected in proximity to the one or more illuminated injection sites and provide specific instructions for a given injection site. In one embodiment, the one or more annotations are projected on the body region without regard for the illuminated injection sites and may provide general instructions for injecting at one or more illuminated injection sites. For example, annotations may be projected on the body region to instruct the user to inject all illuminated injection sites with a given injectable agent, e.g., a dermal filler, at a given dose, e.g., one milliliter per sub-dermal injection.

FIG. 27 further includes block 2710. Block 2710 shows optionally generating one or more output signals having information for adjusting the one or more controllable light-emitting elements so as to align one or more illuminated injection sites relative to the one or more physical registration landmarks on the body region of the individual to substantially correspond to the at least one digital representation of the body region.

FIG. 28 illustrates further aspects of the method of FIG. 21 for generating an injection guide. FIG. 28 includes block 2800. Block 2800 shows optionally receiving in real-time one or more second digital images of the body region of the individual including the one or more physical registration landmarks and the one or more illuminated injection sites on the surface of the body region; and generating one or more output signals having information for adjusting the one or more controllable light-emitting elements so as to align the one or more illuminated injection sites relative to the one or more physical registration landmarks on the body region to substantially correspond to the at least one digital representation of the body region.

Figure 29:
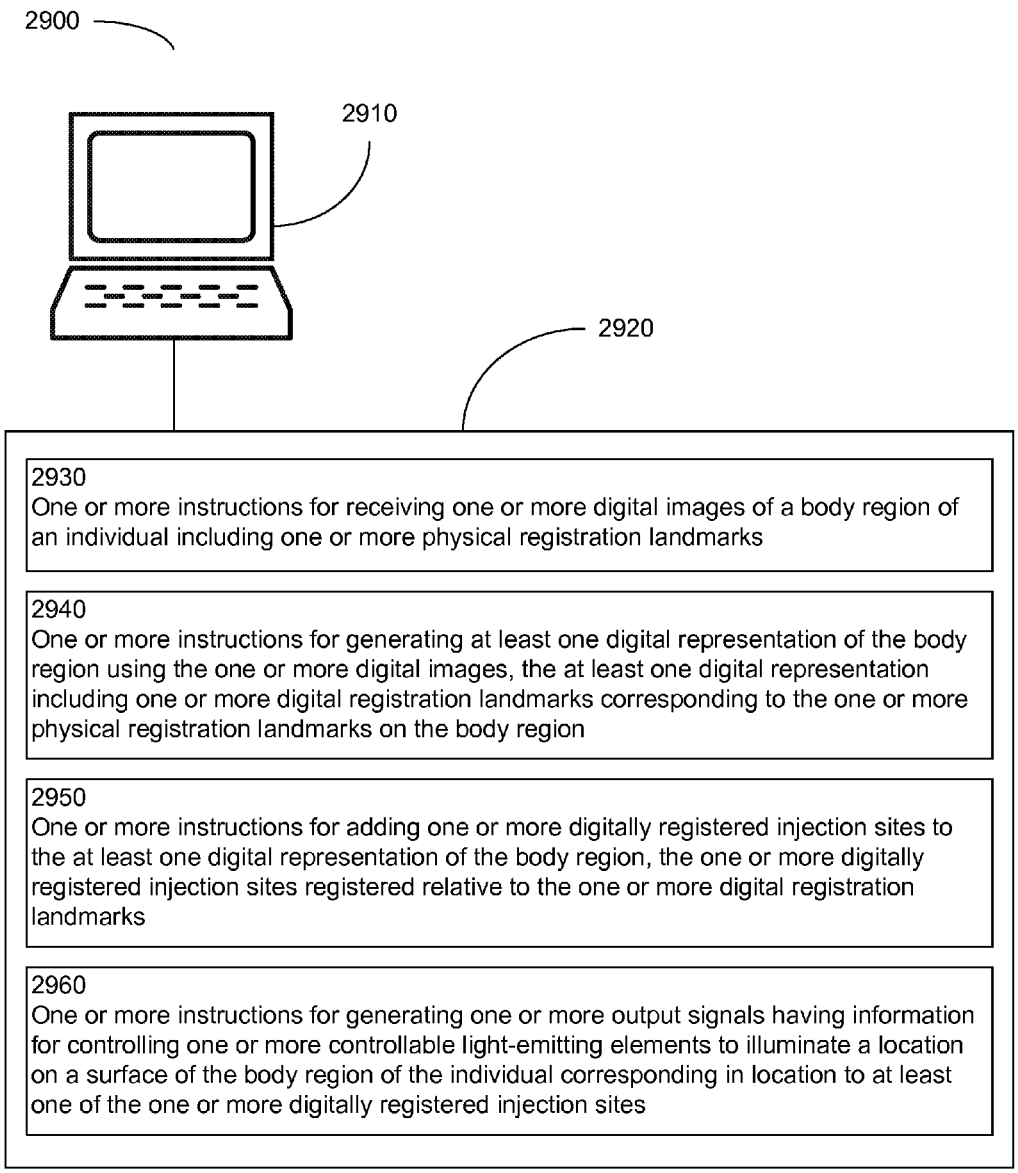
FIG. 29 is a schematic of an embodiment of a system for generating an injection guide.

A system is described herein comprising a computer processor and non-transitory signal-bearing medium bearing one or more instructions for generating an injection guide. FIG. 29 illustrates an embodiment of such a system. System 2900 includes computer processor 2910 and non-transitory signal-bearing medium 2920. Non-limiting examples and embodiments of a computer processor including a computing device have been described herein, e.g., in FIG. 2.

Non-transitory signal-bearing medium 2920 stores instructions and/or data for use in generating the injection guide. In an embodiment, non-transitory signal-bearing medium 2920 can be computer readable media. In an embodiment, non-transitory signal-bearing medium 2920 can be recordable-type media. Computer readable media may also be recordable-type media, and the qualities of being "computer readable" and "recordable-type" should not be construed as being mutually exclusive, though in some cases a computer readable media may not be a recordable-type media, and vice versa. Machine readable media include volatile and nonvolatile, removable and non-removable media implemented in any method or technology for storage of information such as machine readable instructions, data structures, program modules, or other data. Non-transitory signal-bearing media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other media which can be used to store the desired information and which can be accessed by computer processor 2910. In a further embodiment, computer storage media may include a group of computer storage media devices. In an embodiment, machine readable media may include an information store. In an embodiment, an information store may include a quantum memory, a photonic quantum memory, or atomic quantum memory. Combinations of any of the above may also be included within the scope of non-transitory machine readable media.

Non-transitory signal-bearing medium 2920 bearing one or more instructions for generating an injection guide further includes one or more instructions 2930 for receiving one or more digital images of a body region of an individual including one or more physical registration landmarks; one or more instructions 2940 for generating at least one digital representation of the body region using the one or more digital images, the at least one digital representation including one or more digital registration landmarks corresponding to the one or more physical registration landmarks on the body region, one or more instructions 2950 for adding one or more digitally registered injection sites to the at least one digital representation of the body region, the one or more digitally registered injection sites registered relative to the one or more digital registration landmarks; and one or more instructions 2960 for generating one or more output signals having information for controlling one or more controllable light-emitting elements to illuminate a location on a surface of the body region of the individual corresponding in location to at least one of the one or more digitally registered injection sites.

The non-transitory signal-bearing medium including one or more instructions for receiving one or more digital images of a body region further includes one or more instructions for receiving one or more digital images of a face, head, neck, torso, abdominal, upper extremity, lower extremity, buttocks region, or any other region accessible to injection of an injectable agent. The one or more body regions include one or more physical registration landmarks, the physical registration landmarks including one or more markers placed on a surface of the body region and/or one or more of a pigmentation, pigmented area, anatomical feature, subsurface blood vessel, blemish, scar, or tattoo, non-limiting examples of which have been described herein.

FIG. 30 illustrates further aspects of the system of FIG. 29. In an embodiment, non-transitory signal-bearing medium 2920 including one or more instructions 2930 for receiving one or more digital images of a body region can optionally include one or more instructions 3000 for receiving the one or more digital images from a second computing device 3010 through one or more wired 3020 or wireless 3030 transmission.

FIG. 31 illustrates further aspects of the system of FIG. 29. In an embodiment, non-transitory signal-bearing medium 2920 including one or more instructions 2930 for receiving one or more digital images of a body region can optionally include one or more instructions 3100 for receiving the one or more digital images from at least one image capture device 3110 through one or more wired 3120 or wireless 3130 transmissions. In addition, image capture device 3110 is able to receive one or more wired 3120 or wireless 3140 transmissions from computer processor 2910. Image capture device 3110 includes at least one of a camera, active scanner, passive scanner, ultrasound device, photoacoustic device, thermal imaging device, contact scanning device, magnetic resonance imaging device, computed tomography device, capacitance measuring device, or other biomedical imaging device, non-limiting examples of which have been described herein. Non-transitory signal-bearing medium 2920 optionally includes one or more instructions 3150 for controlling one or more functions of the at least one image capture device. One or more instructions 3150 optionally include one or more instructions 3160 for controlling acquisition of the one or more digital images of the body region of the individual with the at least one image capture device 3110 and/or one or more instructions 3170 for controlling one or more of an on/off function, positioning function, scanning rate function, exposure function, or energy emission function of the at least one image capture device 3110. One or more instructions 3150 can further include one or more instructions for controlling the quality and/or quantity of radiation, e.g., light, projected on the individual and/or one or more instructions for causing movement of the at least one capture image capture device to allow image capture from different positions or angles relative to the individual.

In one embodiment, the non-transitory signal-bearing medium including one or more instructions 2940 for generating the at least one digital representation of the body region using the one or more digital images includes one or more instructions for overlaying the one or more digital images of the body region of the individual to generate the at least on digital representation of the body region. In one embodiment, the non-transitory signal-bearing medium includes one or more instructions for generating a three-dimensional representation of the body region from the one or more digital images. In one embodiment, the one or more instructions for generating the at least one digital representation of the body region include one or more instructions associated with an algorithm configured to generate a three-dimensional representation of the body region using the one or more received digital images. Examples of algorithms and software programs for three-dimensional modeling have been described above herein.

Figure 32:
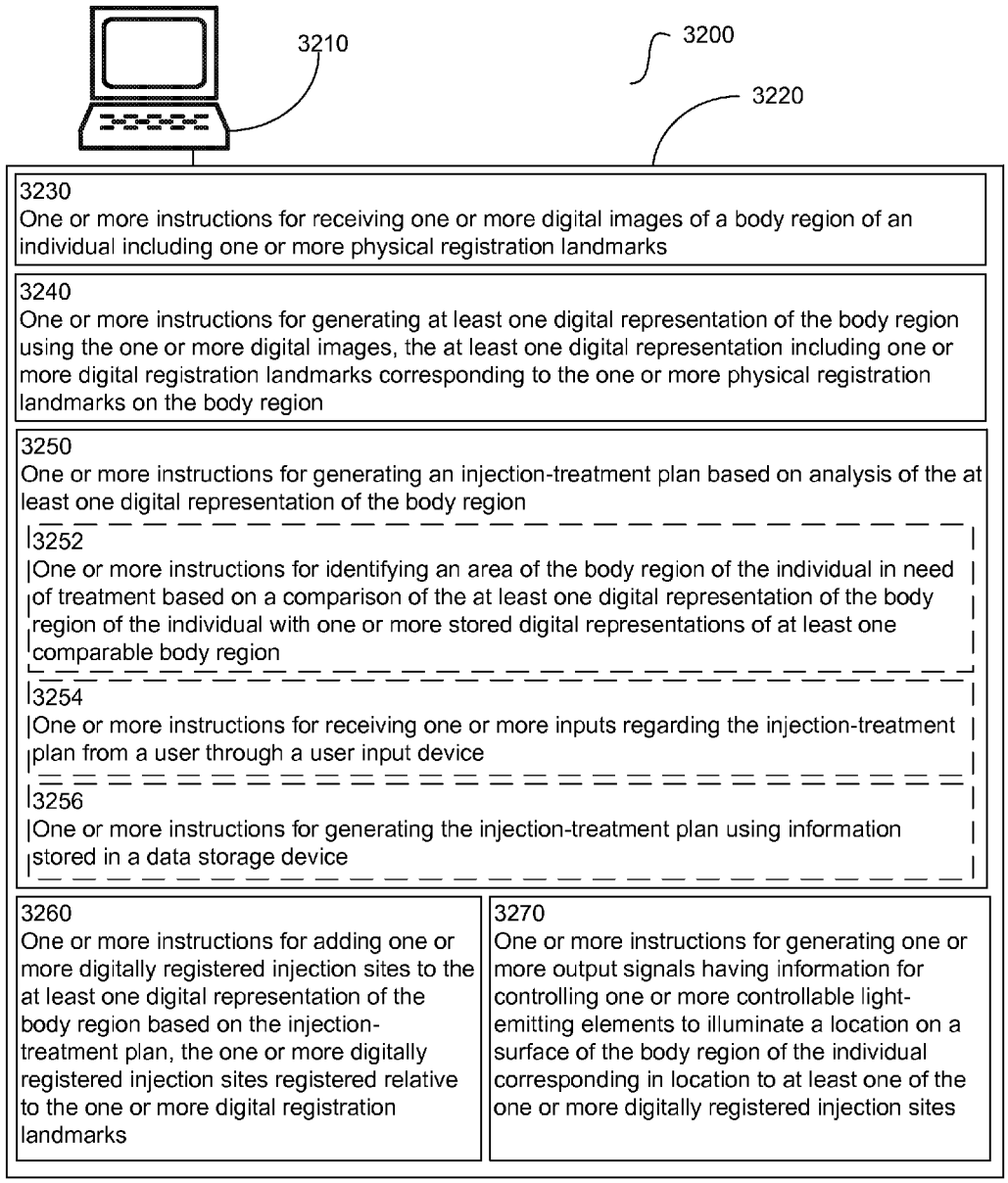
FIG. 32 is a schematic of an embodiment of a system for generating an injection guide.

FIG. 32 illustrates an embodiment of a system for generating an injection guide. System 3200 includes a computer processor 3210 and non-transitory signal-bearing medium 3220 bearing one or more instructions for generating an injection guide including one or more instructions 3230 for receiving one or more digital images of a body region of an individual including one or more physical registration landmarks; one or more instructions 3240 for generating at least one digital representation of the body region using the one or more digital images, the at least one digital representation including one or more digital registration landmarks corresponding to the one or more physical registration landmarks on the body region; one or more instructions 3250 for generating an injection-treatment plan based on analysis of the at least one digital representation of the body region; one or more instructions 3260 for adding one or more digitally registered injection sites to the at least one digital representation of the body region based on the injection-treatment plan, the one or more digitally registered injection sites registered relative to the one or more digital registration landmarks; and one or more instructions 3270 for generating one or more output signals having information for controlling one or more controllable light-emitting elements to illuminate a location on a surface of the body region of the individual corresponding in location to at least one of the one or more digitally registered injection sites.

The non-transitory signal-bearing medium including one or more instructions 3250 for generating an injection-treatment plan based on analysis of the at least one digital representation of the body region includes one or more instructions 3252 for identifying an area of the body region of the individual in need of treatment based on comparison of the at least one digital representation of the body region of the individual with one or more stored digital representations of a comparable body region. In one embodiment, the one or more stored digital representations of a comparable body region include one or more historical digital representations of the comparable body region of the individual. For example, the one or more historical digital representations of the body region can include one or more digital representations of the body region of the individual generated earlier in time, when the individual was younger or prior to and/or after previous injection treatment. For example, the historical digital representation of a body region, e.g., the face of the individual, might include an enhancement with a dermal filler, fuller cheeks or lips, and can be compared with the a current digital representation to calculate an injection-treatment plan. In one embodiment, the one or more stored digital representations of a comparable body region include one or more idealized digital representations of the comparable body region. The comparison of the at least one digital representation and the one or more stored digital representations of a comparable body region by, for example, an overlay and/or subtractive process is used to identify areas in need of treatment. Once an area has been identified as an area in need of treatment, the computer processor may automatically add one or more digitally registered injection sites to the digital representation location corresponding to injection site locations. In one embodiment, the one or more instructions for adding the one or more digitally registered injection sites are based on an outcome defined by the individual. For example, the individual may request enhanced lips or reduced frown lines based on analysis of, e.g., viewing the at least one digital representation on a display, e.g., a computer monitor.

The non-transitory signal-bearing medium further includes one or more instructions 3254 for receiving one or more inputs regarding the injection-treatment plan from a user through a user input device. For example, a physician or other practitioner may enter the injection-treatment plan including the number and type of injections using a user input device, e.g., a keyboard or touchpad. In one embodiment, the individual may choose an idealized digital representation of a comparable body region, e.g., idealized eyebrows or cheeks bones, and the physician or other practitioner instructs the computer processor to compare the idealized digital representation with the at least one digital representation of a comparable body region of the individual to generate an injection-treatment plan. In one embodiment, the injection-treatment plan is specific to the individual. For example, treatment with a collagen filler to augment certain portions of an individual's face might be specific to the desired outcome, age, and quality of the individual's skin. In one embodiment, the injection-treatment plan is specific to the condition being treated. For example, a course of antibiotics administered to an upper thigh or abdominal region might be specific for a type of bacterial infection and as such the treatment parameters, e.g., the type of injectable agent, the injection sites, and the dosage, etc., may be generic for that type of bacterial infection.

The non-transitory signal-bearing medium further includes one or more instructions 3256 for generating the injection-treatment plan using information stored in a data storage device. The information stored in a data storage device can include any of a number of parameters pertinent to an injection-treatment plan including, but not limited to, one or more of a diagnosis, a condition, a type of injectable agent, a dose of an injectable agent, an injection treatment pattern, a type of injector, a sequence of injection, a timing of injection, an injection depth, or an injection angle. For example, the information stored in the data storage device can include treatment options, e.g., injectable agents, for a given condition as well as dosing information and information regarding needle penetration and needle size specific for any given injectable agent. The information stored in a data storage device can further include the individual's medical record, a record of past injection-treatments, a record of past injection-treatment plans, adverse reactions to previous injection-treatments, skin properties, individual treatment preferences, comorbidities, age, weight, gender, and allergies, any or all of which can be taken into consideration while generating the injection-treatment plan.

FIG. 33 illustrates further aspects of the system of FIG. 29. Non-transitory signal-bearing medium 2910 includes one or more instructions 2950 for adding one or more digitally registered injection sites to the at least one digital representation of the body region. In one embodiment, the non-transitory signal-bearing medium optionally includes one or more instructions 3300 for adding the one or more digitally registered injection sites to the at least one digital representation of the body region in an injection-treatment-pattern as part of an injection-treatment plan. In one embodiment, the non-transitory signal-bearing medium includes one or more instructions 3310 for automatically adding the one or more digitally registered injection sites to the at least one digital representation of the body region. For example, the computer processor and associated non-transitory signal-bearing medium may be operable to design an injection-treatment plan that includes one or more injection sites in an injection-treatment pattern and automatically add digitally registered injection sites representative of the proposed injection sites to a digital representation of the body region based on the injection-treatment plan. In one embodiment, the non-transitory signal-bearing medium includes one or more instructions 3320 for adding the one or more digitally registered injection sites to the at least one digital representation of the body region using a user input device. For example, a physician or other practitioner may use a keyboard, touchpad, or stylus associated with the computing device and either directly add the digitally registered injection sites or enter information that would allow the computer processor to automatically add the digitally registered injection sites. For example, the user may enter coordinates to indicate where a digitally registered injection site should be placed relative to one or more digital registration landmarks corresponding to one or more physical registration landmarks on the body region.

Referring again to FIG. 33, in one embodiment, the non-transitory signal-bearing medium optionally includes one or more instructions 3330 for adding one or more colors, letters, numbers, shapes, symbols, or combinations thereof representative of the one or more digitally registered injection sites to the at least one digital representation of the body region. In one embodiment, the one or more shapes representative of one or more digitally registered injection sites include one or more dots, crosses, rings, concentric circles, or crosshairs representative of the one or more digitally registered injection sites. For example, the one or more digitally registered injection sites may be represented by dots of varying size, the exact size of the dot dependent upon the accuracy required in performing an injection at the injection site represented by the digitally registered injection site.

In one embodiment, the one or more colors, letters, numbers, shapes, symbols, crosshairs, or combinations thereof representative of the digitally registered injection sites comprise information pertaining to at least one treatment parameter. The non-transitory signal-bearing medium can include one or more instructions for adding colors, letters, numbers, shapes, symbols, crosshairs, or combinations thereof that comprise information pertaining to any or all aspects of an injection-treatment plan including, but not limited to, at least one of an injection site, a type of injectable agent, a dosage of an injectable agent, a type of injector, a dosing schedule, an injection depth, or an injection angle, non-limiting examples of which have been described elsewhere herein. The type of injectable agent can include, but is not limited to, a neurotoxin, subcutaneous dermal enhancer, dermal filler, insulin, antibiotic, hormone, chemotherapeutic agent, anti-inflammatory agent, cells, or biological agent. The injection depth can be about 0.5 mm to about 25 mm below the surface of the skin. In some embodiments, the injection depth is dependent upon the type of injectable agent, the injection site, and/or the condition being treated. The injection angle can be about greater than 0 degrees to about less than or equal to 90 degrees. In some embodiments, the injection angle is dependent upon one or more of the type of injectable agent, the injection site, or the condition being treated. In one embodiment, the dosing schedule includes a temporal sequence of injection an injectable agent at two or more injection sites. In one embodiment, the dosing schedule includes a temporal sequence of injecting two or more injectable agents at one or more injection sites.

In one embodiment, the system further includes non-transitory signal-bearing medium bearing one or more instructions for generating an injection guide including one or more instructions for adding one or more annotations to the at least one digital representation of the body region. The one or more annotations include one or more pieces of information pertaining to the injection treatment. In one embodiment, the annotations are only meant to be seen on a display, e.g., a monitor associated with the computer processor. In one embodiment, the one or more annotations are projected onto a surface of the body region of the individual at or near one or more illuminated injection sites. The one or more annotations can be represented by one or more letters, numbers, shapes, symbols, text, colors, or combinations thereof. In one embodiment, the one or more annotations are representative of one or more treatment parameters. In one embodiment, the one or more annotations are representative of one or more injection status updates.

FIG. 34 illustrates further aspects of the system of FIG. 29. Non-transitory signal-bearing medium 2920 bearing one or more instructions 2960 for generating one or more output signals having information for controlling one or more controllable light-emitting elements to illuminate a location on a surface of the body region of the individual corresponding in location to at least the one or more digitally registered injection sites can optionally include one or more instructions 3400 for generating one or more output signals having information for controlling one or more of an on/off function, focus, intensity, position, color of light emitted, pattern of light emitted, sequencing, or timing of the one or more controllable light-emitting elements. The one or more output signals are generated based on the digital representation of the body region, the one or more digitally registered injection sites, and the injection-treatment plan, any or all of which dictate when, where, and how light from the one or more controllable light-emitting elements should be illuminated on the surface of the body region. One or more instructions 2960 for generating one or more output signals having information for controlling one or more controllable light-emitting elements can optionally include one or more instructions 3410 for generating one or more output signals having information for controlling one or more controllable light-emitting elements to illuminate one or more locations on the surface of the body region of the individual in a temporal sequence in accordance with an injection-treatment plan, the one or more locations corresponding to the one or more digitally registered injection sites. For example, the one or more output signal can have information for sequentially turning on and off specific controllable light-emitting elements in an array of controllable light-emitting elements. For example, the one or more output signal can have information for moving one or more controllable light-emitting element over time so as to sequentially illuminate different locations on the surface of the body region.

In one embodiment, non-transitory signal-bearing medium 2920 bearing one or more instructions for generating an injection guide can further include one or more instructions 3420 for generating one or more output signals having information for controlling one or more controllable light-emitting elements to project one or more annotations onto the surface of the body region of the individual. One or more instructions 3420 can further include one or more instructions for generating one or more output signals having information for controlling the one or more controllable light-emitting elements to project the one or more annotations at or near one or more illuminated injection sites on the surface of the body region of the individual. In one embodiment, the injection sites are illuminated with a first set of controllable light-emitting elements, e.g., one or more laser diodes, and the one or more annotations are projected with a second set of controllable light-emitting elements, e.g., a projector. In one embodiment, a single controllable light-emitting element, e.g., a projector, illuminates the one or more injection sites as well as projects the one or more annotations.

FIG. 35 illustrates aspects of a system 3500 including computer processor 3510 and non-transitory signal-bearing medium 3520 bearing one or more instructions for generating an injection guide. System 3500 further includes an image capture device 3530 which is operably linked to computer processor 3510 by either wired 3540 or wireless 3550 means. Non-transitory signal-bearing medium 3520 includes one or more instructions 3570 for receiving one or more digital images of a body region of an individual including one or more physical registration landmarks; one or more instructions 3575 for generating at least one digital representation of the body region using the one or more digital images, the at least one digital representation including one or more digital registration landmarks corresponding to the one or more physical registration landmarks on the body region; one or more instructions 3580 for adding one or more digitally registered injection sites to the at least one digital representation of the body region, the one or more digitally registered injection sites registered relative to the one or more digital registration landmarks; one or more instructions 3585 for generating one or more output signals having information for controlling one or more controllable light-emitting elements to illuminate a location on a surface of the body region of the individual corresponding in location to at least one of the one or more digitally registered injection sites; one or more instructions 3590 for receiving one or more second digital images of the body region of the individual, the one or more second digital images of the body region including the one or more physical registration landmarks and one or more illuminated injection sites; and one or more instructions for generating one or more output signals having information for adjusting the one or more controllable light-emitting elements so as to align the one or more illuminated injection sites relative to the one or more physical registration landmarks on the body region to substantially correspond to the at least one digital representation of the body region.

In one embodiment the system including a computer processor and non-transitory signal-bearing medium bearing one or more instructions for generating an injection guide can further include one or more instructions for registering a position of an injector relative to an injection site. In one embodiment, the non-transitory signal-bearing medium includes one or more instructions for registering a position of an injector relative to one or more illuminated injection sites; and one or more instructions for issuing an alarm if the injector is in an incorrect position of the body region relative to the one or more illuminated injection sites. In one embodiment, the non-transitory signal-bearing medium includes one or more instructions for registering a position of an injector relative to one or more illuminated injection sites; and one or more instructions for recording one or more injection events at the illuminated injection site. In one embodiment, the injector can be registered relative to an illuminated injection site based on feedback from an image capture device included in the system (see, for example, FIGS. 31 and 35). For example, the computer processor can include one or more instructions for recognizing an injector or accessory thereof in a captured image and assessing the injector's proximity to an illuminated injection site in the same captured image and issuing an alert if the injector is not properly located. In one embodiment, a real-time video stream may be used to monitor injector location. An injection event at the illuminated injection site can be recorded by the computer processor as, for example, an image. In one embodiment, the injector can be registered relative to the illuminated injection site based on interaction of some component of the injector with the illuminated injection site. For example, the injector may include an injector-tracking device including one or more photo-sensors that are activated when a specific portion of the injector, e.g., the injection needle, crosses the beam of light illuminating an injection site. In one embodiment, the injector-tracking device can directly issue an audible, visible, or haptic alert or alarm. In one embodiment, the injector-tracking device can send a signal, e.g., a radio-frequency signal, to another device, e.g., the computer processor, a headset, a phone, or other device, which then issues an alarm.

In one embodiment, non-transitory signal-bearing medium bearing one or more instructions for generating an injection guide can include one or more instructions for acquiring one or more digital images of the body region of the individual in at least one first expression state and at least one second expression state; one or more instructions for comparing the one or more digital images of the body region of the individual in the at least one first expression state and the at least one second expression state to determine an injection-treatment plan; and one or more instructions for adding the one or more digitally registered injection sites to the at least one digital representation of the body region based on the injection-treatment plan.

In one embodiment, an article of manufacture includes non-transitory signal-bearing medium bearing one or more instructions for guiding injection in an individual. The non-transitory signal-bearing medium includes one or more instructions for referencing one or more digitally registered injection sites on a three-dimensional model of a body region of an individual with one or more digital injection sites; and one or more instructions for controlling illumination of injection information for each digital injection site onto a surface of the body region of the individual. In one embodiment, the one or more digitally registered injection sites are represented by coordinates relative to the three-dimensional model of the body region. In one embodiment, the one or more digitally registered injection sites are represented by coordinates relative to one or more digital registration landmarks corresponding to one or more physical registration landmarks on the body region. In one embodiment, the one or more digital injection sites are represented by a visible mark, e.g., a color or pattern, on a digital display device, e.g., a computer monitor. The one or more digital injection sites substantially correspond to one or more illuminated injection sites. The injection information can include, but is not limited to, a physical injection site on the body region and/or information pertaining to the injection, e.g., a type of injectable agent, a type of injector, injection dosing, injection timing, injection sequence, injection angle, and/or injection depth.

FIG. 36 illustrates aspects of an article of manufacture for use in generating an injection guide. Article of manufacture 3600 includes non-transitory signal-bearing medium 3610 bearing one or more instructions for generating an injection guide. The non-transitory signal-bearing medium includes one or more instructions 3620 for receiving one or more digital images of a body region of an individual including one or more physical registration landmarks; one or more instructions 3630 for generating at least one digital representation of the body region using the one or more digital images, the at least one digital representation including one or more digital registration landmarks corresponding to the one or more physical registration landmarks on the body region; one or more instructions 3640 for adding one or more digitally registered injection sites to the at least one digital representation of the body region, the one or more digitally registered injection sites registered relative to the one or more registration landmarks; and one or more instructions 3650 for generating one or more output signals having information for controlling one or more controllable light-emitting elements to illuminate a location on a surface of the body region of the individual corresponding in location to at least one of the one or more digitally registered injection sites.

In one embodiment, a method for guiding injection in an individual includes projecting an injection-treatment pattern on a surface of a body region of the individual, the injection-treatment pattern part of a digitally-rendered injection-treatment plan and including one or more illuminated injection sites; placing one or more marks on the surface of the body region of the individual, the one or more marks substantially corresponding in location to the one or more illuminated injection sites; and injecting at least one injectable agent into an underlying tissue of the body region at or near at least one of the one or more marks.

Figure 37:
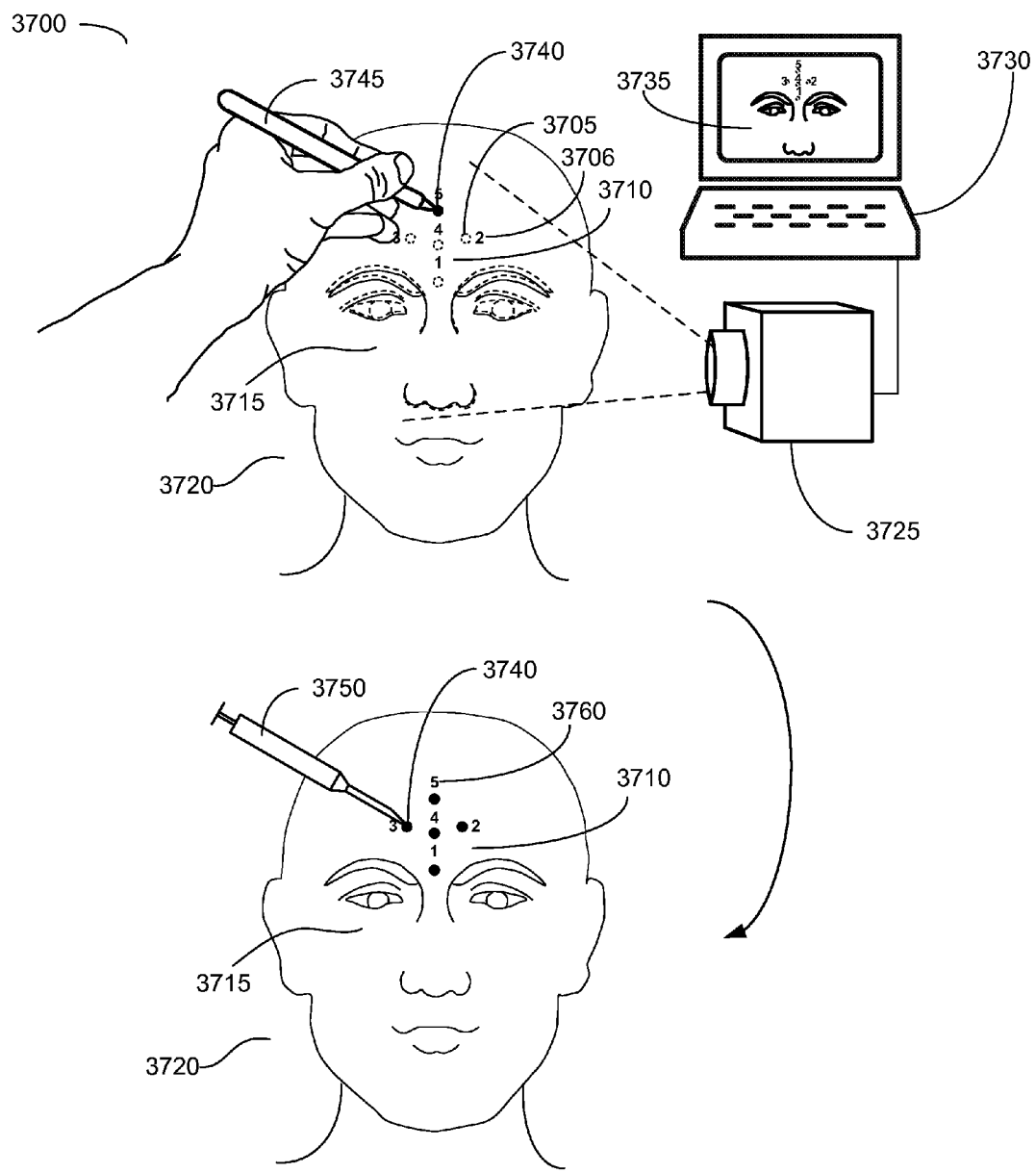
FIG. 37 is a schematic of a system for guiding injection in an individual.

FIG. 37 illustrates aspects of a method 3700 for guiding injection in an individual. Method 3700 includes projecting injection-treatment pattern 3710 on a surface of body region 3715 of individual 3720. Injection treatment-pattern 3710 can include one or more illuminated injection sites 3705. In one embodiment, injection-treatment pattern 3710 can further include one or more projected annotations 3706. In the non-limiting example shown in FIG. 37, one or more projected annotations 3706 are numbers indicating the sequence of injection. However, one or more projected annotations 3706 can include information regarding one or more of an injectable agent, an injector type, a dosage, a sequence of injection, a timing of injection, an angle of injection, and/or a depth of injection. Controllable light emitting element 3725 controllably projects injection-treatment pattern 3710 onto the surface of body region 3715 of individual 3720. Controllable light emitting element 3725 is operably connected to computing device 3730, the latter of which controls projection from controllable light emitting element 3725. Controllable light emitting element 3725 projects injection-treatment pattern 3710 including one or more illuminated injection sites 3705 and one or more projected annotations 3706 in accordance with digitally-rendered injection-treatment plan 3735 included in computing device 3730. Digitally-rendered injection-treatment plan 3735 can include at least one digital representation of the body region of the individual. The at least one digital representation of the body region can include one or more digital registration landmarks corresponding to one or more physical registration landmarks on the body region of the individual. The at least one digital representation of the body region can further include one or more digitally registered injection sites corresponding to the one or more injection sites illuminated on the surface of the body region. The digitally-rendered injection-treatment plan can further include one or more digitally-rendered annotations corresponding to the one or more projected annotations.

Method 3700 further includes placing one or more marks 3740 on the surface of body region 3715 with a marking tool 3745. Marking tool 3745 can include a pen or other marking device. Alternatively, marking can be done using one or more adhesive pieces, e.g., small round stickers. One or more marks 3740 substantially correspond in location to the one or more illuminated injection sites 3705. One or more annotation marks 3760 may also be placed on the surface of the body region substantially corresponding to one or more projected annotations 3706. Method 3700 further includes injecting one or more injectable agents with injector 3750 at one or more marks 3740 wherein one or more marks 3740 form a substantially equivalent injection-treatment pattern 3710 on the surface of body region 3715.

FIG. 38 illustrates aspects of a system for registering one or more illuminated injection sites. System 3800 includes computing device 3810 and non-transitory signal-bearing medium 3820 bearing one or more instructions for registering one or more illuminated injection sites. Non-transitory signal-bearing medium 3820 includes one or more instructions 3830 for acquiring a real-time image of a body region of an individual; one or more instructions 3840 for locating one or more physical registration landmarks on the real-time image of the body region of the individual; one or more instructions 3850 for matching the one or more physical registration landmarks with one or more digital registration landmarks in an injection-treatment plan, the injection-treatment plan including one or more digital injection sites; one or more instructions 3860 for mapping the one or more digital injection sites to one or more physical injection sites; and one or more instructions 3870 for controlling illumination of the one or more physical injection sites. In one embodiment, system 3800 optionally includes at least one image capture device 3880 and at least one controllable light emitting element 3885 operably connected via a wireless or wired transmission means 3890 to computing device 3810. In one embodiment, the injection-treatment plan is a digitally-rendered injection-treatment plan created on a computing device and stored on the computing device or other storage medium. In one embodiment, the injection-treatment plan includes at least one digital representation of a body region of an individual. In one embodiment, the digital injection sites include digitally registered injection sites, registered relative to one or more digital registration landmarks.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those skilled within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications, programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Various non-limiting embodiments are described herein as Prophetic Examples.

PROPHETIC EXAMPLES

Example 1

Generating an Illuminated Injection Guide for Cosmetic Treatment of a Facial Region with a Neurotoxin A system and method are described for generating an illuminated injection guide for cosmetic treatment of a facial region, e.g., forehead, of an individual with an injectable agent, e.g., *botulinum* toxin. The system includes a computing device including a processor, e.g., a desktop computer, and a non-transitory signal-bearing medium bearing one or more instructions implemented on the desktop computer. The system can optionally include one or more image capture devices for capturing digital images of the facial region of the individual.

A digital representation of the face of an individual is generated from one or more digital images of the individual's face, including at least a portion of the individual's forehead. The one or more digital images are received by the desktop computer either from a second computing device via wired or wireless transmission or from the one or more image capture devices. For the latter, two charge-coupled device cameras and a projector connected to the desktop computer are used to scan the body region of the individual's face, as described in Feng et al. *Brit. J. Oral Maxillofacial Surg.* (2010) 48:105-109, which is incorporated herein by reference. The individual's face is exposed to structured light, which the cameras collects upon reflection to obtain an optical representation of the body region by a point cloud of up to 300,000 points in three-dimensional coordinates. The three-dimensional coordinates are acquired by the computer and used to construct a digital representation of the face using a CAD/CAM software package, e.g., Geomagic Studio (Morrisville, N.C.). One or more physical registration landmarks, e.g., anatomical features of the face, are incorporated into the digital representation of the face as digital registration landmarks.

Digitally registered injection sites are added to the digital representation of the individual's face. The digitally registered injection sites can be added automatically by the computing device based on a preprogrammed injection-treatment plan. Alternatively, the digitally registered injection sites are added to the digital representation of the individual's face by a physician or other practitioner using a user input device, e.g., a keyboard or touchpad associated with the desktop computer. The physician or other practitioner may work directly with the individual to position the digitally registered injection sites so as to attain a desired outcome, e.g., reducing wrinkles without excessively immobilizing facial muscles.

The digitally registered injection sites are added to the digital representation in an injection-treatment pattern. The injection-treatment pattern includes a triangular pattern of 9 to 13 digitally registered injection sites which are added to the region of the digital representation corresponding to the individual's forehead. The 9 to 13 digitally registered injection sites correspond to intended injections sites for *botulinum* toxin on the individual's forehead. The digitally registered injection sites are added to the digital representation relative to physical registration landmarks represented by digital registration landmarks. In this example, the physical landmarks include the eye brows, frontal scalp line, and midline of the forehead. The digitally registered injection sites are registered 0.5 centimeters below the lateral brow; in the midpupillary line, halfway between the eyebrow and the frontal scalp on each side of the model; at the vertex of the forehead; at the midline just below the meeting of the eyebrows; at the midline of the forehead, halfway between the nasal radix and the vertex of the scalp; and over the corrugators, approximately 1 centimeter above the medial portion of the each eyebrow (see, e.g., Bain et al., *Aesthetic Surg. J.* (2006) 26:617-619, which is incorporated herein by reference).

The digitally registered injection sites further include information regarding treatment parameters in the form of letters, number, and/or colors. The digitally registered injection site are represented by "B3" to represent 3 Units of *botulinum* toxin to be injected at said site. Typical dosages of *botulinum* toxin per injection site range from 1 to 6 Units. The placement of injection sites as well as the treatment patterns can be either automatically added to the digital representation or added by a physician or other practitioner using a user input device. The physician or other practitioner can also decide how many units should be injected per injection site based on the depth and/or intensity of the wrinkles on the individual's forehead, and add that information to the digital representation.

The digital representation including the digitally registered injection sites corresponding to one or more illuminated injection sites and one or more digital registration landmarks corresponding to one or more physical registration landmarks is directly by the computing device on which it was generated to proceed with guided injection using illuminated injection sites or can be sent via a wireless transmission to another computing device for actual injection treatment.

Example 2

Illuminating Injection Sites on the Surface of a Facial Region of an Individual for Guided Injection of *Botulinum* Toxin A system and method of guiding injection in an individual is described. The system consists of controllable light-emitting elements, e.g., laser diodes, wired to a computing device including a processor, e.g., a laptop computer, and an image capture device, e.g., a digital camera. A digital representation of the facial region of an individual in need of treatment is received by the computing device via the internet, from a referring physician. The digital representation includes digital registration landmarks corresponding to physical registration landmarks on the face of the individual. The physical registration landmarks include anatomical features, e.g., nose, eyes, cheeks, wrinkles, and the like, as well as pigmented areas, e.g., freckles associated with the facial region of the individual. The digital representation also includes digitally registered injection sites that have been registered relative to the digital registration landmarks. In this example, the digitally registered injection sites are added to the digital representation of the facial region in accordance with an injection-treatment plan, by the referring physician using one or more of the methods described herein prior to transmission of the digital representation to the laptop computer.

The laptop computer is operable to control the controllable laser diodes to emit light onto the surface of the facial region of the individual in accordance with the injection-treatment plan. A first set of laser diodes emits red light, a second set of laser diodes emits green light, and a third set of laser diodes emits blue light. The color of light emitted depends upon the dose of *botulinum* toxin required at a given illuminated injection site. The illuminated injection sites corresponding to the digitally registered injection sites are arranged in an injection-treatment pattern. In this example, the injection-treatment pattern of illuminated injection sites is arranged for treatment of the glabella region, i.e., the space between the eyebrows. In this instance, the glabella region can be divided into the superior-lateral region and the central and inferomedial regions. Injection sites are illuminated on the superior-lateral region over the medial portion of the corrugators muscle near its origin. Additional injection sites are illuminated over the mid portion of the muscle belly. Each of these sites is illuminated with red light indicating treatment with 5 units of *botulinum* toxin. In addition, injection sites are illuminated over the middle of the procerus muscle belly which is slightly off midline at the level of the superior orbital rims. This pattern is repeated on the other side. Each of these sites is illuminated with green light indicating treatment with 6 units of *botulinum* toxin. Injection sites are illuminated over the depressor supercilli muscle, which is approximately 1 centimeter above the medial canthal tendon on both sides. Each of these sites is illuminated with blue light indicating treatment with 3 units of *botulinum* toxin.

A physician or other practitioner prepares the *botulinum* toxin, e.g., *botulinum* toxin A (sold under the trademark BOTOX), for injection. A 100 Unit vial of BOTOX, which has been stored frozen, is thawed and mixed with 2.5-4.0 milliliters (ml) of 0.9% non-preserved sterile saline solution to create a final concentration of 40-25 Units/ml. Saline including a preservative or water for injection (WFI) can also be used for this purpose.

In some instances, depending on the sensitivity/pain threshold of the individual, the surface of body region is coated with a layer of anesthetic cream, e.g., a eutectic mix of the local anesthetics lidocaine (2.5%) and prilocaine (2.5%), prior to injection. Alternatively or in addition, the surface of the body region is cooled with application of an ice pack for 10-15 minutes as a means of reducing the pain of injection and/or post-injection swelling. A 1 or 3 ml syringe with a 30-gauge needle is used for injection, although needles ranging in gauge from 27 to 32 can be used for this purpose. Appropriate length needles for this purpose include ½ inch (12.7 mm), 5/16 inch (8 mm) and 3/16 inch (5 mm) lengths. A syringe including a 30-gauge needle is filled with the appropriately prepared *botulinum* toxin, and the needle is inserted into the underlying tissue of the body region at an illuminated injection site, and the appropriate amount of *botulinum* toxin is injected based on the color of the illuminated injection site. Similar steps are repeated for additional injections until all the illuminated injection sites of the treatment pattern have been injected. In some treatments a single syringe may be filled with enough *botulinum* toxin for the entire treatment pattern, and the needle is changed between injections, or the same needle is used for all injections.

The image capture device, e.g., digital camera, of the system provides feedback as to where the illuminated injection sites are relative to the physical registration landmarks. For example, the digital camera captures images of the illuminated injection sites on the surface of the facial region and including the physical registration landmarks. This information is processed by tracking software in the laptop computer, and signals are sent to the controllable laser diodes to adjust the positioning of where they are illuminating the surface of the body region, in order to keep the illuminated injection sites appropriately registered.

The individual may return from 30 to 120 days later for a repeat course of injections, depending upon the sustainability of the treatment. In repeat visits, the same injection-treatment pattern of illuminated injection sites may be used, if appropriate. Alternatively, the physician or other practitioner may alter the illuminated injection sites and/or the associated treatment parameters.

Example 3

Illuminating One or More Injection Sites on the Surface of a Facial Region of an Individual for Guided Injection of a Hyaluronic Filler Generation and use of one or more illuminated injection sites in an injection-treatment pattern is described. The injection-treatment pattern is part of an injection-treatment plan designed to treat the skin folds associated with the nasolabial folds, i.e., "laugh lines," of an individual's face with injected hyaluronic acid filler.

A digital representation is generated from one or more digital images of at least a portion of an individual's face, with particular emphasis on the nasolabial folds. The digital representation is generated using the image capture methods described in Example 1. Alternatively, the digital representation of the individual's face is generated using a PRIMOS optical three-dimensional in vivo skin measurement device (GFMesstechnik, Teltow, Germany). This system projects structured light, e.g., a parallel stripe pattern, onto the face of the individual, the reflection of which is captured on a charge-coupled device chip of a shooting camera through a shooting optic. The measurement system consists of a freely movable optical measurement head (with an integrated micro-mirror projector, a projection optic, a shooting optic, and a charge-coupled device recording camera) together with a computer system. A three-dimensional effect is achieved by deflection of the parallel projection stripes by the topography the individual's face. The deflections are digitalized and quantitatively evaluated using software. Mathematical algorithms are used to generate a three-dimensional image of the individual's face, which becomes the basis for the digital representation (see, e.g., Levenberg *Eur. J. Dermatol.* (2010) 20:615-619, which is incorporated herein by reference).

A pattern of one to ten digitally registered injection sites is added to the digital representation of the individual's face, each injection site represented by a circle. Injection of hyaluronic acid into the nasolabial folds can be done at a single injection site by the process of threading or at multiple injection sites along the fold. Threading involves injecting the needle under the skin all the way to a distant point and then slowly removing the needle while releasing the injectable agent. To accommodate threading, in which the injection needle is injected at an angle of about 10 to 30 degrees relative to plane of the skin surface, annotations are added to the digital representation and are projected onto the individual's face. For example, an annotation indicating an angle of injection, e.g., 25 degrees, at the illuminated injection sites is added to the digital representation. For multiple injection sites, multiple digitally registered injection sites are added to the digital representation relative to a linear path along the nasolabial fold.

Annotations are added to the digital representation to indicate the dosage of hyaluronic acid filler to be used at each injection site. For injection into the nasolabial folds, the injection volume can be as high as 6 ml per fold, although the preferable volume is 1-3 ml per fold, and depends upon the depth of the fold and how much "correction" is desired by the individual (see, e.g., Prager & Steinkraus *Eur. J. Dermatol.* (2010) 20:748-752, which is incorporated herein by reference). The physician or other practitioner can determine the appropriate dosage of the hyaluronic filler by assessing the depth of the nasolabial fold from either viewing the individual's face directly or viewing the captured and processed three-dimensional image of the individual's face on a computer monitor. Alternatively, the computing device used to generate the digital representation can include one or more algorithms to determine the appropriate dosage based on the captured image information.

The surface of the individual's face is wiped with a disinfectant, e.g., rubbing alcohol, and the injection sites are illuminated using a mini projector, e.g., a 3M™ Mobile Projector MP220 (from 3M, St. Paul, Minn.). The illuminated injection sites correspond to the digitally registered injection sites. The projector also projects the annotations onto the surface of the body region.

The hyaluronic acid filler for injection is preferably one of the agents approved by the United States Food & Drug Administration (FDA), e.g., Restylane® (from Medicis Aesthetics Inc., Scottsdale, Ariz.). Restylane® is provided by the manufacturer in a disposable glass syringe. Needles ½ inch in length and either 29 or 30 gauge are recommended for use with this product. The hyaluronic acid filler is injected at the illuminated injection sites with instructions from the annotations, the annotations including treatment parameters and/or other instructions pertinent to the injection-treatment plan.

Example 4

A System for Feedback Guided Injection of an Individual with Blepharospasm (Eye-Lid Spasm)

An embodiment of a system and method are described for guiding neurotoxin injection in an individual for treatment of blepharospasm (eye-lid spasm). The system includes controllable light-emitting elements configured to emit nondestructive light, a computing device including a processor, and an injector-tracking device. The system can also optionally include an image capture device.

A digital representation of the facial region of an individual with blepharospasm is received by the computing device of the system, the digital representation including digital registration landmarks corresponding to physical registration landmarks. The physical registration landmarks include the inner and outer canthi of both eyes, the pre-tarsal orbicularis oculi of the upper lid, the lateral pre-tarsal orbicularis oculi of the lower lid, the levator palpebrae superioris, the medial lower lid, the center of the upper lip, the outer corners of the mouth, the intersection of the frontal bone and two nasal bones of the skull (nasion), the tip of the nose (pronasale), a subnasal point, and a chin point.

The digital representation of the individual's face further includes digitally registered injection sites added to the digital representation of the eye-lid area of the individual. The digitally registered injection sites are represented by crosshairs to indicate injection sites. The crosshairs vary in color to indicate specific treatment parameters, e.g., the dose of *botulinum* toxin used at each injection site. For the treatment of blepharospasm with a *botulinum* toxin, e.g., BOTOX® (from, Allergan, Inc., Irvine, Calif.), the digitally registered injection sites are registered relative to the eye-lid region corresponding to regions either proximal to or over the medial and lateral pre-tarsal orbicularis oculi of the upper lid and into the lateral pre-tarsal orbicularis oculi of the lower lid. Care is taken to avoid registering injection sites near the levator palpebrae superioris and the medial lower lid to avoid complications of ptosis and diplopia, respectively. A series of digitally registered injection sites represented by crosshairs and corresponding to 5 to 10 individual injection sites per eye are added to the digital representation. In addition, annotation is added to the digital representation indicating the number units of *botulinum* toxin to be injected, e.g., 1.25 to 3.0 units per injection, for a total of 30 units per eye. The digitally registered injection sites are also registered so as to avoid injection into an underlying blood vessel. The location of underlying blood vessels are imaged using a light-emitting diode illumination system such as that described in U.S. Patent Application 2008/0306392, which is incorporated herein by reference. Information regarding blood vessel location is added to the digital representation of the individual's face and avoided when placing the digitally registered injection sites.

The injection sites are illuminated onto the surface of the individual's face with laser diodes, the illuminated injection sites corresponding to the digitally registered injection sites. Each injection site on the surface of the individual's face is sequentially illuminated with a crosshair approximately 9 millimeters in length. The crosshair is generated using a crosshair diffractive diffuser (DE-R 201 Cross-5 from Frankfurt Laser Co., Germany) and a red (633 nm) laser diode.

BOTOX is prepared for injection per the manufacturer's instructions. A 30 gauge needle with a length of 4 mm is used for injecting 1.5 units of BOTOX per injection site at the illuminated injection sites. A syringe including the 30 gauge needle includes a removable injector-tracking device for tracking movement of the syringe relative to the illuminated injection sites. The injector-tracking device includes a photo-sensor that is a photo diode with high performance in ambient light, e.g., the dimmed background light in a treatment room, as described in U.S. Pat. No. 7,891,570, which is incorporated herein by reference. The injector-tracking device includes a processor capable of subtracting out signals due to the ambient light relative to the bright red illuminated injection site. The injector-tracking device further includes a miniature audio chip operably connected to the photo-sensor and configured to emit a peeping sound when the photo-sensor is activated by proximity of the syringe to the illuminated injection site. BOTOX is injected into the underlying eyelid area to a depth of 2 mm. Each treatment lasts approximately three months, following which the procedure may be repeated. At that time, the injection-treatment pattern and/or the treatment parameters may be modified.

Example 5

Illuminating Pattern of Injection Sites for Self-Injection of Ovulation Stimulating Hormones Systems and methods are described for illuminating a pattern of injection sites onto the upper thigh of an individual as part of an injection-treatment plan for self-injecting hormones to induce ovulation for use in in-vitro fertilization.

A digital image of the upper thigh of an individual is acquired using one of the methods previously described herein. Alternatively, digital images of the upper thigh of the individual are acquired with a standard digital camera and combined with images of blood vessels at or near the surface of the skin. An example of an apparatus for imaging blood vessels is described in U.S. Pat. No. 6,522,911, which is incorporated herein by reference. The digital images further ideally include one or more physical registration landmarks, e.g., freckles, moles, tattoos, etc., for registering digitally registered injection sites. If no visible landmarks are present on the surface of the body region, the physician or other practitioner can add markings, e.g., ink or adhesive pieces, to the upper thigh for use as physical registration landmarks. The digital images are used by a computing device to generate a digital representation of the upper thigh including digital registration landmarks corresponding to the physical registration landmarks.

A series of digitally registered injection sites are added to the digital representation of the body region. The number of digitally registered injection sites is dependent upon the number of planned injections during the ovulation cycle. The number of planned injections is further dependent upon the types of injectable hormones used and the menstrual cycle of the individual. Eggs are matured in vivo prior to harvesting for in vitro fertilization using some combination of gonadotropin-releasing hormone (GnRH) antagonists, follicle-stimulating hormone (FSH), and human chorionic gonadotropin (hCG). In this example, the injection-treatment plan is individualized to the individual's menstrual cycle and includes multiple injections of the GnRH antagonist leuprolide acetate, e.g., Lupron, and FSH over the course of 14 to 21 days, and a final injection with hCG two days prior to harvesting eggs. Digitally registered injection sites are added to the digital representation of the upper thigh, the digitally registered injection sites represented by letters, numbers, and shapes. The letter, number, and shapes further indicate treatment parameters, e.g., the type of drug to be injected, the dose of drug to be injected, and/or the day in the treatment cycle. Alternatively or in addition, treatment parameters are included as annotations that are projected at or near illuminated injection sites.

Figure 39A:
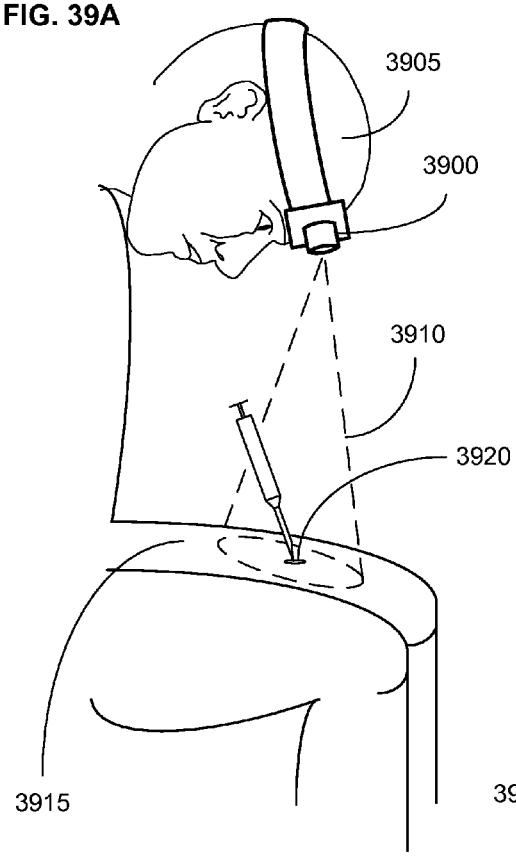
FIGS. 39A & 39B are schematics of an embodiment of a system for guiding injection in an individual for fertility treatment.

The digital representation of the upper thigh, including the digitally registered injection sites, the digital registration landmarks, any annotations, and instructions for projecting the injection guide, are received by a computing device incorporated in a head-mounted system. The head-mounted system includes the computing device, controllable light-emitting elements, and an image capture device. An illustrative example of a head-mounted system and an annotated injection-treatment pattern are provided in FIG. 39. FIG. 39A shows head-mounted system 3900 worn on head region 3905 of an individual. In this example, head-mounted system 3900 is attached to a strap encircling head region 3905, but the system could be incorporated into a hat or other head covering. Head-mounted system 3900 emits light beam 3910 onto the surface of the upper thigh 3915. Light beam 3910 illuminates injection site 3920.

Figure 39B:
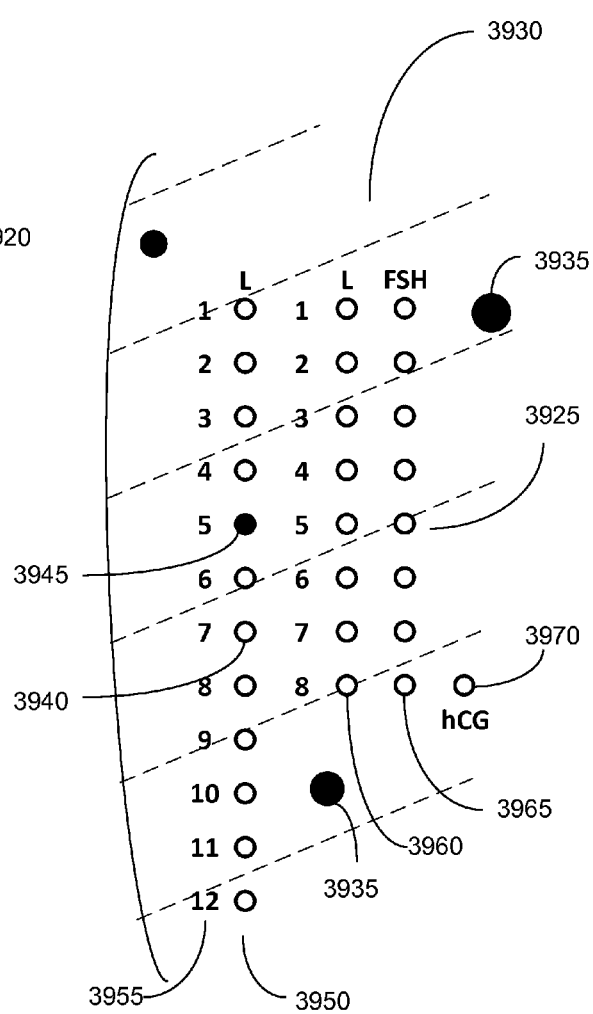

FIG. 39B illustrates a non-limiting example of an injection guide 3925 in which illuminated injection sites and annotations are projected onto the surface of a body region 3930. The illuminated injection sites are aligned based on physical registration landmarks 3935, e.g., two or more freckles, on the surface of the upper thigh. In general, the injection cycle is as follows: On day 1 (which corresponds to day 21 of the menstrual cycle) the injection cycle is initiated by injecting the first Lupron injection. On day 9-12 (which corresponds to the day after the beginning of menstruation and is variable depending upon number of days in cycle) initiate 7 days of FSH injection. On day 16, finish injection cycle with the last injections of Lupron and FSH, and a single injection of HCG. Egg retrieval is performed 2 days after HCG injection. In the non-limiting example depicted in FIG. 39B, injection sites are illuminated in a color-coded fashion onto the surface of body region 3930. Injection site 3940 is illuminated with a first color, e.g., white light, while injection site 3945 is illuminated with a second color, e.g., green light. Each day, all injection sites are illuminated with white light, with the exception of the injection site of the day, which is illuminated with a second color of light, e.g., green light. Sites that have been previously injected may be optionally illuminated with a third color of light, e.g., red light Annotations are projected onto body region 3930 in proximity to injection sites 3940 and 3945, providing pieces of information related to the injection day and the drug to be injected on a given day. For example, a first column 3950 illuminated injection sites is annotated with a projected "L" for Lupron and numbered in a descending manner 3955 to indicate the first day of Lupron injection, the second day of Lupron injection, etc., out to the twelfth day of Lupron injection. A second column 3960 and a third column 3965 of illuminated injection sites are annotated with projected "L" and "FSH", respectively, and are similarly numbered to indicate the injection day. The fourth column 3970 has a single illuminated injection site reserved for the final injection of HCG two days prior to harvesting of eggs.

All of the above U.S. patents, U.S. patent application publications, U.S. patent applications, foreign patents, foreign patent applications and non-patent publications referred to in this specification and/or listed in any Information Disclosure Statement, are incorporated herein by reference, to the extent not inconsistent herewith.

With respect to the appended claims, the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for guiding injection in an individual comprising:
   one or more controllable light-emitting elements configured to emit non-destructive light;
   at least one image capture device;
   a digitally-rendered injection-treatment plan stored on a computer-readable medium, the digitally-rendered injection-treatment plan part of an injection-treatment plan and including one or more digitally registered injection sites arranged in an injection-treatment pattern on a digital representation of a skin surface of an individual, the one or more digitally registered injection sites registered relative to one or more digital registration landmarks corresponding to one or more physical registration landmarks on the skin surface of the individual; and
   a computing device operably connected to the one or more controllable light-emitting elements and the at least one image capture device, the computing device including a processor and
      circuitry configured to receive the digitally-rendered injection-treatment plan from the computer-readable medium;
      circuitry configured to actuate at least one of the one or more controllable light-emitting elements to illuminate one or more injection sites on the skin surface of the individual in the injection-treatment pattern in accordance with the digitally-rendered injection-treatment plan;
      circuitry configured to receive from the at least one image capture device one or more digital images of a visual field including the skin surface of the individual, the visual field including the illuminated one or more injection sites and the one or more physical registration landmarks on the skin surface of the individual; and
      circuitry configured to adjust the at least one of the one or more controllable light-emitting elements so as to align the illuminated one or more injection sites relative to the one or more physical registration landmarks on the skin surface of the individual to substantially correspond to the digitally rendered injection-treatment plan.

2. The system of claim 1, wherein at least one of the one or more controllable light-emitting elements is configured to emit at least one first color of light and at least one second color of light.

3. The system of claim 1, wherein at least one of the one or more controllable light-emitting elements is configured to emit a pattern of light in the shape of one or more letters, numbers, symbols, or combinations thereof.

4. The system of claim 1, wherein the computing device includes circuitry configured to control one or more of a color of light or a pattern of light emitted from the one or more controllable light-emitting elements.

5. The system of claim 1, wherein the computing device includes circuitry configured to actuate one of the one or more controllable light-emitting elements to illuminate a first injection site at a first location on the skin surface of the individual at a first time point and to illuminate a second injection site at a second location on the skin surface of the individual at a second time point.

6. The system of claim 1, wherein the computing device includes circuitry configured to actuate the one or more controllable light-emitting elements to illuminate each of the one or more injection sites on the skin surface of the individual in a temporal sequence.

7. The system of claim 1, wherein at least one of the one or more controllable light-emitting elements is a projector, the projector operably coupled to the computing device to project onto the skin surface of the individual at least a portion of the digitally-rendered injection-treatment plan including at least one of the one or more digitally-registered injection sites.

8. The system of claim 7, wherein the projected at least a portion of the digitally-rendered injection-treatment plan includes one or more treatment parameters represented by one or more letters, numbers, shapes, symbols, text, colors, or combinations thereof.

9. The system of claim 7, wherein the projected at least a portion of the digitally-rendered injection-treatment plan includes one or more injection status updates represented by one or more letters, numbers, shapes, symbols, text, colors, or combinations thereof, wherein the one or more injection status updates include at least one of a running clock, a number of injections completed, or a number of injections remaining.

10. The system of claim 1, wherein the at least one image capture device includes at least one digital camera.

11. The system of claim 1 wherein the computing device includes
   circuitry configured to register a position of an injector relative to the illuminated one or more injection sites on the skin surface of the individual in the received one or more digital images of the visual field of the skin surface of the individual; and
   circuitry configured to issue an alarm in response to the registered position of the injector relative to the illuminated one or more injection sites on the skin surface of the individual.

12. The system of claim 1 wherein the computing device includes
   circuitry configured to register a position of an injector relative to at least one of the illuminated one or more injection sites on the skin surface of the individual in the received one or more digital images of the visual field of the skin surface of the individual; and
   circuitry configured to record to a data storage device one or more injection events at the at least one of the illuminated one or more injection sites on the skin surface of the individual.

13. The system of claim 1 further comprising:
   an injector-tracking device sized for attachment to an injector and including at least one alert component and one or more photo-sensors, wherein the at least one alert component is configured to transmit an alert signal in response to a position of the one or more photo-sensors relative to the illuminated one or more injection sites.

14. The system of claim 1, wherein the computing device includes
   circuitry configured to receive one or more digital images of the skin surface of the individual including the one or more physical registration landmarks from the at least one image capture device;
   circuitry configured to generate the at least one digital representation of the skin surface of the individual using the one or more digital images, the at least one digital representation including the one or more digital registration landmarks corresponding to the one or more physical registration landmarks on the skin surface of the individual;
circuitry configured to identify an area of the skin surface of the individual in need of treatment by comparison of the at least one digital representation of the skin surface of the individual and at least one stored representation of at least one comparable skin surface;
circuitry configured to generate the digitally rendered injection-treatment plan based on the identified area of the skin surface of the individual in need of treatment; and
circuitry configured to add the one or more digitally registered injection sites to the at least one digital representation of the skin surface of the individual based on the digitally rendered injection-treatment plan, the one or more digitally registered injection sites registered relative to the one or more digital registration landmarks.

15. The system of claim 1, further comprising:
a head-mounted system, the head-mounted system mountable to a head region of a user and including the one or more controllable light-emitting elements configured to emit non-destructive light and at least one transmission unit including an antenna.

16. The system of claim 1, wherein the one or more controllable light-emitting elements configured to emit non-destructive light include at least one first controllable light-emitting element configured to emit a first color of non-destructive light and at least one second controllable light-emitting element configured to emit a second color of non-destructive light.

17. The system of claim 1, wherein the injection-treatment plan includes at least one treatment parameter represented by a color of light, a pattern of light, or a combination thereof.

18. The system of claim 1, further comprising:
the one or more controllable light-emitting elements configured to emit non-destructive light;
at least one digital camera;
a digitally-rendered injection-treatment plan stored on a computer-readable medium, the digitally-rendered injection-treatment plan part of a cosmetic injection-treatment plan to treat one or more lines, wrinkles, folds, or pouches in need of treatment on the individual's face, the digitally-rendered injection-treatment plan including one or more digitally registered injection sites arranged in an injection-treatment pattern on a digital representation of the skin surface of the individual's face, the one or more digitally registered injection sites registered relative to one or more digital registration landmarks corresponding to one or more physical registration landmarks on the skin surface of the individual's face, the injection-treatment pattern aligned with the one or more lines, wrinkles, folds, or pouches in need of treatment on the individual's face; and
the computing device operably connected to the one or more controllable light-emitting elements and the at least one digital camera, the computing device including the processor and
circuitry configured to receive the digitally-rendered injection-treatment plan from the computer-readable medium;
circuitry configured to actuate the one or more of the controllable light-emitting elements to illuminate one or more injection sites on the skin surface of the individual's face in the injection-treatment pattern in accordance with the digitally-rendered injection-treatment plan, the illuminated one or more injection sites situated over one or more lines, wrinkles, folds, or pouches in need of treatment on the individual's face;
circuitry configured to receive from the at least one digital camera one or more digital images of a visual field including the skin surface of the individual's face, the visual field including the illuminated one or more injection sites and the one or more physical registration landmarks on the skin surface of the individual's face;
circuitry configured to adjust the one or more of the controllable light-emitting elements so as to align the illuminated one or more injection sites relative to the one or more physical registration landmarks on the skin surface of the individual's face to substantially correspond to the digitally rendered injection-treatment plan.

19. The system of claim 1, further comprising:
non-transitory signal-bearing medium bearing one or more instructions executable by the computing device, the non-transitory signal-bearing medium including
one or more instructions for receiving the digitally-rendered injection-treatment plan from the computer-readable medium;
one or more instructions for actuating the one or more controllable light emitting elements to illuminate the one or more injection sites on the skin surface of the individual in the injection-treatment pattern in accordance with the digitally-rendered injection-treatment plan;
one or more instructions for acquiring the one or more digital images from the at least one image capture device, the one or more digital images including the visual field of the skin surface of the individual including the illuminated one or more injection sites and the one or more physical registration landmarks on the skin surface of the individual; and
one or more instructions for adjusting the one or more controllable light-emitting elements so as to align the illuminated one or more injection sites relative to the one or more physical registration landmarks on the skin surface of the individual to substantially correspond to the digitally-rendered injection-treatment plan.

20. The system of claim 1, further comprising:
non-transitory signal-bearing medium bearing one or more instructions executable by the computing device, the non-transitory signal-bearing medium including
one or more instructions for acquiring one or more digital images of the skin surface of the individual including the one or more physical registration landmarks with the at least one image capture device;
one or more instructions for generating the at least one digital representation of the skin surface of the individual from the one or more digital images, the at least one digital representation of the skin surface of the individual including the one or more digital registration landmarks corresponding to the one or more physical registration landmarks on the skin surface of the individual;
one or more instructions for identifying an area of the skin surface of the individual in need of treatment by comparison of the at least one digital representation of the skin surface of the individual and at least one stored representation of at least one comparable skin surface;

one or more instructions for generating the digitally rendered injection-treatment plan based on the identified area of the skin surface of the individual in need of treatment; and one or more instructions for adding the one or more digitally registered injection sites to the at least one digital representation of the skin surface of the individual based on the digitally rendered injection-treatment plan, the one or more digitally registered injection sites registered relative to the one or more digital registration landmarks.

21. The system of claim 1, wherein the one or more digitally registered injection sites arranged in the injection-treatment pattern on the digital representation of the skin surface of the individual are aligned with one or more of lines, wrinkles, pouches, or folds in need of treatment identified in the digital representation of the skin surface of the individual.

22. The system of claim 20, wherein the computing device includes circuitry configured to actuate the one or more of the controllable light-emitting elements to illuminate one or more injection sites over one or more lines, wrinkles, pouches, or folds on the skin surface of the individual to correspond with the one or more of the lines, wrinkles, pouches, or folds in need of treatment identified in the digital representation of the skin surface of the individual.

23. The system of claim 1, wherein the one or more controllable light-emitting elements configured to emit non-destructive light, the at least one image capture device, and the computing component operably coupled to the one or more controllable light-emitting elements and the at least one image capture device are part of a head-mounted system, the head-mounted system mountable to a head region of a user, the head-mounted system further including at least one transmission unit including an antenna, the computing device including circuitry configured to receive at least a portion of the digitally-rendered injection-treatment plan through the at least one transmission unit.

* * * * *